(12) United States Patent
Antonchuk et al.

(10) Patent No.: US 9,290,731 B2
(45) Date of Patent: Mar. 22, 2016

(54) FILTER APPARATUS AND FILTER PLATE SYSTEM

(75) Inventors: Jennifer Antonchuk, Vancouver (CA); Cindy Miller, Vancouver (CA)

(73) Assignee: STEMCELL TECHNOLOGIES INC., Vancouver, B.C. (CA)

( * ) Notice: Subject to any disclaimer, the term of this patent is extended or adjusted under 35 U.S.C. 154(b) by 850 days.

(21) Appl. No.: 13/139,044

(22) PCT Filed: Dec. 16, 2009

(86) PCT No.: PCT/CA2009/001885
§ 371 (c)(1),
(2), (4) Date: Jun. 10, 2011

(87) PCT Pub. No.: WO2010/069080
PCT Pub. Date: Jun. 24, 2010

(65) Prior Publication Data
US 2011/0233148 A1    Sep. 29, 2011

Related U.S. Application Data

(60) Provisional application No. 61/139,074, filed on Dec. 19, 2008.

(51) Int. Cl.
| | |
|---|---|
| *B01D 35/28* | (2006.01) |
| *B01D 39/08* | (2006.01) |
| *B01D 39/10* | (2006.01) |
| *B01D 37/00* | (2006.01) |
| *B01D 35/30* | (2006.01) |
| *C12M 1/00* | (2006.01) |
| *G01N 1/40* | (2006.01) |
| *B01D 39/16* | (2006.01) |
| *G01N 1/34* | (2006.01) |

(52) U.S. Cl.
CPC .............. *C12M 47/02* (2013.01); *B01D 35/30* (2013.01); *B01D 39/1692* (2013.01); *G01N 1/4077* (2013.01); *B01D 2201/30* (2013.01);
(Continued)

(58) Field of Classification Search
CPC ........... G01N 1/34; G01N 1/40; G01N 1/405; G01N 1/4077; G01N 2001/4088; C12M 47/02; C12M 47/00; C12N 1/02; B01D 39/1692; B01D 35/30; B01N 2201/30
See application file for complete search history.

(56) References Cited

U.S. PATENT DOCUMENTS

| 1,711,093 A | 10/1928 | Helman | |
|---|---|---|---|
| 2,466,999 A * | 4/1949 | Rohland | ........................ 229/243 |

(Continued)

FOREIGN PATENT DOCUMENTS

CH        674713 A5      7/1990

OTHER PUBLICATIONS

Abstract of CH 674713 A5, Published Jul. 13, 1990.

*Primary Examiner* — Christopher A Hixson
(74) *Attorney, Agent, or Firm* — Bereskin & Parr LLP/S.E.N.C.R.L., s.r.l.

(57) ABSTRACT

A filter apparatus comprises a filter having first and second opposed surfaces. A first reservoir is positioned adjacent with the first surface and in communication with the first surface, and a first inlet-outlet port is in communication with the first reservoir and spaced from the first surface. A second reservoir is positioned adjacent the second surface, and in communication with the second surface, and a second inlet-outlet port is in communication with the second reservoir and spaced from the second surface. A filter plate system comprises a reservoir plate. The reservoir plate comprises at least one reservoir well. The filter plate system further comprises a strainer plate. The strainer plate comprises at least one strainer well, which is removably receivable in the reservoir well. The strainer well comprises at least one mesh wall portion.

26 Claims, 36 Drawing Sheets

(52) U.S. Cl.
CPC ............... *G01N 1/34* (2013.01); *G01N 1/405* (2013.01); *G01N 2001/4088* (2013.01)

(56) References Cited

U.S. PATENT DOCUMENTS

| | | |
|---|---|---|
| 4,584,099 A | 4/1986 | Burton |
| 5,085,773 A | 2/1992 | Danowski |
| 5,219,529 A | 6/1993 | Ngo et al. |
| 5,593,587 A | 1/1997 | Fumihiko |
| 5,711,875 A | 1/1998 | Kayal et al. |
| 5,976,824 A * | 11/1999 | Gordon ............... 435/29 |
| 2003/0070975 A1* | 4/2003 | Hogan et al. ............ 210/232 |
| 2005/0189286 A1* | 9/2005 | Ferguson ............... 210/406 |
| 2006/0286003 A1 | 12/2006 | Desilets et al. |
| 2007/0298451 A1* | 12/2007 | Ribault et al. ............ 435/30 |

* cited by examiner

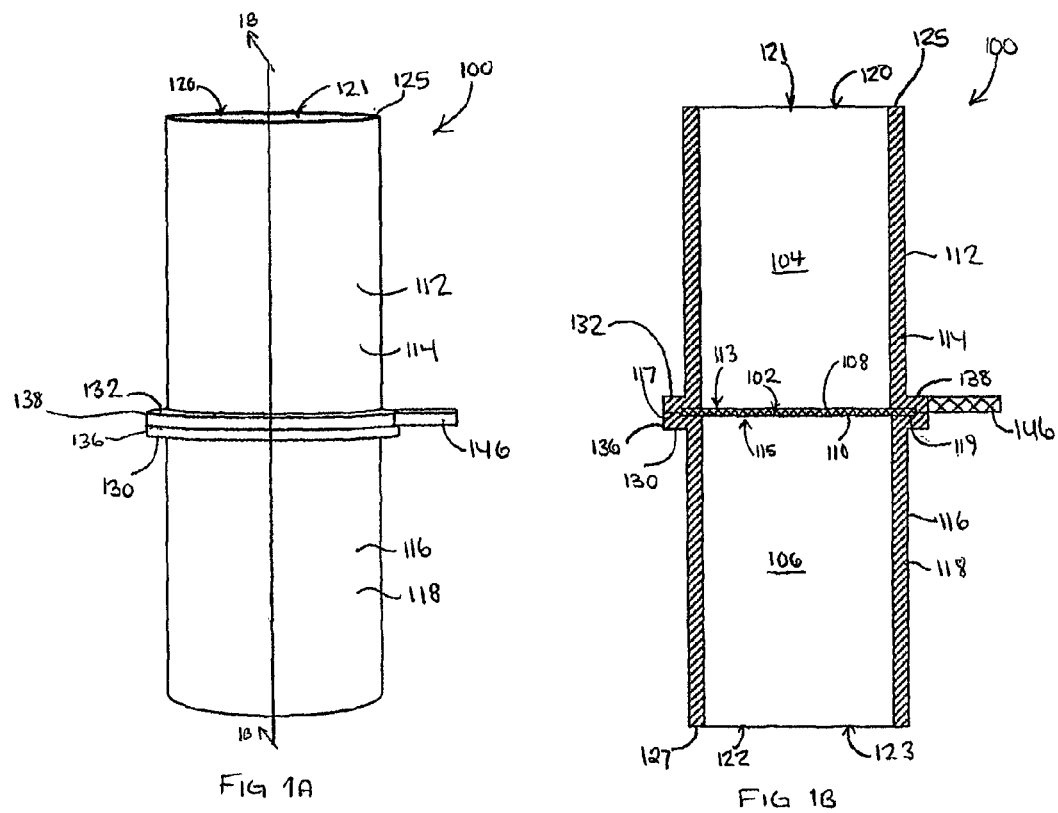
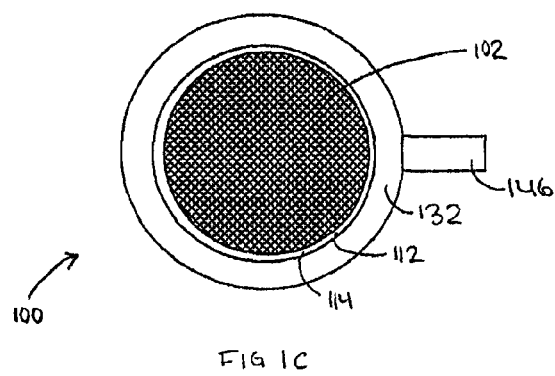

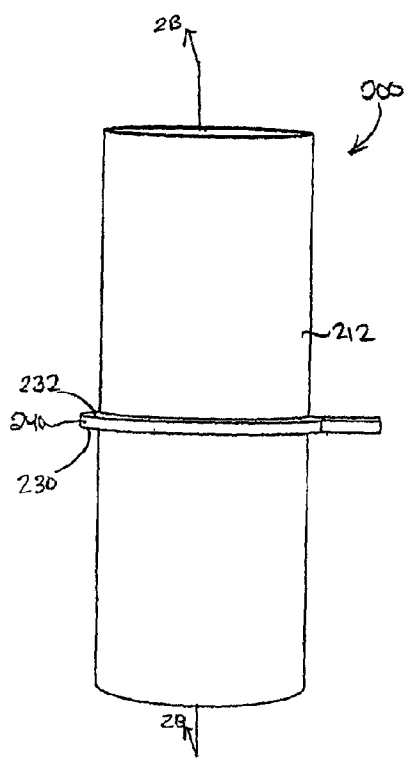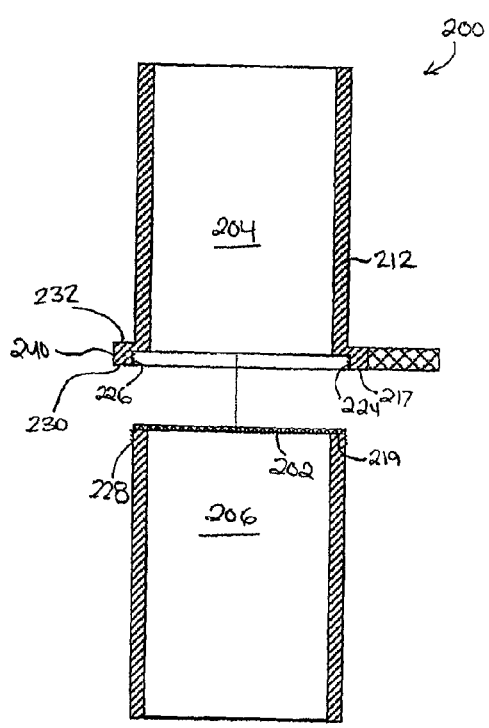
FIG 2A
FIG 2B

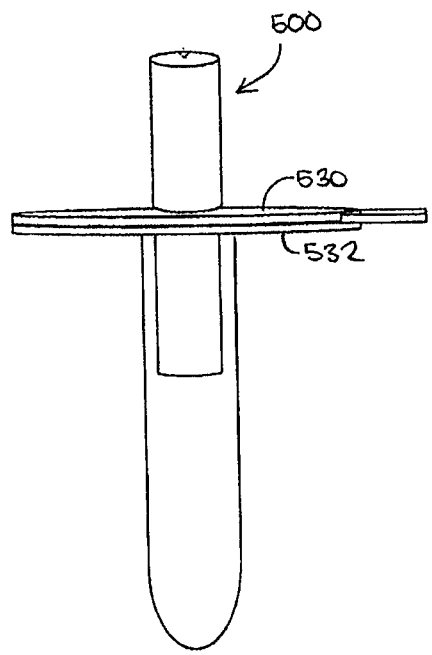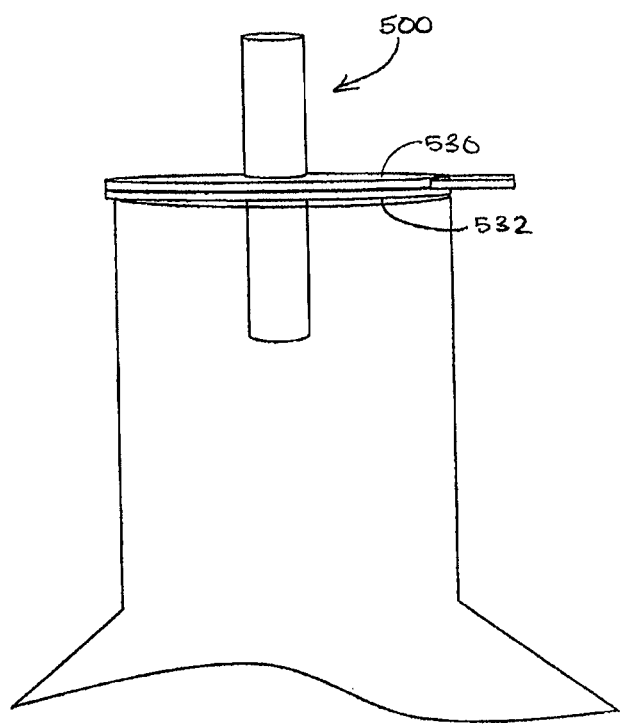
Fig. 5A
Fig 5B

Figure 13
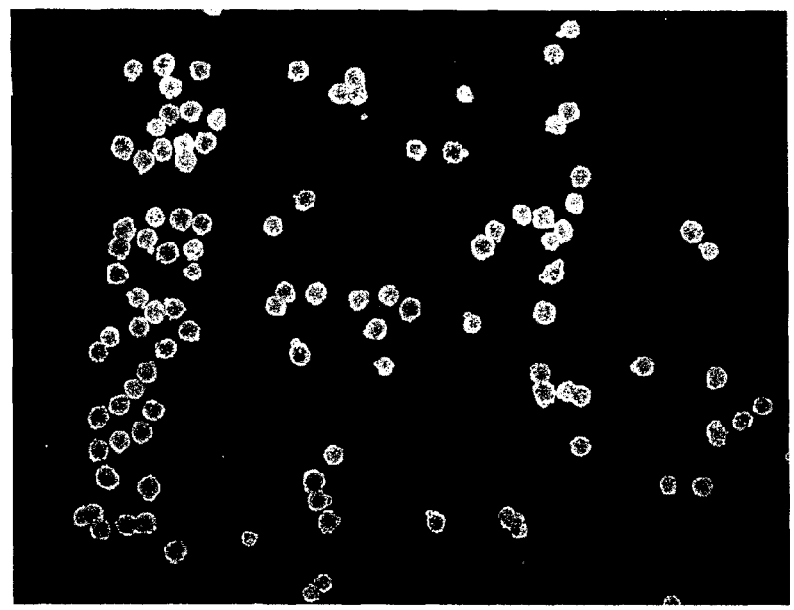
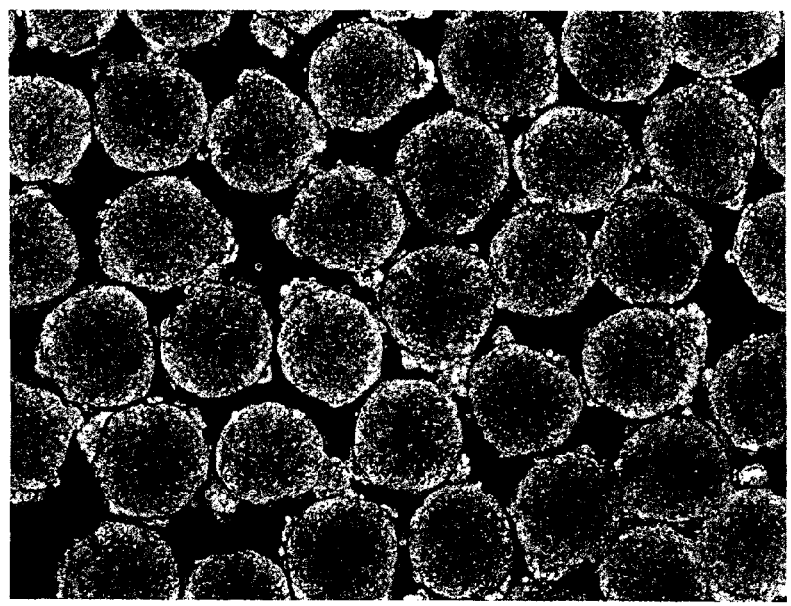

Figure 15
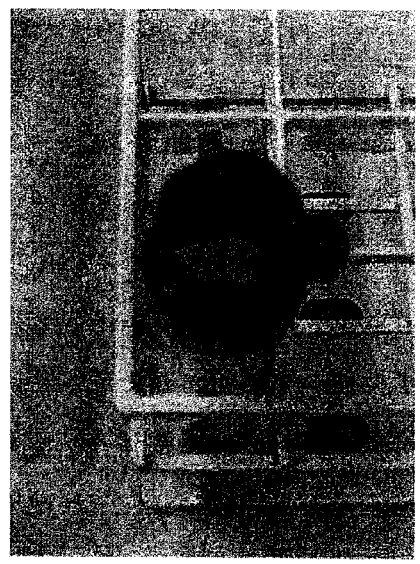

Figure 19
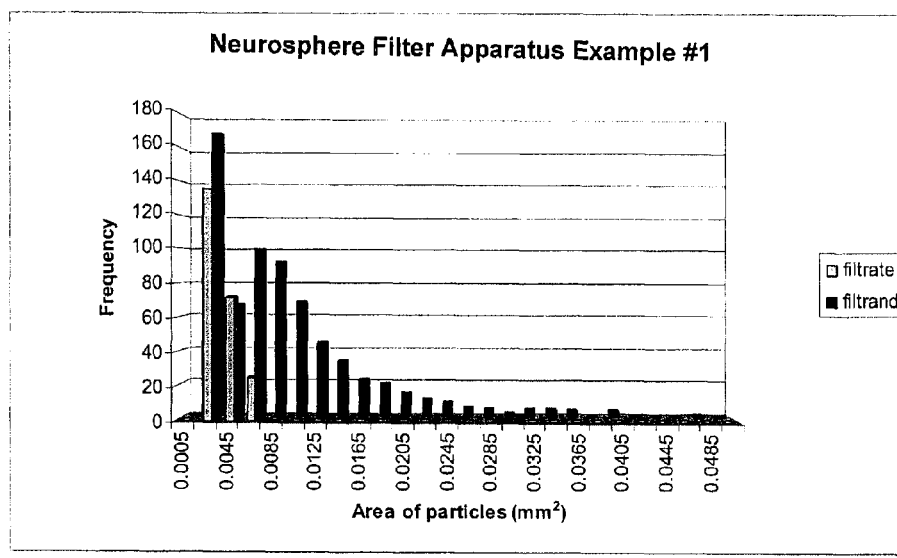
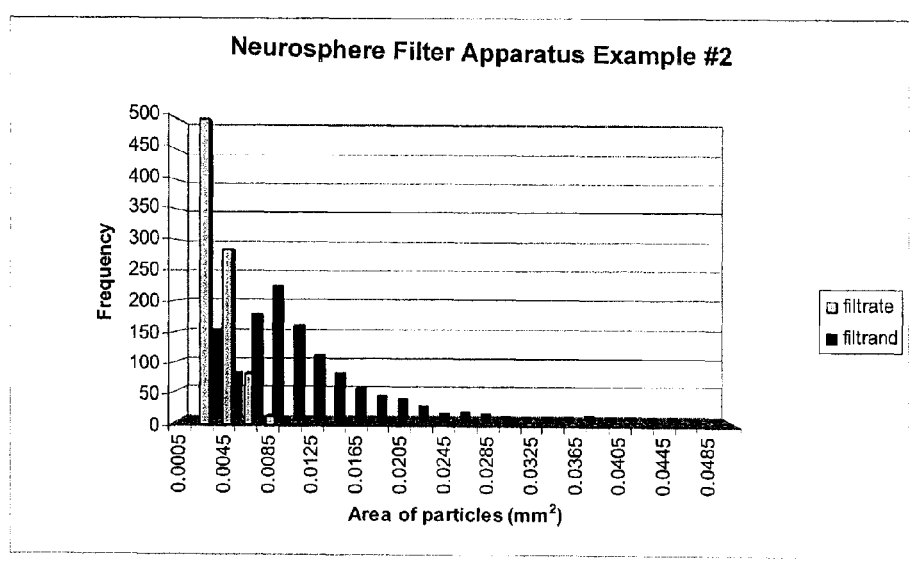

Figure 21
A 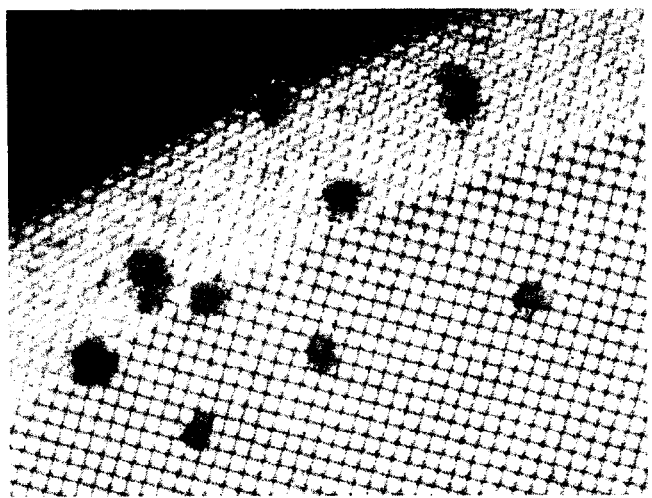
B 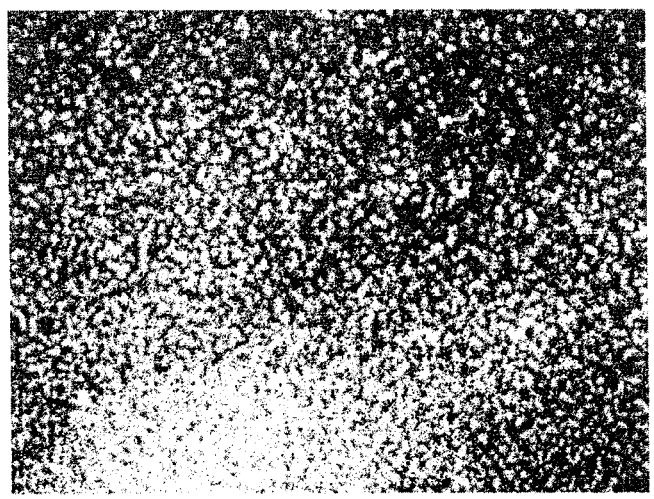
C 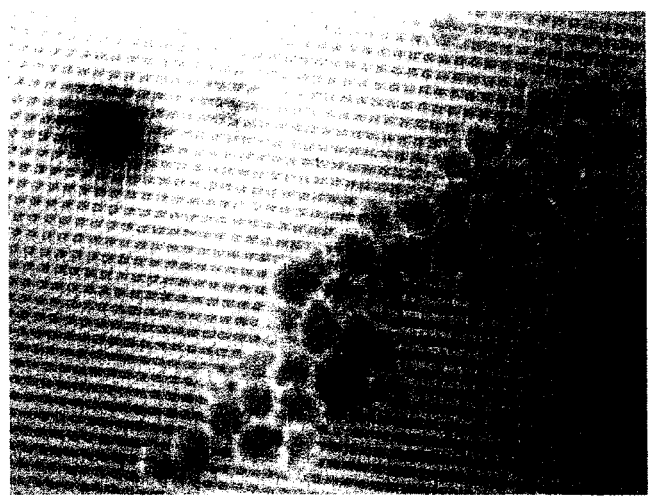

Figure 22
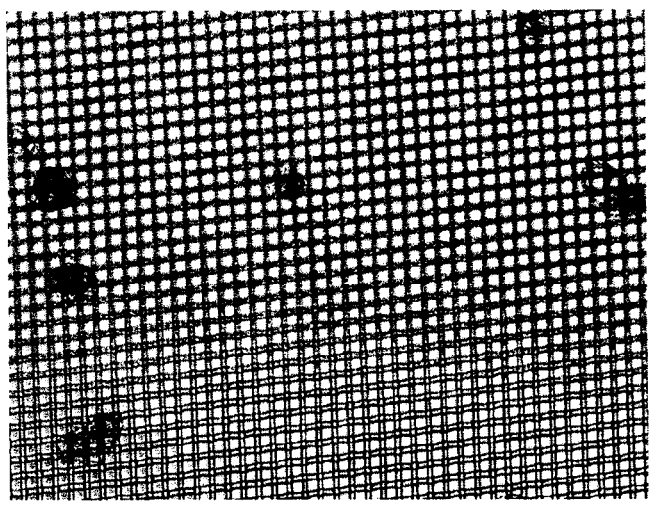
A
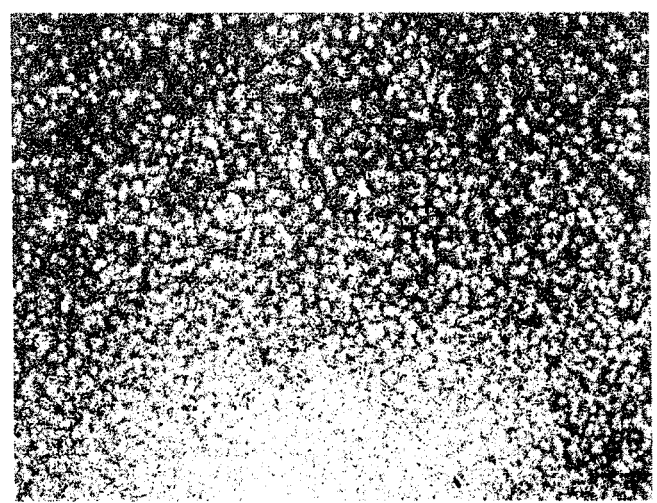
B
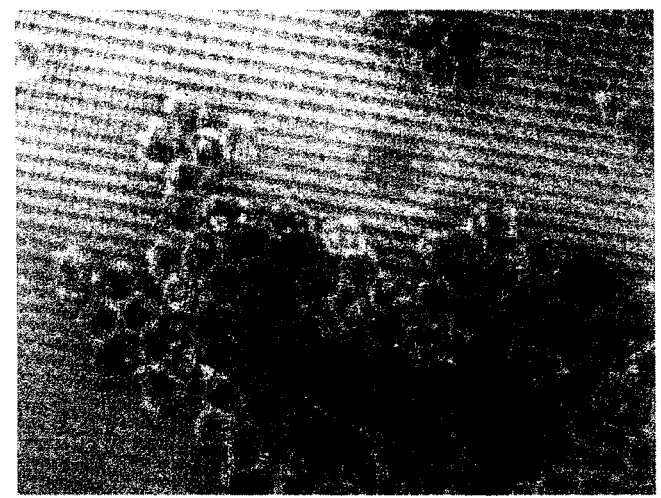
C

Figure 23
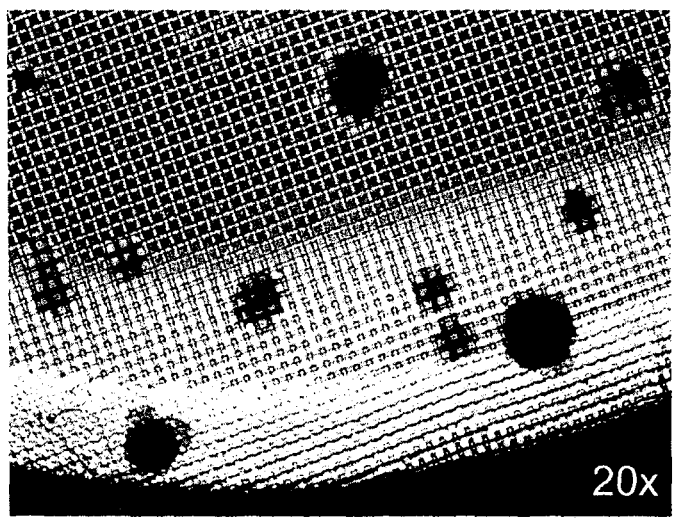
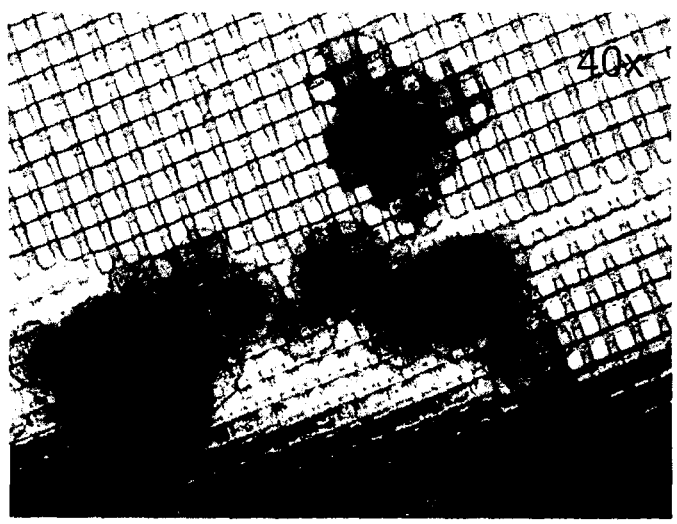

Figure 25
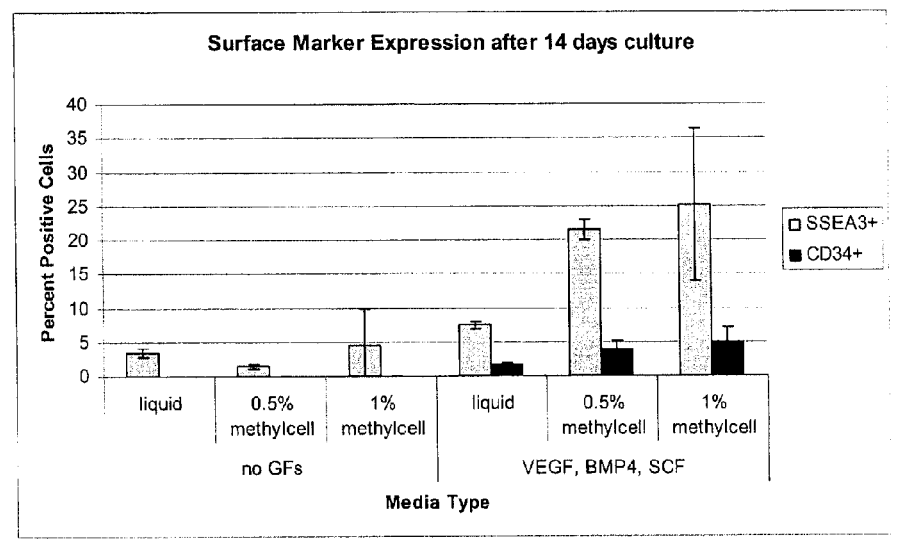
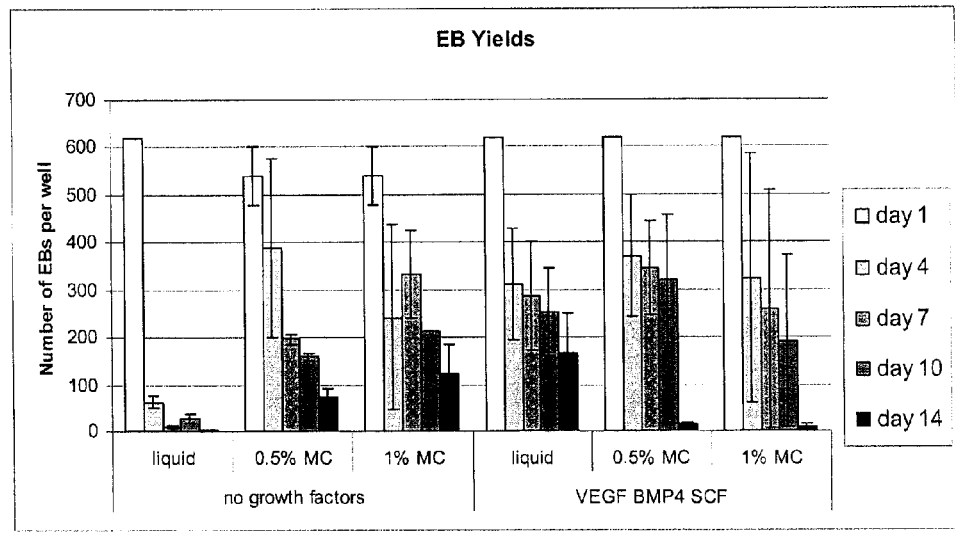

Figure 30
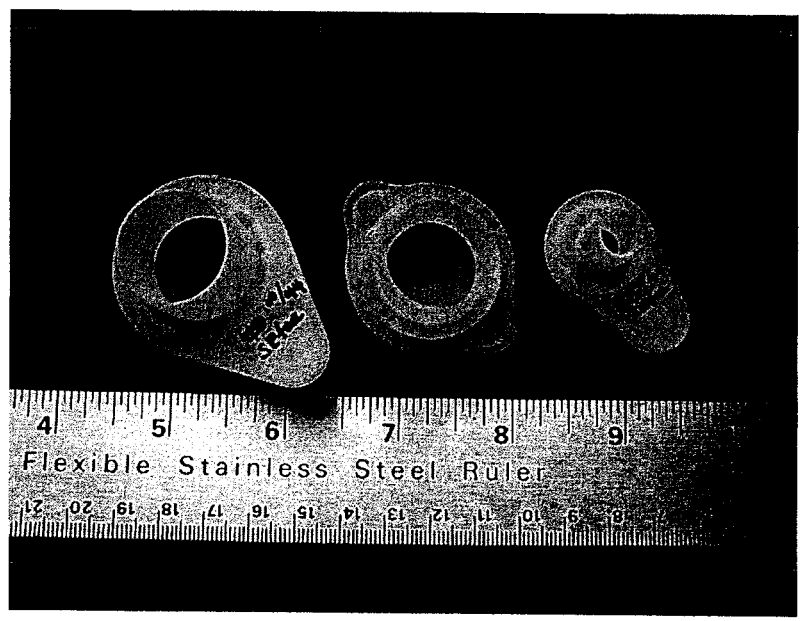
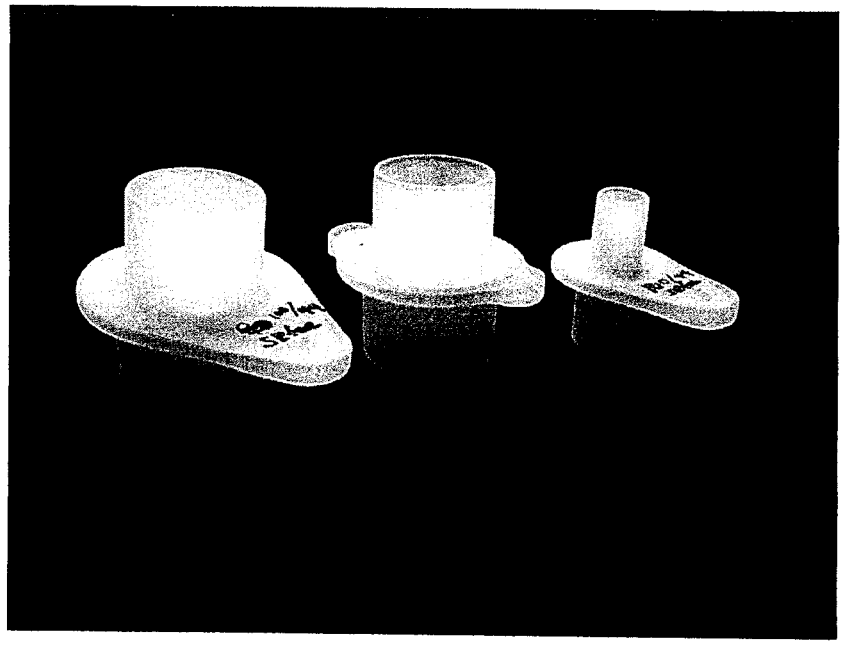

Figure 31
A
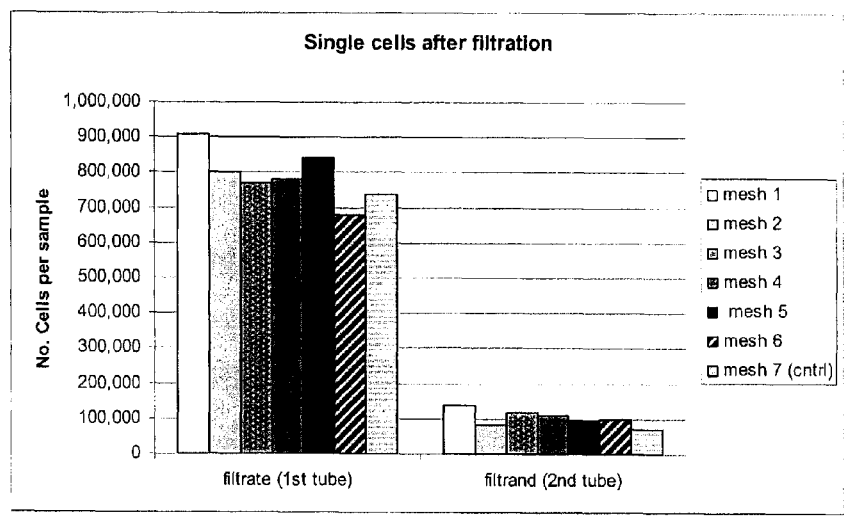
B
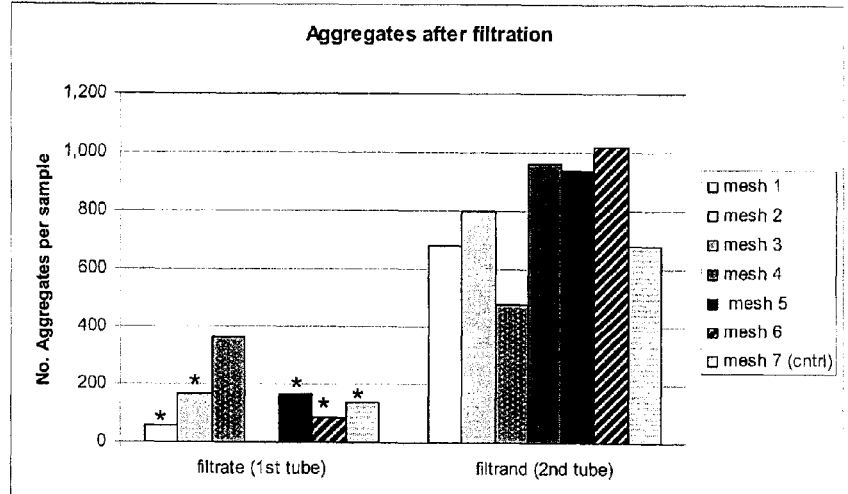
* Very small aggregates only

Figure 33
A
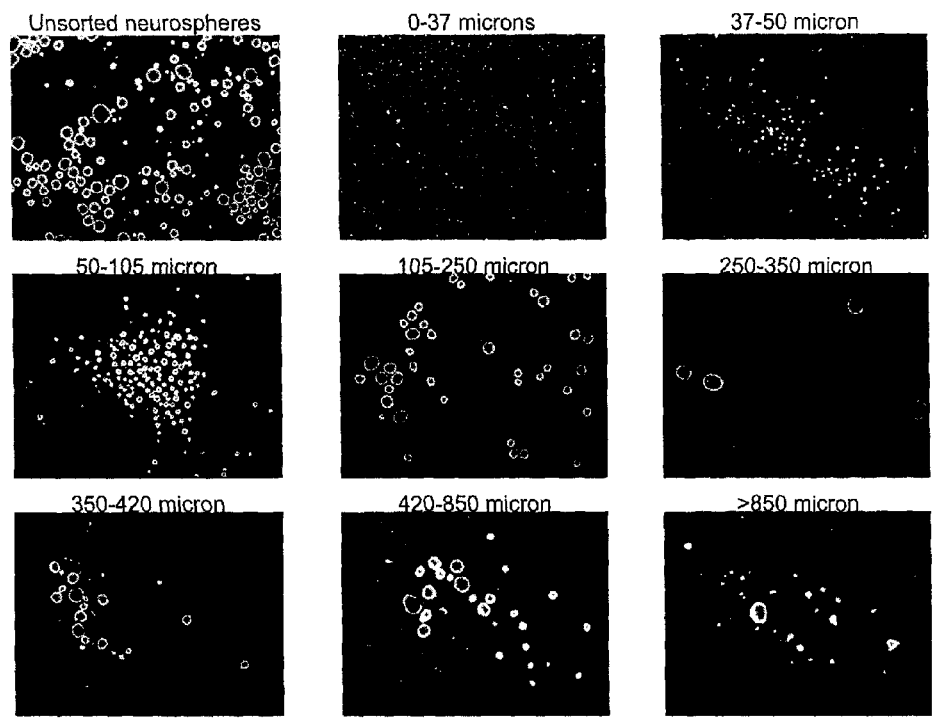
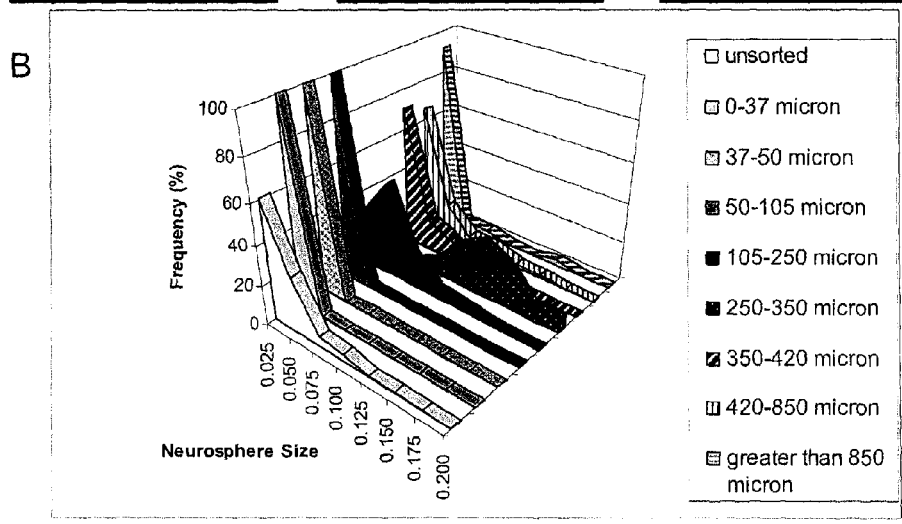

Figure 34
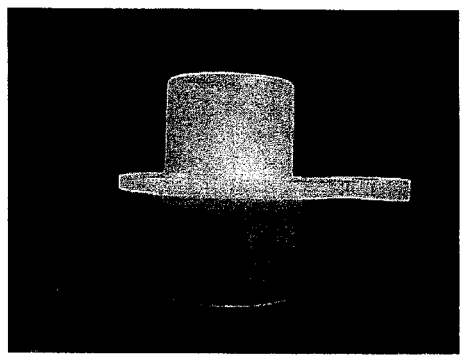
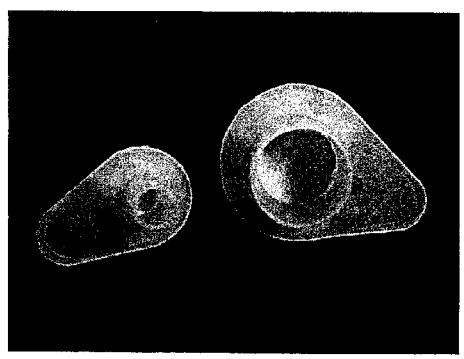
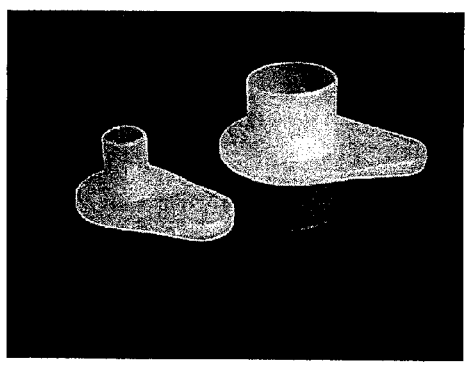

FILTER APPARATUS AND FILTER PLATE SYSTEM

CROSS-REFERENCES TO RELATED APPLICATIONS

This application claims priority from U.S. Provisional Patent Application No. 61/139,074, filed on Dec. 19, 2008, which is incorporated herein by reference in its entirety.

FIELD

The specification relates to filter apparatuses and filter plate systems. Specifically, the specification relates to filter apparatuses usable to separate and collect cellular material from a liquid, and filter plate systems usable in cell culture systems.

INTRODUCTION

The following is not an admission that anything discussed below is prior art or part of the common general knowledge of persons skilled in the art.

Many cell-based assays involve the formation of cellular aggregates, including 3D spheroids.

The usefulness of three-dimensional spheroid culture systems has been embraced in multiple fields of study [reviewed in Edelman & Keefer, Exp Neurol 192: 1-6 (2005)].

Neural stem cell biology commonly employs 3-D spheroids known as neurospheres to assay neural stem and progenitor cells in vitro [Reynolds & Weiss, Science 255: 1707-10 (1992)]. This provides a good experimental system to study factors affecting neural stem and progenitor cell proliferation and maintenance. Similarly, mammary cell biology employs the aggregates of mammary epithelial cell formation in the mammosphere culture to assay mammary stem cells in vitro [Dontu et al, Genes Dev, 17: 1253 (2003)]. Growing mammary cells in this anchorage-independent state seems to increase self-renewal of mammary stem and progenitor cells, with retention of differentiative capacity.

Three-dimensional spheroids are well established in tumor biology, where cells are cultured as multicellular tumor spheroids. Multicellular spheroids are used in studies such as tumor cell biology, therapy resistance, cell-cell interactions, invasion, drug penetration, modeling, tumor markers, nutrient gradients, tumor cell metabolism [Kunz-Schughart et al, 2004; Bates R C et al. Crit. Rev Oncol Hematol. 2000, 36(2-3):61-74]. Environmental influences have been shown to have profound effects on the neoplastic properties & pharmacological responses of tumor cells, and these effects are often only observable in three-dimensional culture systems [Weaver et al, J Cell Biol 137: 231 (1997)]

Protocols to differentiate mouse and human pluripotent stem cells including embryonic stem (ES) or induced pluripotent stem (iPS) cells into definitive tissue types commonly utilize as a first step the formation of 3-D embryoid bodies (EBs). EBs are multipotent, with the propensity to develop into cells of any of the 3 germ layers (endoderm, mesoderm or ectoderm).

Moreover, three-dimensional growth in culture has been demonstrated in a growing list of diverse tissue types, including cardiac myocytes (Akins et al., 1999, Dar et al., 2002 and Evans et al., 2003), osteoblasts (Botchwey et al., 2003, Ferrera et al., 2002, Karp et al., 2002 and Qiu et al., 2001), myoblasts (Bouten et al., 2003, Li et al., 2002 and Stegemann and Nerem, 2003), chondrocytes (Dumas et al., 2000, Hung et al., 2003 and Kisiday et al., 2002), hepatocytes (Richert et al., 2002 and Selden et al., 1999), cerebral microvascular endothelial cells (Chow et al., 2001), mesothelial and endothelial cells (Bittinger et al., 1997), cytotrophoblast cells (Thomas K. Experimental Cell Research 2004, 297: 415-423); bone marrow stromal cells (Braz. J. Med. Bio. Res. 2005, 38:1455-1462) and odontoblasts (Camps et al., 2002). Most of these studies were directed toward providing exogenously grown replacement parts for injured and aged subjects. In this approach, stem cells of the appropriate lineage would be isolated from the patient, expanded in a bio-compatible, non-immunogenic matrix, and then implanted back into the donor/patient.

The five most common approaches employed to produce 3-D cultures, include: (1) organotypic explant cultures, in which whole organs or organ elements or slices are harvested and grown on a substrate in media; (2) stationary or rotating microcarrier cultures, in which dissociated cells aggregate around porous circular or cylindrical substrates with adhesive properties; (3) micromass cultures, in which cells are pelleted and suspended in media containing appropriate amounts of nutrients and differentiation factors; (4) free cells in a rotating vessel that adhere to one another and eventually form tissue or organ-like structures (so-called rotating wall vessels or microgravity bioreactors); and (5) gel-based techniques, in which cells are embedded in a substrate, such as agarose or matrigel, that may or may not contain a scaffolding of collagen or other organic or synthetic fiber which mimics the ECM (Edlman and Keefer, Experimental Neurology 2005, 192: 1-6).

Human pluripotent stem cells (PSCs) such as embryonic stem cells and induced pluripotent stem cells are commonly cultured and passaged as aggregates. These cells have poor viability as single cells, although this can be alleviated somewhat with the addition of Y27632 Rock inhibitor to the medium. For routine passaging, it is preferable to avoid the use of Rock inhibitor, in which case the colonies are passaged from colony fractions or clumps, wherein they retain their adherence with neighboring cells and retain viability. However the size of the clumps being passaged contributes to the success of the colony, where clumps that are too large have an increased probability of spontaneous differentiation, and clumps that are too small may have reduced adhesion to the culture surface, reduced viability, and/or reduced colony maturity by the time of the next passage. It is not possible to mechanically select aggregates of the correct size, and successful PSC culture relies on the practiced skill of the researcher in breaking up the colonies to the optimal size. The ability to select aggregates of the optimal size for passaging, and remove non-viable single cells from the suspension, would improve passaging efficiency and standardize the procedure among users and among labs.

Several methods are available for the formation of mouse or human embryoid bodies (EBs) from pluripotent stem cells. Mouse EBs can be formed clonally, whereby single ES or iPS cells are placed in methylcellulose or other semi-solid media to prevent cellular migration, and the cellular progeny of a single clone will adhere together to form an EB. Alternatively, adherent ES colonies can be lifted from the tissue culture plate, usually after mild chemical dissociation and mechanical scraping, to release randomly sized clumps of cells, which when placed into non-adherent suspension culture will generate EBs. Hanging drop techniques place defined numbers of single ES cells in close proximity to each other on the underside of an inverted glass slide, thereby allowing them to aggregate into EBs [Dang et al, Biotech Bioeng, 78:442 Forced aggregation of ES cells can also be accomplished utilizing (2002) centrifugation to force defined numbers of cells into close proximity. This can be done either in a microcentrifuge tube [Kurosawa et al, J Biosci Bioeng, 96:409 (2003)], a U-bottomed microtitre plate [mouse: Koike et al, Cytotechnology, 47:3 (2005)] or human: Ng et al, Blood, 106:1601 (2005)], or a V-bottomed microtitre plate [Burridge et al, Stem Cells, 25: 929 (2007)]. These techniques efficiently promote the formation of PSC aggregates or EBs, which can then be used in differentiation protocols to generate functional mature cells.

Standard methods to harvest the 3D spheroids utilize gravity, whereby the larger spheroids or cellular aggregates will settle to the bottom of a test tube faster than the smaller and lighter single cells. The supernatant, containing single cells and particulate debris, can then be removed by aspiration or pipetting, leaving the aggregates or spheroids at the bottom of the tube.

Filtration or straining methods may be used to separate and retain single cells away from undesired clumps of tissue or other debris. For example, when a tissue or organ is harvested from an animal, it will generally be dissociated into single cells by one of several methods, such as sonication, mechanical shearing, or enzymatic digestion. The desired single cells are then commonly selected by filtering or straining the material through a nylon mesh, metal cell strainers, disposable plastic filters, filter absorbent papers or cheesecloth, and the clumps of cells or tissue which are retained in the separation or filtration system are discarded.

U.S. Pat. No. 5,593,587 describes a cell strainer device and method of use, whereby the cell and tissue suspension is placed in a reservoir supported on top of a 50 mL test tube. The device has 40-100 micron mesh as exterior and bottom walls, which allow the single cells to pass through into the test tube by gravity, while retaining the tissue clumps in the reservoir. Similarly, U.S. Pat. No. 5,711,875 describes a device for filtering single cells into a 5 ml test tube for use in flow cytometry studies, whereby the cellular aggregates are retained in the cap and discarded. Finally, Millipore Steri-flip catalogue no. SCNY00040 contains a 40 μm nylon mesh and utilizes vacuum filtration to strain and retain single cells from a cell and tissue suspension.

Other methods for isolating cell aggregates, spheroids or EB involve non-filtration based methods such as sorting of cell clumps by the COPAS Instrument from Union Biometrica.

Following aggregate formation, the aggregates, for example EBs derived from human PSCs, are commonly cultured in a liquid suspension culture for a period of up to 1 month. During this time, aggregates must be kept separated from each other or they will have a tendency to amalgamate together. Keeping the aggregates at low density alleviates this problem somewhat, but cannot completely prevent the aggregates from coming into physical contact with one another. Even the small shaking of the culture due to the running of the incubator can create a wave motion that forces aggregates, cells and other particles in a liquid suspension culture into the center of a circular culture vessel. Physically separating the aggregates into individual wells of a multi-well plate alleviates this problem, but is time consuming and inefficient. To plate aggregates into individual wells, they can be suspended at a low density and then plated out so that the probability of having more than one aggregate in a defined volume (equal to the volume of one well) is very low. However, this leads to multiple wells with zero aggregates, as well as a small number of wells with 2 or more aggregates.

Aggregates or spheroid cultures can be maintained in liquid culture for a period of up to several months depending on the cell type. During these extended culture periods, fresh liquid media needs to be replaced every 1-7 days depending on the cell type and the stability of the media components. Media changes are customarily accomplished using gravity or centrifugation to separate out the larger, heavier spheroids from single cells and liquid media. The entire contents of the culture vessel are washed out, the spheroids are allowed to sink to the bottom of the test tube, the supernatant is removed, and the spheroid-containing pellet is recovered. The spheroids can then be resuspended in fresh liquid medium, replated into a culture vessel, and finally returned to the incubator.

Many spheroid cultures also require the addition of specific factors within the liquid media, and these will need to be replaced or changed routinely. A variety of factors are commonly added to induce cellular aggregate proliferation, growth, and/or differentiation. These include growth factors, chemokines, peptides, and signaling molecules. These can be used to supplement media throughout a culture period, or they may be required in a specific sequence. For example, undifferentiated hES cells or EBs may need to be induced first toward a specific germ layer fate (ie. endodermal, mesodermal, or ectodermal). Subsequently, the germ layer-specified cells can then be induced toward a specific tissue type (eg. endodermal cells toward the pancreatic lineage). Finally, the tissue-specified cells can be induced with a distinct cocktail of inducing factors to become specific end stage cells (eg. pancreatic cells to insulin-producing beta-cells). In addition, there may be some survival or growth-promoting factors which need to be added through a large portion of the culture period. The specific components and sequential timing of factor supplementations are continually being worked out and improved for every type of aggregate culture. In all cases where the removal and addition of factors is required, aggregates must be washed and resuspended in fresh media, preferably with minimal disruption or disturbance.

Filter plates are commonly used in tissue culture for a multitude of applications, including screening protein libraries for chemotaxis, invasion and other cellular activities. United States Patent Application Publication No. 2006/0286003 describes a filter plate device which includes a multi-well plate with a filter/membrane bottom, that fits inside of a collection plate. The filter plate can therefore be immersed in the assay tray, and cells can move across the membrane in response to a concentration gradient of a given protein. These filter plates typically have membrane diameters on the order of 0.1-5 μm, allowing proteins or single cells to migrate through.

SUMMARY

The following summary is provided to introduce the reader to the more detailed discussion to follow. The summary is not intended to limit or define the claims.

Using gravity to separate cellular aggregates from the surrounding milieu of non-aggregated single cells, particulate matter, and liquids can be slow and inefficient. Aggregates initially at the top of the tube will take longer to sink to the bottom than those initially closer to the bottom, and may be lost. Similarly, many single cells will also fall to the bottom of the tube and be included in the aggregate pellet. Light centrifugation may be employed to assist the recovery of aggregates, however this will also result in decreased purity due to contaminating co-recovery of single cells. Moreover, forcing the aggregates into close proximity during the separation procedure (especially if centrifugation is used) can cause the undesirable aggregation of multiple aggregates together, resulting in fold to log increases in size.

Furthermore, using known devices and methods involving filtration do not allow collection of both the filtrate and the filtrand. Rather, the single cells are retained for further use, and the "impurities", including cellular aggregates, are discarded.

The present disclosure provides a device and method for the collection of cellular aggregates from the surrounding milieu of non-aggregated single cells, particulate matter, and liquids. Further, examples of the present disclosure simultaneously separate single unit of particles using straining or filtration methods and in the same process retain doublets, triplets or larger forms of aggregates of said particles in the same system.

According to one broad aspect, a filter apparatus is provided. The filter apparatus comprises a filter having first and second opposed surfaces. A first reservoir is positioned adjacent the first surface and in communication with the first surface, and a first inlet-outlet port is in communication with the first reservoir and spaced from the first surface. A second reservoir is positioned adjacent the second surface, and in communication with the second surface, and a second inlet-outlet port is in communication with the second reservoir and spaced from the second surface.

By providing a reservoir on either side of the filter, fluid can be passed through the filter from either side thereof. Accordingly, a fluid containing solids may be provided to one of the reservoirs, and may be allowed to pass through the filter. The filter apparatus may then be inverted, and fluid may be provided to the other of the reservoirs, in order to wash the solids off of the filter. Accordingly, the fluid and the solids may be easily collected.

In some examples, the first reservoir is defined by a least a first sidewall extending outwardly from the first surface; and the second reservoir is defined by a second sidewall extending outwardly from the second surface. The first sidewall may have a first inner face, the second sidewall may have a second inner face, and the membrane may be secured between the first and second inner faces.

In some examples, the filter apparatus further comprises a first seating surface seatable on a rim of a fluid vessel to couple the filter apparatus to the fluid vessel. When the first seating surface is seated on the rim of the fluid vessel, the first opening is positioned within the fluid vessel, and the second opening is positioned above the fluid vessel.

In some examples, the filter apparatus further comprises a second seating surface seatable on the rim of the fluid vessel to couple the filter apparatus to the fluid vessel. When the second seating surface is seated on the rim of the fluid vessel, the second opening is positioned within the fluid vessel, and the first opening is positioned above the fluid vessel.

In some examples, the first seating surface is provided by a first flange, and the second seating surface is provided by a second flange. The first flange may be integral with the second sidewall, and the second flange may be integral with the first sidewall.

In some examples, the first seating surface is provided by a first stepped portion of the first sidewall, and the second seating surface is provided by a second stepped portion of the second sidewall.

In some examples, the filter apparatus further comprises a handle coupled to one of the first sidewall and the second sidewall.

In some examples, the first sidewall extends substantially perpendicularly to the first surface, and the second sidewall extends substantially perpendicularly to the second surface.

In some examples, the filter membrane is fabricated from a material selected from the group consisting nylon, polypropylene, polyethylene, polyester, polyetheretherketone, polytetrafluoroethyline, polyfluoroethylenepropylene, polyvinyls, polysulfone, polyvinyl fluoride, polychlorotrifluoroethylene, ethylene tetrafluoroethylene, aluminum, bass, copper, nickel, bronze, steel, stainless steel and titanium.

In some examples, the filter apparatus comprises an additional filter extending across the first opening. The additional filter may have a first additional filter surface facing the first reservoir, and an opposed second additional filter surface. A third reservoir may be provided adjacent and in communication with the first additional filter surface. The third reservoir may have a third inlet-outlet port spaced from first additional filter surface.

In some examples, the second reservoir is separable into two reservoir portions.

In some examples the first reservoir is removably positioned adjacent the first surface, and the second reservoir is removably positioned adjacent the second surface.

According to another broad aspect, a method of separating at least a first population of target entities from a volume of fluid is provided. The first population of target entities has an average diameter. The method comprises providing a filter apparatus comprising a filter membrane having first and second opposed surfaces, the filter membrane having a pore size less than the first average diameter, a first reservoir adjacent and in communication with the first surface; and a second reservoir adjacent and in communication with the second surface. The method further comprises positioning the second reservoir in communication with a first fluid vessel, and first reservoir above the second reservoir; providing the volume of fluid to the first reservoir and allowing the first volume of fluid to pass through the filter membrane and into the first fluid vessel while retaining at least some of the second population of target entities on the first surface; positioning the first reservoir in communication with a second fluid vessel, and the second reservoir above the first reservoir; and providing a second volume of fluid to the first reservoir and allowing the second volume of fluid to pass through the filter membrane and wash the second population of target entities into the second fluid vessel.

In some examples, the first population of target entities comprises three-dimensional cellular aggregates. The cellular aggregates may include embryoid bodies, tumour spheroids, neurospheres, and/or mammospheres.

Known methods for purifying entities such as cells, cellular aggregates or spheroids from old media while the aggregates are in culture are inefficient, do not allow rapid replacement with fresh media, and result in disturbance to the entities. Methods which use centrifugal force result in decreased purity, and can lead to merging together of multiple aggregates. Moreover, it is too time consuming to be used in high-throughput applications.

Examples disclosed herein provide a device and method which allow for efficient and rapid replacement of culture media, while minimizing disturbance to aggregates.

According to one broad aspect, a filter plate system is disclosed. The filter plate system comprises a reservoir plate. The reservoir plate comprises at least one reservoir well. The filter plate system further comprises a strainer plate. The strainer plate comprises at least one strainer well, which is removably receivable in the reservoir well. The strainer well comprises at least one mesh wall portion.

In some examples, the reservoir plate comprises a plurality of reservoir wells, the strainer plate comprises a plurality of strainer wells, each strainer well is positionable in one of the reservoir wells, and each strainer well comprises at least one mesh wall portion.

In some examples, the reservoir plate comprises a plurality of reservoir wells, the strainer plate comprises one strainer well, and strainer well is positionable in one of the reservoir wells.

In some examples, each reservoir well is defined by a reservoir well sidewall and a reservoir well base wall.

In some examples, each strainer well is defined by a strainer well sidewall and a strainer well base wall. Each strainer well base wall can comprise the mesh wall portion.

In some examples, the filter plate system further comprises a lid mountable to the reservoir plate to seal the strainer plate within the reservoir plate.

In some examples, the reservoir plate, the strainer plate, and the lid are fabricated from polystyrene.

In some examples, the pore size of the mesh is between about 10 microns and about 100 microns.

In some examples, the mesh is fabricated from a material selected from the group consisting of nylon, polypropylene, polyethylene, polyester, polyetheretherketone, polytetrafluoroethyline, polyfluoroethylenepropylene, polyvinyls, polysulfone, polyvinyl fluoride, polychlorotrifluoroethylene, ethylene tetrafluoroethylene, aluminum, bass, copper, nickel, bronze, steel, stainless steel and titanium.

According to another broad aspect, a method of separating a target population from a volume of liquid media is provided. The method comprises providing a filter apparatus, the filter apparatus comprising: a reservoir plate, the reservoir plate comprising at least one reservoir well, and a strainer plate, the strainer plate comprising at least one strainer well, the strainer well positioned in the reservoir well, the strainer well comprising at least one mesh wall portion, the pore size of the mesh wall portion being less than the average diameter of the cell population. The method further comprises providing the target population and the volume of liquid media to the at least one strainer well; and removing the strainer well from the reservoir well.

In some examples, the method further comprises removing the volume of liquid media from the reservoir well, providing a second volume of liquid media to the reservoir well, and positioning the strainer well in the reservoir well.

In some examples, the target population comprises at least one cell type selected from the group consisting of mammalian cells, stem cells, human ES cells, and tumor cells. In some examples, the target population can comprises at least one aggregate of cells selected from the group consisting of aggregates of mammalian cells, aggregates of stem cells, human ES cell aggregates, and tumor spheroids.

DRAWINGS

FIG. 1A is a perspective view of an example of a filter apparatus;

FIG. 1B is a cross section taken along line 1B-1B in FIG. 1A;

FIG. 1C is a top view of the filter apparatus of FIG. 1A;

FIG. 2A is a perspective view of an alternate example of a filter apparatus;

FIG. 2B is a cross section taken along line 2B-2B in FIG. 2A;

FIG. 5A is a perspective view of an alternate example of a filter apparatus, showing the filter apparatus coupled to an alternate fluid vessel;

FIG. 5B is a perspective view of the filter apparatus of FIG. 5A, showing the filter apparatus coupled to another alternate fluid vessel;

FIG. 13 shows EBs formed via forced aggregation in AggreWell plate, and filtered through cell strainer to remove single cells. Top: 20× magnification, bottom: 100× magnification;

FIG. 15 is a series of photographs of a prototype-1 filter apparatus with solid side walls

Figure 17:
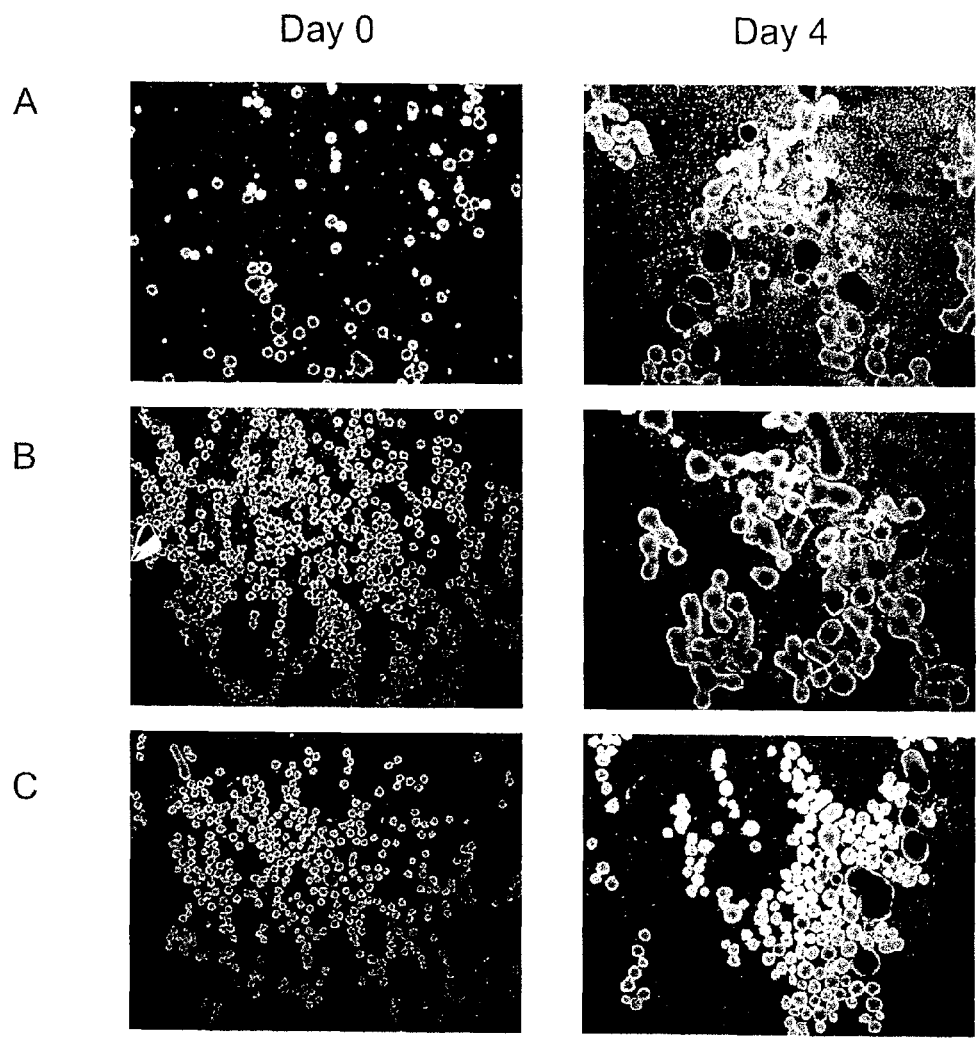

FIG. 17 shows cultures of EBs grown in modified mTeSR liquid media. A) modified mTeSR medium 'A', B) modified mTeSR medium 'B', C) modified mTeSR medium 'C'. All photos at 20× magnification.

Figure 18:
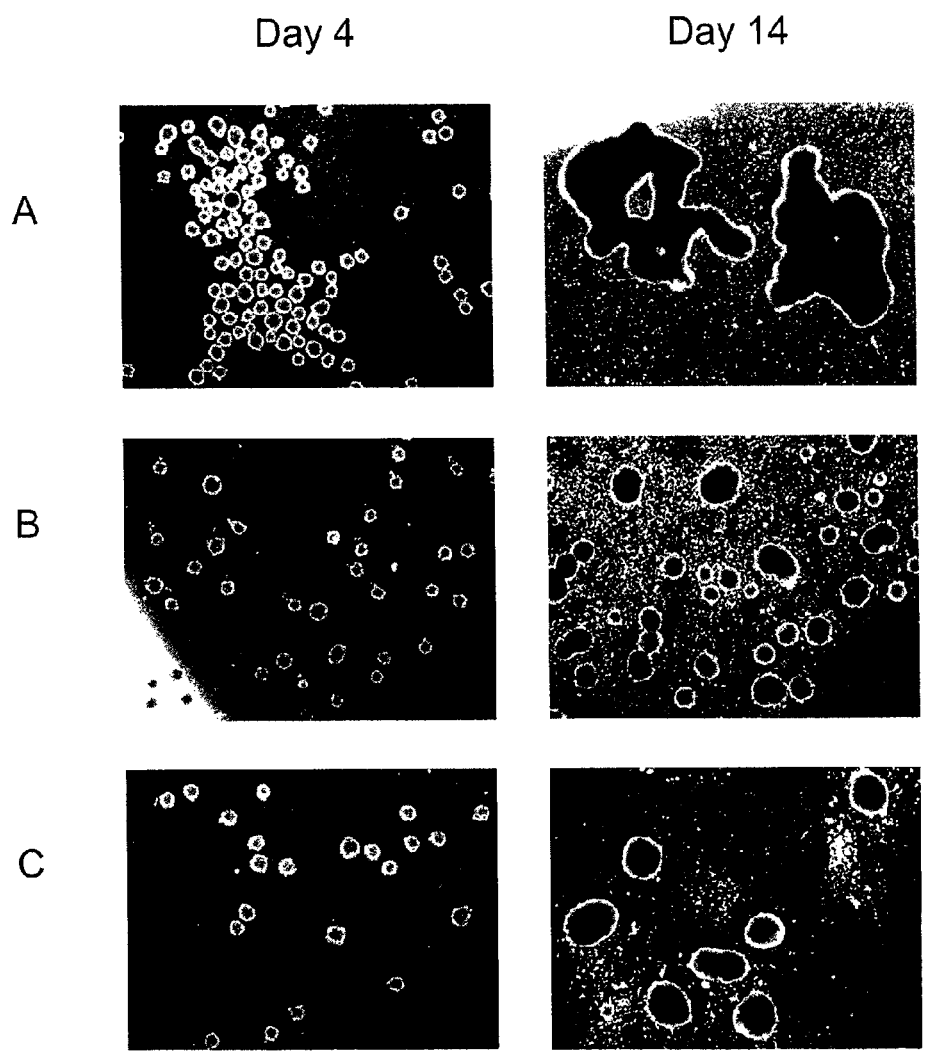

FIG. 18 shows cultures of EBs in liquid or methylcellulose based modified mTeSR 'A' medium without added growth factors. A) in liquid culture, multiple EBs adhere together over time, so that by the end of the 14 day culture period there remains only very few but large EBs. The addition of 0.5% (B) or 1.0% (C) methylcellulose prevents physical contact between EBs, allowing them to remain individual. All photos at 20× magnification FIG. 19 shows different sized neurospheres separated in the first (filtrate) or second fraction (filtrand) using a prototype filter apparatus with 40 µm diameter opening. The majority of neurospheres from the filtrate fraction are less than 0.0085 mm$^2$ in area, whereas many neurospheres from the filtrand fraction are larger in area, with a peak frequency at 0.009 mm$^2$ in area.

Figure 20:
Figure 24:
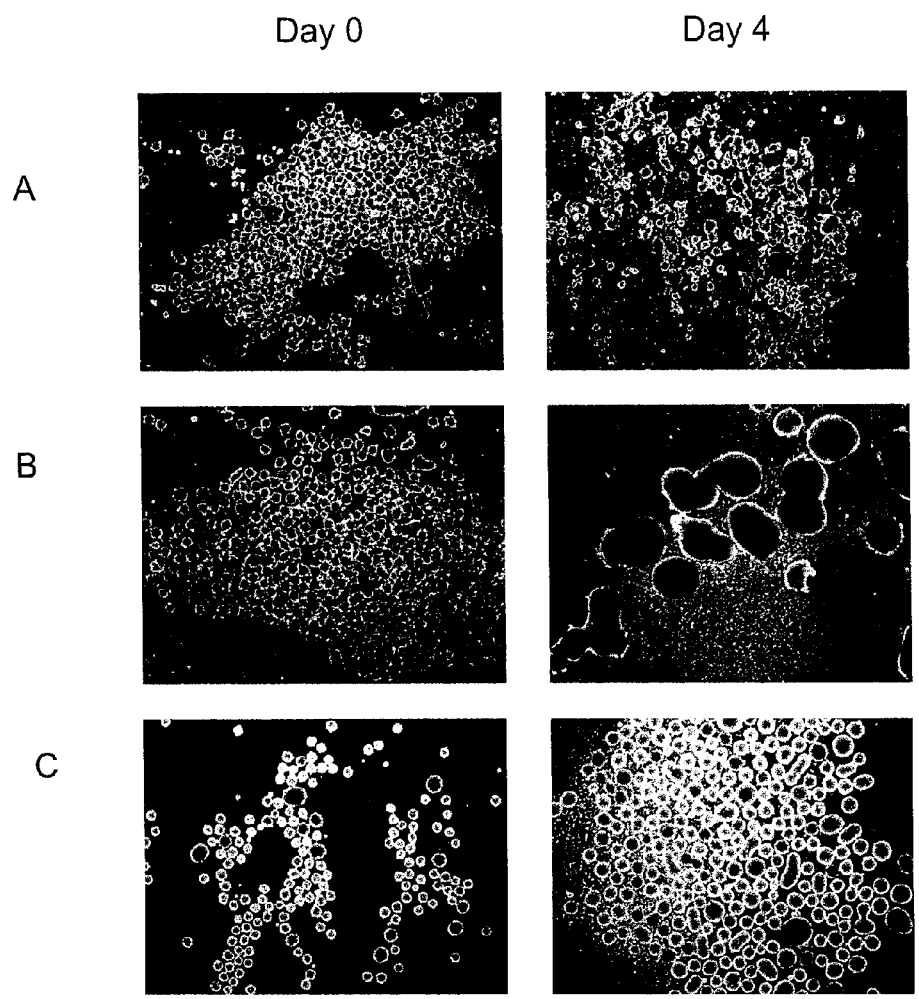
Figure 26A:
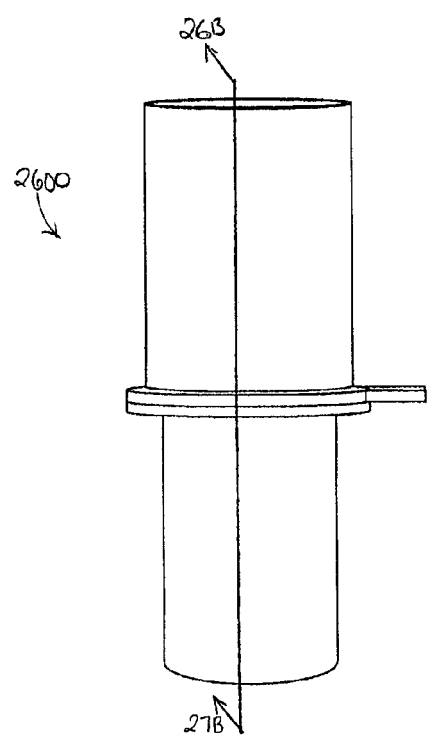
Figure 26B:
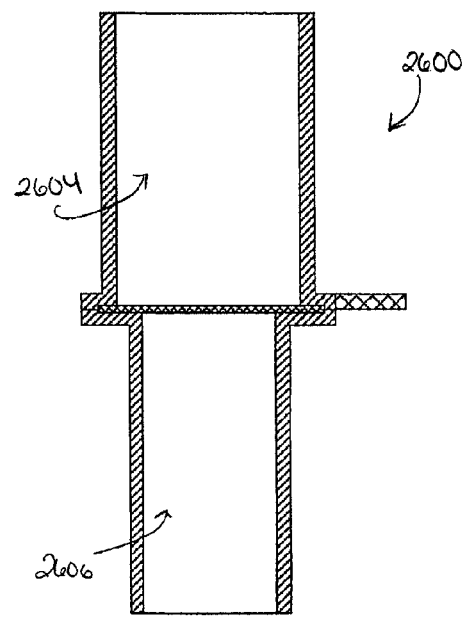
Figure 26C:
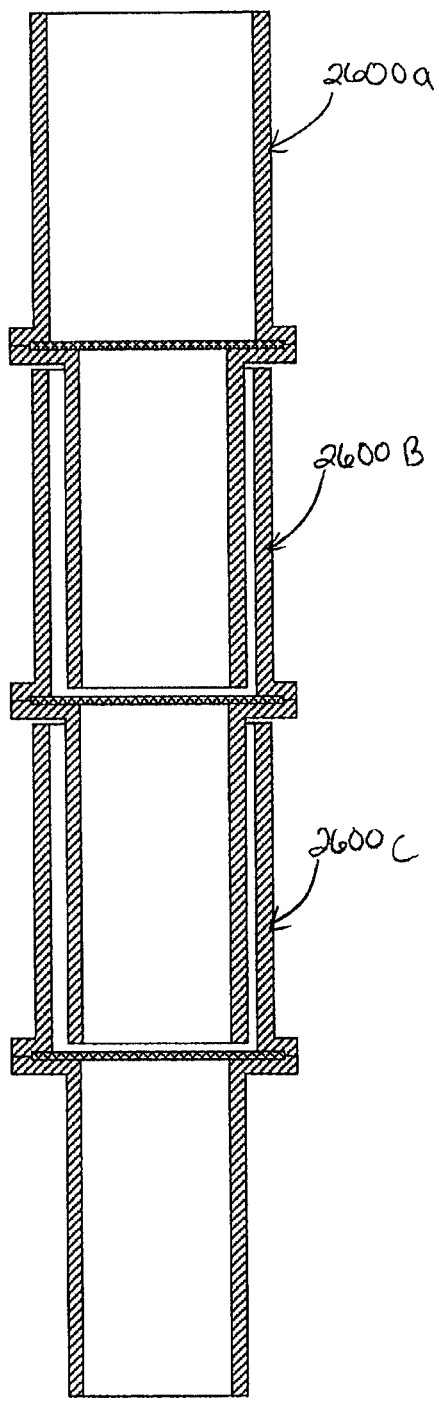
Figure 27A:
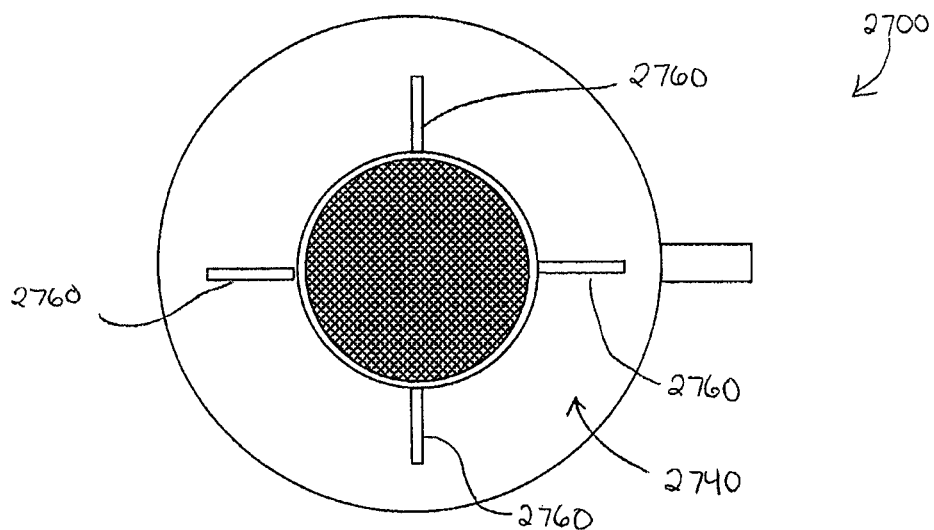
Figure 27B:
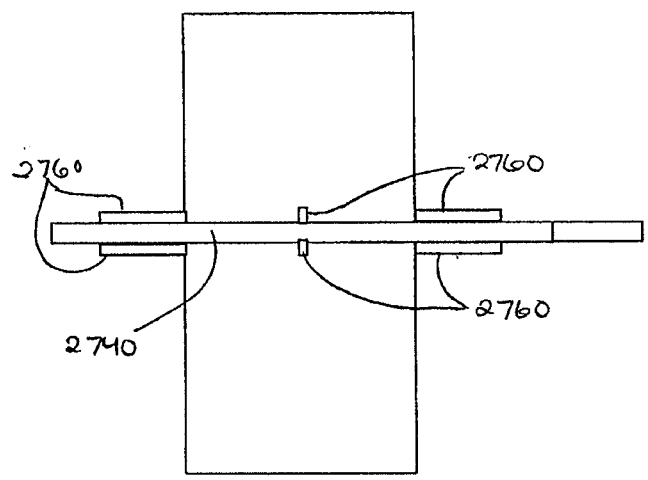
Figures 28A, 28B:
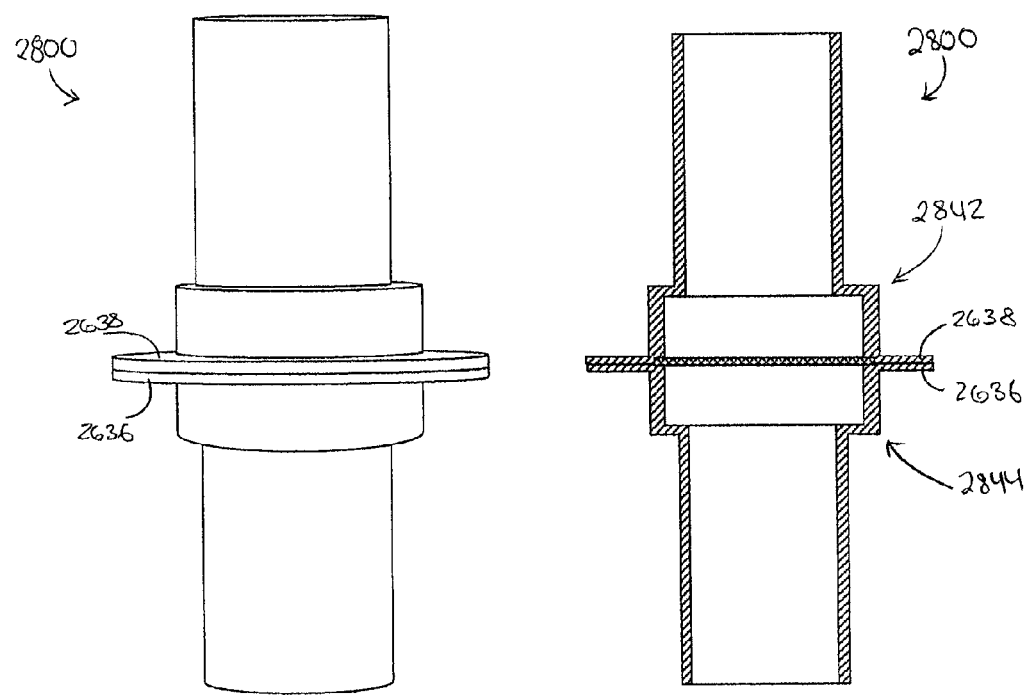
Figures 29A, 29B:
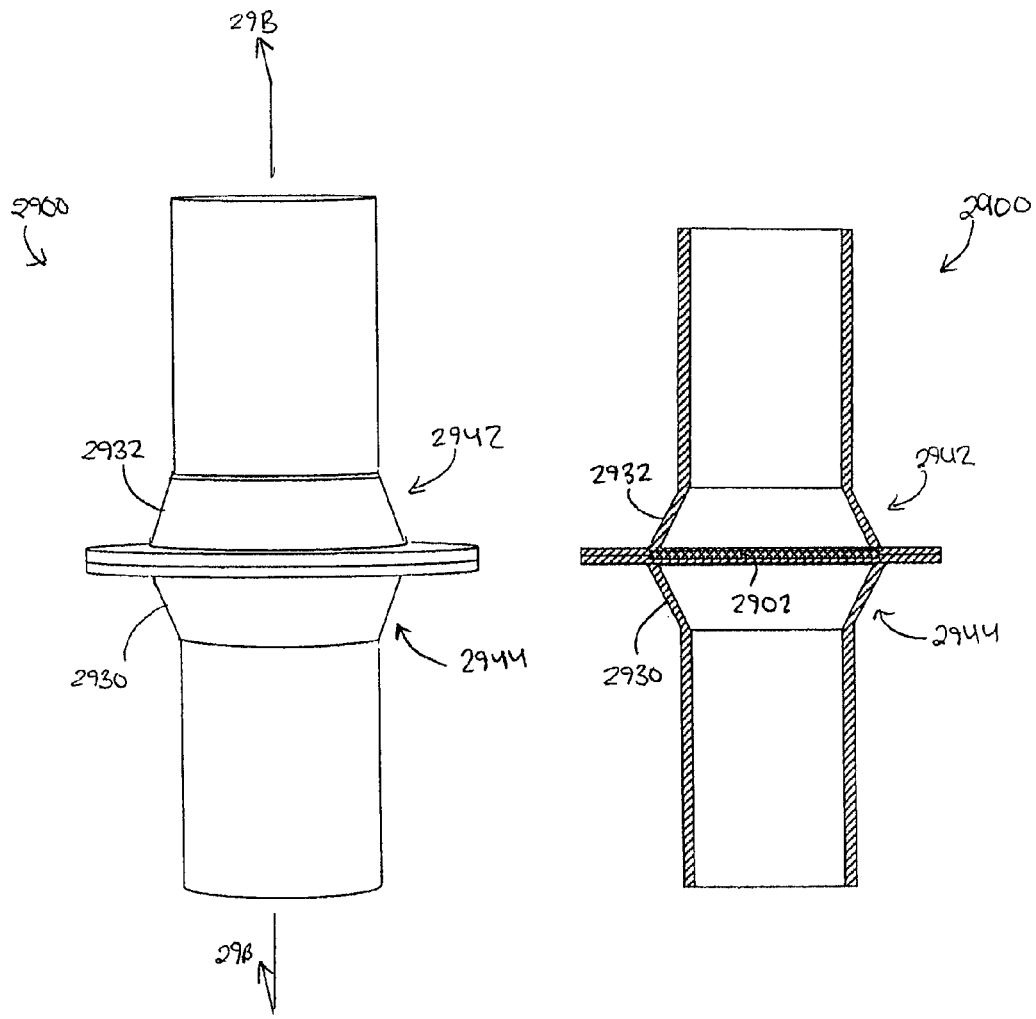

FIG. 20 is a series of photographs of a prototype filter plate system;

FIG. 21 shows EBs grown in liquid media without growth factor supplementation in a protoype filter plate system. A) before media change, EBs sitting atop the strainer (40×) B) after media change, single cells and small particles left behind in well (40×) C) after media change, EBs transferred to fresh media (left 40×, right 100×);

FIG. 22 shows EBs grown in liquid media supplemented with 50 ng/ml VEGF, 40 ng/ml SCF and 40 ng/ml BMP-4 in prototype filter plate system. A) before media change, EBs sitting atop the mesh (40×) B) after media change, single cells and small particles left behind in well (40×) C) after media change, EBs transferred to fresh media (left 40×, right 100×);

FIG. 23 shows EBs growing inside prototype filter plate system in media containing 0.5% methylcellulose;

FIG. 24 shows growth of Aggrewell™-generated EBs in various liquid medias. A) DMEM/F12 with 20% FBS, B) X-Vivo10, C) AggreWell™ Medium. All photos at 20× magnification;

FIG. 25 shows A) EB yields during 14 day culture in liquid or methylcellulose based modified mTeSR "A" media with or without the addition of growth factors VEGF, BMP4 and SCF. B) Expression of surface markers for undifferentiated cells (SSEA3) and hematopoeitic cells (CD34) after 14 days EB culture in media with or without growth factors;

FIG. 26A is a perspective view of an alternate example of a filter apparatus;

FIG. 26B is a cross section taken along line 26B-26B in FIG. 26A;

FIG. 26C is a cross section taken along line 26B-26B in FIG. 26A, showing a plurality of filter apparatuses in a stacked configuration;

FIG. 27A is a top view of an alternate example of a filter apparatus;

FIG. 27B is a side view of the filter apparatus of FIG. 27A;

FIG. 28A is a perspective view of an alternate example of a filter apparatus;

FIG. 28B is a cross section taken along line 28B-28B in FIG. 28A;

FIG. 29A is a perspective view of an alternate example of a filter apparatus; and FIG. 29B is a cross section taken along line 29B-29B in FIG. 29A.

Figure 32:
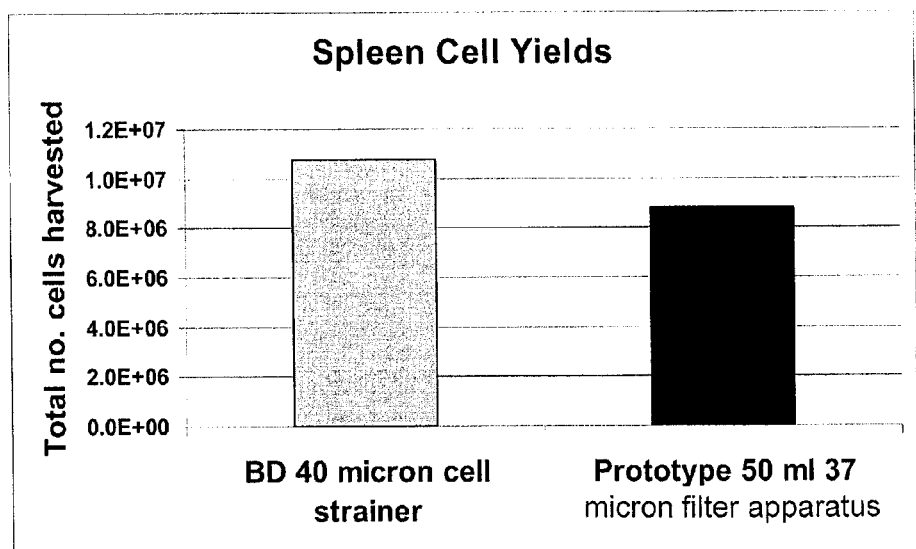
Figure 35:
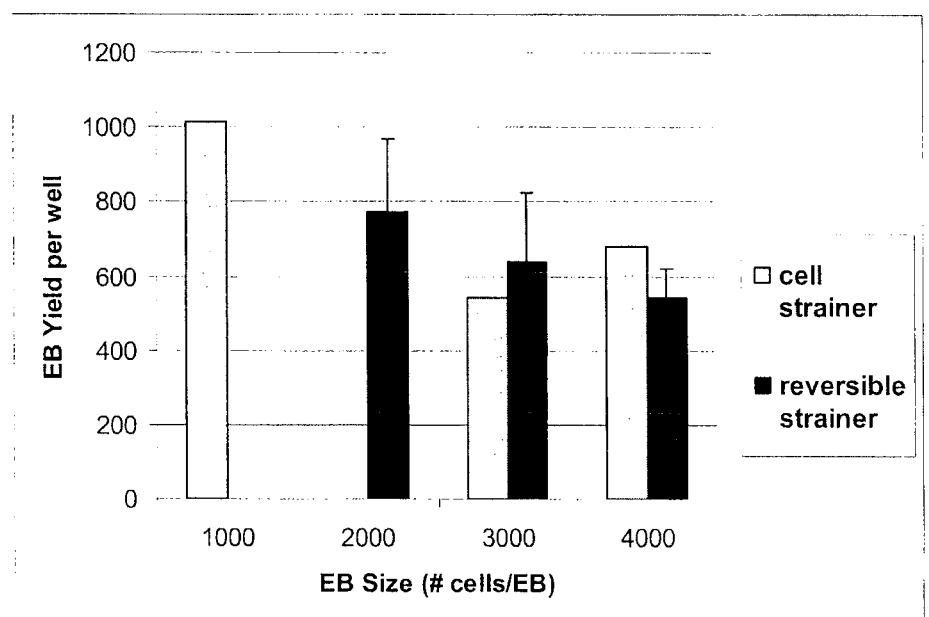
Figure 36:
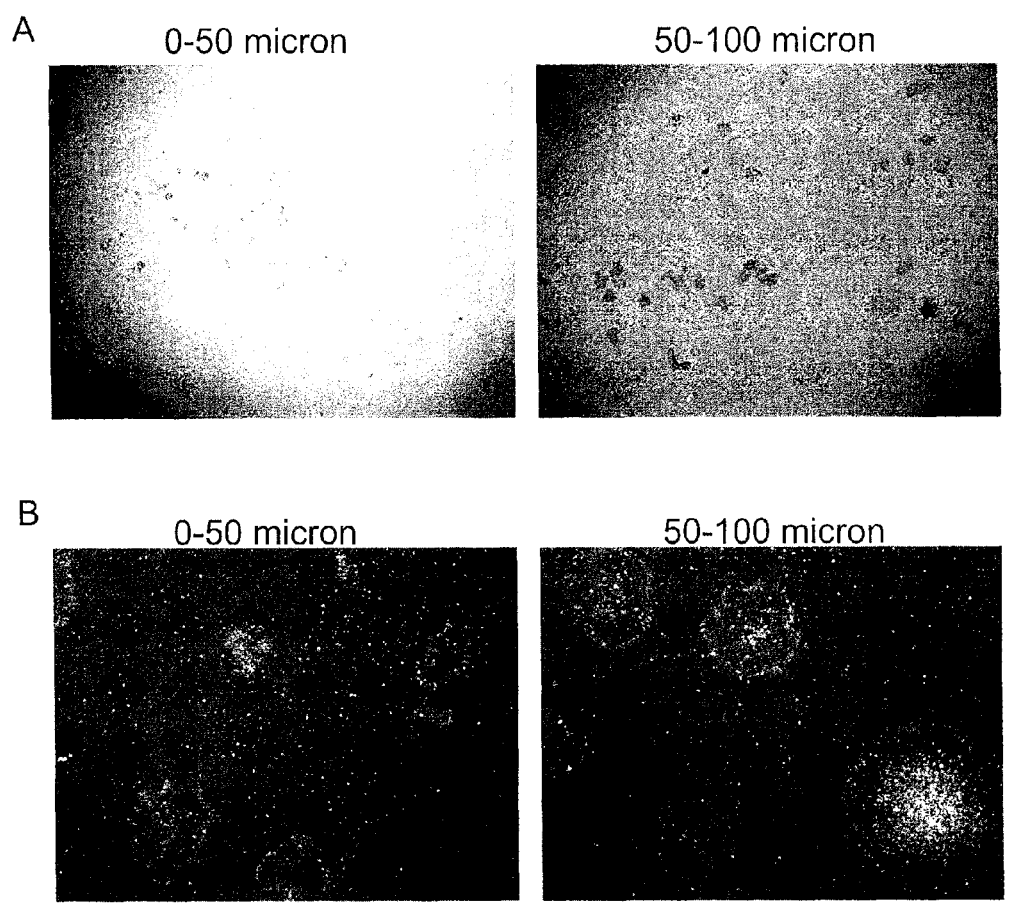

FIG. 30 shows a series of photographs of small and large prototype-2 filter apparatuses;

FIG. 31 shows the results after separation of single hES cells (FIG. 33A) and AggreWell™400-generated EBs (FIG. 33B) using various test mesh filters within prototype-1 filter apparatuses. Test mesh #1-6 were: (#1) Stainless steel mesh, 33 micron pore size, (#2) Nylon mesh, 50 micron pore size, (#3) expanded PTFE (teflon), 90 micron pore size, (#4) Nylon mesh, 30 micron pore size (#5) Nylon mesh, 50 micron pore size, and (#6) Nylon mesh, 37 micron pore size. These were compared against control: (#7) 40 micron cell strainer (BD);

FIG. 32 shows roughly equivalent yields of splenocytes after dissociation of murine spleen by forcing the soft tissue through either a 40 micron Cell Strainer (BD) or a 37 micron prototype-1 filter apparatus;

FIG. 33 shows fractionation of neurospheres by size, using prototype-2 filter apparatuses with nylon mesh of different sized pore openings. (A) 20× magnification photographs of sample neurospheres after fractionation, clearly showing differences in sizes of neurospheres harvested. (B) Graph of size distribution from each size fraction after separation;

FIG. 34 shows a series of photographs of small and large filter apparatuses generated by injection moulding;

FIG. 35 shows EB yields after harvesting from AggreWell™400 plate and separating aggregates from single cells using either Cell Strainer (BD, n=1 each) or the injection moulded filter apparatus (2000 c/EB n=6; 3000 c/EB n=3; 4000 c/EB n=3);

FIG. 36 shows fractionation of hES clumps by size, using prototype-2 filter apparatuses with nylon mesh of different sized pore openings. (A) 40× magnification photographs of clumps harvested from 0-50 and 50-100 micron fractions; (B) 20× magnification photographs of hES colonies formed 5 days after seeding 350 clumps per well from the 0-50 and 50-100 micron fractions;

DESCRIPTION OF VARIOUS EXAMPLES

Various apparatuses or processes will be described below to provide an example of an embodiment of each claimed invention. No embodiment described below limits any claimed invention and any claimed invention may cover processes or apparatuses that are not described below. The claimed inventions are not limited to apparatuses or processes having all of the features of any one apparatus or process described below or to features common to multiple or all of the apparatuses described below. It is possible that an apparatus or process described below is not an embodiment of any claimed invention. The applicants, inventors or owners reserve all rights that they may have in any invention disclosed in an apparatus or process described below that is not claimed in this document, for example the right to claim such an invention in a continuing application and do not intend to abandon, disclaim or dedicate to the public any such invention by its disclosure in this document.

Filter Apparatus

Various examples of a filter apparatus are shown in FIGS. 1-6 and 26-29, in which like numerals indicate like features, and numerals are shown incremented by 100 in order to correspond to the Figure number. The filter apparatus is usable, for example, to separate target entities, such as cellular aggregates, from a fluid based on their size, and further allows for collection of the target entities after they are separated. More specifically, the filter apparatus is usable to separate different populations of entities from each other based on size, and to collect each of the entities after they are separated.

Referring to FIGS. 1A-1C, a first example of a filter apparatus 100 is shown. The filter apparatus 100 comprises a filter 102, a first reservoir 104, and a second reservoir 106.

In the example shown, the filter 102 is a single membrane, which is a generally planar sheet. The filter 102 has a first surface 108, and a second surface 110 opposed to the first surface. In the example shown, the first surface 108 and the second surface 110 are provided by opposite faces of the membrane. In alternate examples, the filter 102 may comprise a plurality of stacked membranes, and the first surface 108 may be provided by a face of one of the membranes, and the second surface 110 may be provided by a face of another of the membranes.

The filter 102 may be fabricated from a variety of materials, including but not limited to nylon mesh, woven nylon filaments, polypropylene, polyethylene, polyester, polyetheretherketone, polytetrafluoroethyline, polyfluoroethylenepropylene, polyvinyls, polysulfone, polyvinyl fluoride, polychlorotrifluoroethylene, ethylene tetrafluoroethylene, or expanded metal mesh such as aluminum, bass, copper, nickel, bronze, steel, stainless steel or titanium.

The pore size of the filter 102 may vary depending on the particular application. In some examples, the pore size may be between about 5 microns in diameter and about 100 microns in diameter. Filters having a pore size of 5 microns may allow only molecules and cellular debris to pass therethrough. Filters having a pore size of between 20 microns and 100 microns will allow single cells, molecules, and cellular debris to pass therethrough. The exact filter size will depend on the type of cell being used, or the size of aggregate to be retained. For example, mouse thymocytes are approximately 6 μm in size, whereas liver cells are approximately 20 μm and human adipocytes are approximately 95 μm.

The first reservoir 104 is positioned adjacent and in communication with the first surface 108, and the second reservoir 106 is positioned adjacent and in communication with the second surface. Accordingly, the first 104 and second 106 reservoirs are in communication with each other via the filter 102. The first 104 and second 106 reservoirs allow for fluid to be provided to the filter 102 from either side of the filter. Accordingly, a fluid containing solids may be provided to one of the reservoirs, and may be allowed to pass through the filter 102. The filter apparatus 100 may then be inverted, and fluid may be provided to the other of the reservoirs, in order to wash the solids off of the filter 102. Accordingly, the fluid and the solids may be easily collected.

In the example shown, the first reservoir 104 is defined by a first sidewall 112, which extends outwardly from the first surface 108. In the example shown, the first sidewall 112 comprises a wall portion 114 which is generally cylindrical. However, in alternate examples, the first sidewall 112 may comprise a plurality of wall portions, which form a rectangular first sidewall, or another shape of first sidewall.

Similarly, in the example shown, the second reservoir 106 is defined by a second sidewall 116, which extends outwardly from the second surface 110. In the example shown, the second sidewall 116 comprises a wall portion 118 which is generally cylindrical. However, in alternate examples, the second sidewall 116 may comprise a plurality of wall portions, which for a rectangular first sidewall, or another shape of first sidewall.

In the examples shown, the first 112 and second 116 sidewalls extend substantially perpendicularly to the first 108 and second 110 surfaces, respectively. In alternate examples, the first 112 and second 116 sidewalls may not extend perpendicularly, and may, for example, be flared.

In some examples, the sidewalls 112, 116 may be generally symmetrical in shape. In such examples, the sidewalls 112 and 116 may be different colors, or may include one or more markers for differentiating the reservoirs from each other. In alternate examples, the sidewalls may not be symmetrical in shape.

The first 104 and second 106 reservoirs may be of a variety of sizes. In some examples, the size may be selected to allow for easy pouring or pipetting of fluid directly into the reservoirs while minimizing splashing, and to allow for the reservoirs to be inserted into a fluid vessel, as will be described further hereinbelow. In some examples, the reservoirs may have a diameter of between about 5 cm and about 6.5 cm, and the volume of the reservoirs may be between 0.5 cm$^3$ and 1000 cm$^3$. It will be appreciated that in alternate examples, the filter apparatus may be used with one or more funnels. That is, a funnel may be used to direct fluid into the filter apparatus, and another funnel may be used to direct fluid out of the filter apparatus. Accordingly, fluid may not be poured or pipetted directly into the reservoirs, and may not be inserted into a fluid vessel.

In alternate examples, the first reservoir and the second reservoir may be of different sizes. For example, in the filter apparatus 2600 shown in FIGS. 26A to 26C, the second reservoir 2604 has a smaller diameter than the first reservoir 2606. This may allow for a plurality of filter apparatuses 2600a-2600c to be stacked, as shown in FIG. 26C, by inserting the second reservoir of one filter apparatus into the first reservoir of another filter apparatus. Such stacking may be useful for storage purposes, or may allow the filter apparatuses 2600 to be used together, as will be described further hereinbelow.

Referring back to FIGS. 1A to 1C, in the example shown, communication between the first reservoir 104 and the first surface 108 is provided by an opening 113 defined by an inner end face 117 of sidewall 112, and communication between the second reservoir 106 and the second surface 110 is provided by an opening 115 defined by an inner end face 119 of sidewall 116. In alternate examples (not shown), communication may be provided in another manner. For example, the ends faces 117, 119 of sidewalls 112 and 116 may be covered by an end wall, and an aperture may be provided in each end wall for providing communication between the reservoirs 104, 106 and the first 108 and second 112 surfaces. In another alternate example (not shown), a conduit may be provided between reservoirs 104, 106, and the first 108 and second 110 surfaces.

A first inlet-outlet port 121 is in communication with the first reservoir 104, and a second inlet-outlet port 123 is in communication with the second reservoir 106. The inlet-outlet ports 121, 123 are spaced from the first 108 and second 110 surfaces, respectively. The inlet-outlet ports 121, 123 allow fluid to enter the reservoirs 104, 106, or to exit the reservoirs 104, 106, respectively, depending on the orientation of the filter apparatus 100. That is, if filter apparatus 100 is positioned such that the first reservoir 104 is above the second reservoir 106, fluid may enter the first reservoir 104 via first inlet-outlet port 121, for example by being poured into reservoir 104 through first inlet-outlet port 121, may pass through filter 102 into second reservoir 106, and may exit the second reservoir 106 via second inlet-outlet port 123. Alternately, if filter apparatus is positioned such that the second reservoir 106 is above the first reservoir 104, fluid may enter the second reservoir 106 via second inlet-outlet port 123, for example by being poured into reservoir 106 through second inlet-outlet port 123, may pass through filter 102 into first reservoir 104, and may exit the first reservoir 104 via first inlet-outlet port 121.

In the example shown, the first inlet-outlet port 121 is provided by an opening 120 defined by an outer end face 125 of wall portion 114, and the second inlet-outlet port 123 is provided by an opening 122 defined by an outer end face 127 of wall portion 118. In alternate examples, the ports 121, 123 may be provided in another manner. For example, the end faces 125, 127 of sidewalls 114, 116 may be covered by an end wall, and aperture may be provided in each end wall for providing the inlet-outlet ports.

In the example shown, the inlet-outlet ports 121, 123 are perpendicular to sidewalls. In alternate examples, the inlet-outlet ports 121, 123 may be at an angle with respect to sidewalls. This may facilitate dripping of a fluid through ports.

In the example shown, the first inner end face 117 is in contact with the first surface 108, and the second inner end face 119 is in contact with the second surface 110. Accordingly, the filter is generally sandwiched between the first 112 and second 116 sidewalls, and is secured and held in a fixed position therebetween.

In some examples, the first reservoir 104 and the second reservoir 106 may be fixedly mounted together. For example, as shown in FIGS. 1A to 1C, an adhesive may be applied to secure the first inner end face 117 to the second inner face 119, and to further secure the filter 102 therebetween. In alternate examples the first reservoir 104 may be removably mounted to the second reservoir 106. For example, in an alternate filter apparatus 200 shown in FIGS. 2A-2B, a recess 224 is defined in the first inner end face 217, and the second inner end face 219 is receivable in the recess 224. Screw threads are provided on the circumferential surface 226 of the recess, and mating screw threads are provided on the outer surface 228 of the second sidewall 216, such that the first 204 and second 206 reservoirs may be screwed together. Further, in this example, the filter 202 is sized to be received in the recess, such that the filter 202 may be sandwiched between the first 215 and second 217 inner end faces. Such an example may be useful, because a user may separate the first 204 and second 206 reservoirs, and remove and replace the filter 202 with a fresh filter.

In alternate examples, the filter may be removably secured to reservoirs 104 and 106 in another manner.

Figures 3A, 3B:
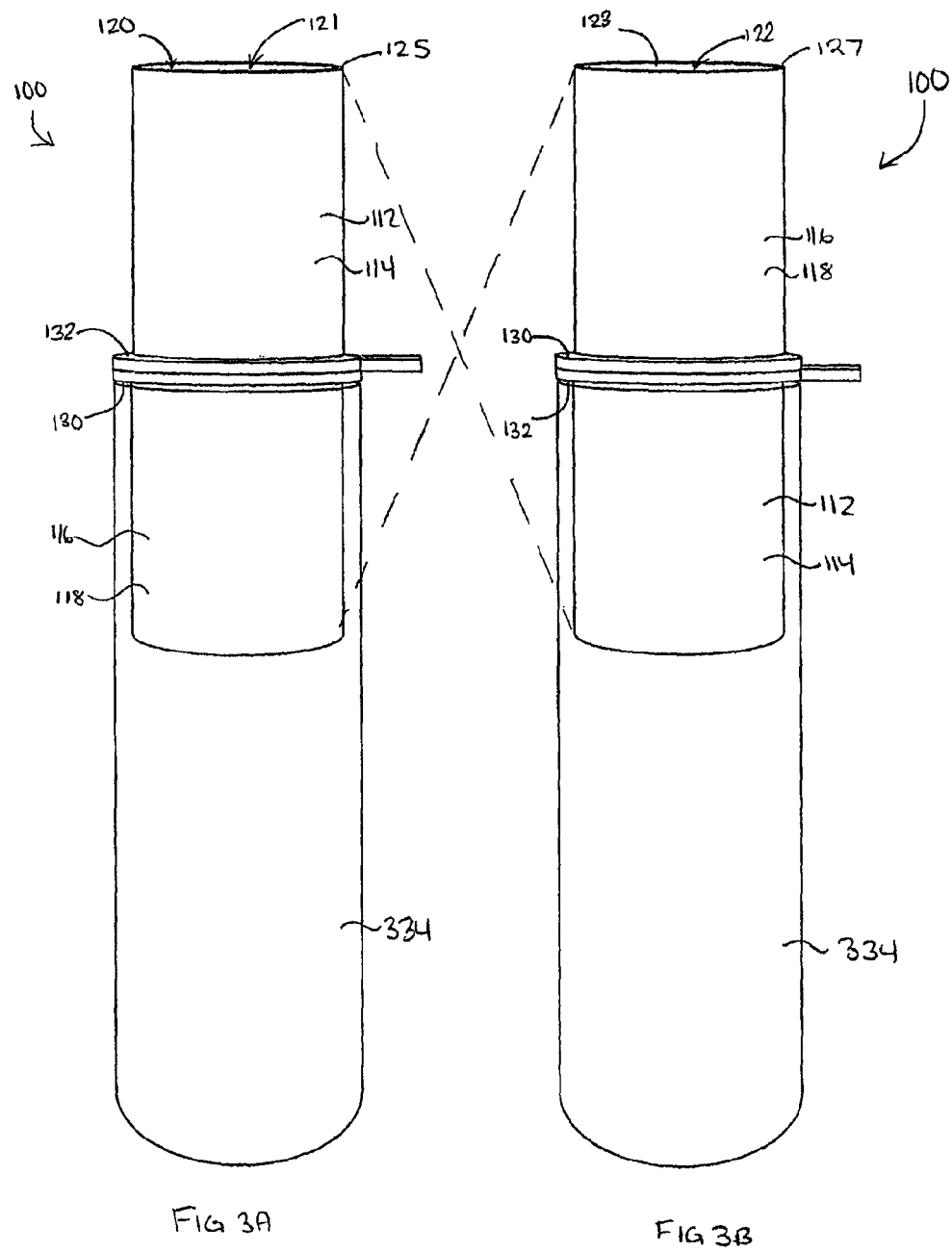
FIG. 3A is a perspective view of the filter apparatus of FIG. 1A, showing the filter apparatus coupled to a fluid vessel.
FIG. 3B is a perspective view of the filter apparatus of FIG. 1A, showing the filter apparatus inverted and coupled to an alternate fluid vessel.
Figure 4A:
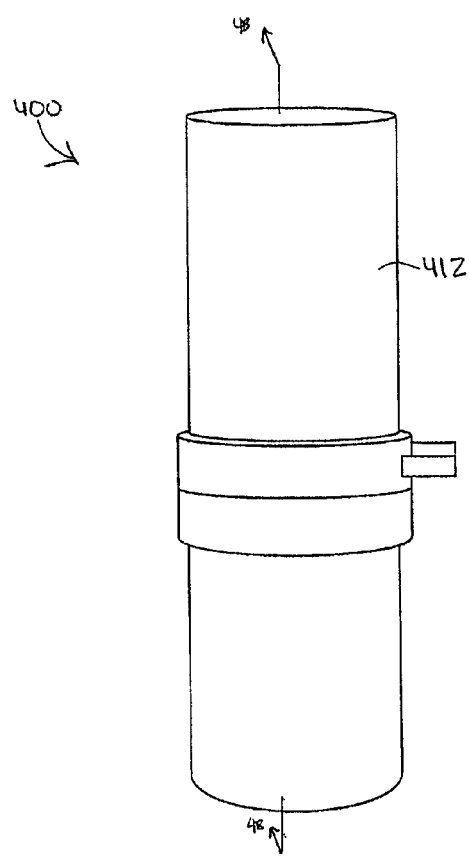
FIG. 4A is a perspective view of an alternate example of a filter apparatus.
Figure 4B:
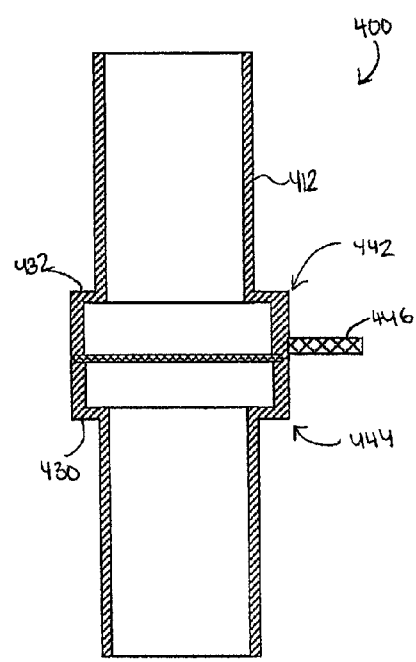
FIG. 4B is a cross section taken along line 4B-4B in FIG. 4A.

In the examples shown, filter apparatus 100 comprises a first seating surface 130, and a second seating surface 132. Referring to FIG. 3A, when the filter apparatus 100 is oriented such that the first reservoir 104 is above the second reservoir 106, the first seating surface 130 is seatable on the rim of a fluid vessel 334, to couple the filter apparatus 100 to the fluid vessel 334 such that the second inlet-outlet port 123 is positioned within the fluid vessel 334, and the first inlet-outlet port 121 is positioned above the fluid vessel 334. Referring to FIG. 3B, when the filter apparatus is oriented such that the second reservoir 106 is above the second reservoir 104, the second seating surface 132 is seatable on the rim of a fluid vessel 334, to couple the filter apparatus 100 to the fluid vessel 334 such that the first inlet-outlet port 121 is positioned within the fluid vessel 334, and the second inlet-outlet port 123 is positioned above the fluid vessel 334.

In the example shown in FIGS. 1 and 3, the first seating surface 130 is provided by a first flange 136, and the second surface is provided by a second flange 138. The first flange 136 is integral with the second sidewall 116, and the second flange 138 is integral with the first sidewall 112. In alternate examples, the seating surfaces 130, 132 may be provided in another manner. For example, as shown in FIG. 2, only a single flange 240 is provided, which is integral with first sidewall 212. Opposed surfaces of the flange 240 provide the first 230 and second 232 seating surfaces. In another alternate example of a filter apparatus 400 shown in FIG. 4, the first sidewall 412 may comprise a first stepped portion 442, and the second sidewall 416 may comprise a second stepped portion 444, which provide the first 430 and second 432 seating surfaces In alternate examples, a seating surface may not be provided. For example, the filter apparatus may be hand held. Furthermore, in some examples, wherein filter apparatus 100 is used with a funnel, a seating surface may not be required.

In some examples, the filter apparatus may be configured such that it may be coupled to fluid vessels of varying sizes. For example, in the example of a filter apparatus 500 shown in FIGS. 5A and 5B, the seating surfaces 530, 532 have a diameter that is much larger than the diameter of the fluid reservoirs. For example, the seating surfaces may have a diameter of up to 65 mm or greater, such that they can sit on the rim of a wide mouth bottle, as shown in FIG. 5B, or can sit on the rim a 0.5 mL Eppendorf tube, as shown in FIG. 5A, and the reservoirs may have a diameter of as low as 0.5 mm or less, such that they can fit into the rim of a 0.5 mL Eppendorf tube, or a wide mouth bottle. In such examples, as shown in FIGS. 27A and 27B, a plurality of ribs 2760 may be provided on opposed sides of the flange 2740. The ribs 2760 may serve to centre the filter apparatus 2700 when used with a larger vessel. When used with a smaller vessel, the ribs may provide the seating surfaces.

In another alternate example, shown in FIGS. 28A and 28B, the filter apparatus 2800 includes both a first 2636 and second 2638 flange and first 2842 and second 2844 stepped portions may be provided. When the filter apparatus 2800 is used with a smaller vessel, for example a 15 mL test tube, the stepped portions 2842, 2844 may provide the seating surfaces. When the filter apparatus 2800 is used with a larger vessel, for example a 50 mL test tube, the flanges 2836, 2838 may provide the seating surfaces.

In other alternate examples, one or more of the seating surfaces may be angled with respect to the filter. For example, in the filter apparatus 2900 as shown in FIGS. 29A and 29B, the seating surfaces 2930, 2932 provided by the stepped portions 2942, 2944 are angled with respect to filter 2902.

In the example shown in FIG. 1, the seating surfaces 130, 132 are only slightly larger in diameter than the fluid reservoirs, and therefore the filter apparatus is configured such that it may be couple to only one size of fluid vessel, or only a few sizes of fluid vessels having similar rim shapes and sizes. However, it will be appreciated that various sizes of filter apparatus 100 may be sold, and each size may be configured to be coupled to a different size of fluid vessel.

In the examples shown, filter apparatus 100 further comprises a handle 146. The handle 146 may be used to grip and re-orient the apparatus 100 by a user. In the example shown in FIG. 1, the handle 146 comprises a projection extending outwardly from flange 138. In the example shown in FIG. 4, the handle 446 comprises a projection extending outwardly from the stepped portion of sidewall 412. In alternate examples, the handle may be provided in another manner.

In some examples, an o-ring or a gasket may be provided for sealingly coupling the filter apparatus 100 to a fluid vessel. For example (not shown), a first and a second gasket may be provided adjacent each seating surface, and the gaskets may be sized to form a seal between the sidewalls 112, 116, and an inner wall of a fluid vessel of a given size. Such examples may be useful because the filter apparatus may be inverted together with the fluid vessel, without fluid leakage between the sidewalls 112, 116 and the fluid vessel.

In some examples, the filter apparatus may be a single use, disposable apparatus. In other examples, the filter apparatus may be reusable. The filter apparatus may be sterilizable.

In use, the filter apparatuses described hereinabove may be used to separate and collect populations of target entities based on size. The target entities may include cells, cellular aggregates, particles, particulate aggregates, and molecules. For example, the target entities may include cellular aggregates such as human or mouse embryoid bodies, tumour spheroids, neurospheres, aggregates of pluripotent stem cells (including ES and iPS cells) or mammospheres. More specifically, filter apparatuses 100-600 may be used to separate and collect two different populations of different sizes. An example of a method of using the filter apparatuses described hereinabove will presently be described. The method will be described with respect to filter apparatus 100; however, it will be appreciated that the method may be used with any of the filter apparatuses described hereinabove, or another filter apparatus. Furthermore, it will be appreciated that the filter apparatuses described hereinabove may be used according to alternate methods.

In use, a volume of fluid may be provided which has a first population of target entities dispersed therein. The volume of fluid may further have a second population of target entities dispersed therein. For example, the first population of target entities may include cellular aggregates, and the second population of target entities may include single cells, and it may be desired to separate the cellular aggregates and the single cells and collect each.

A filter apparatus 100 having a filter 102 with a pore size greater than the single cells, but smaller than the cellular aggregates may be selected. For example, the filter may have a pore size of 40 microns. The filter apparatus 100 may be positioned such that the second reservoir 106 is in communication with a fluid vessel, for example it may be positioned within the rim of an empty test tube such that seating surface 130 rests on the rim of the test tube, and such that the first reservoir 104 is above the second reservoir. The volume of fluid may then be provided to the first reservoir 104, for example by pouring the fluid into the first reservoir 104. The fluid, as well as the single cells, will pass through the filter 102 and into the fluid vessel, while the cellular aggregates will be retained on the first surface 108 of the filter. After the fluid has passed through the filter 102, additional washing steps may be performed. Accordingly, the single cells will become separated from the cellular aggregates, and will collect in the fluid vessel.

In order to collect the cellular aggregates, the filter apparatus 100 may then be inverted, and be positioned such that the first reservoir 104 is in communication with a second fluid vessel, for example another empty test tube, and such that the second reservoir 106 is above the second reservoir. A second volume of fluid, for example fresh culture media, may then be provided to the second reservoir 106, for example by pouring the fluid into the second reservoir 106. The second volume of fluid will pass through the filter 102, and will wash the cellular aggregates off of the first surface 108 of the filter 102 and into the second fluid vessel. Accordingly, the cellular aggregates will be collected in the second vessel.

In some examples, a second filter apparatus may then be provided, having a pore size greater than the pore size of the first filter apparatus. The method may be repeated using the second filter apparatus, in order to further separate the population of cellular aggregates based on size. For example, sub-populations of large aggregates and small aggregates may be separated from each other and retained. This may be repeated any number of times, using additional filter apparatuses of increasing pore sizes, in order to fractionate sub-populations based on size.

Furthermore, additional filter apparatuses of decreasing pore size may be provided, and may be used in order to further fractionate the population of single cells based on size.

Figure 6A:
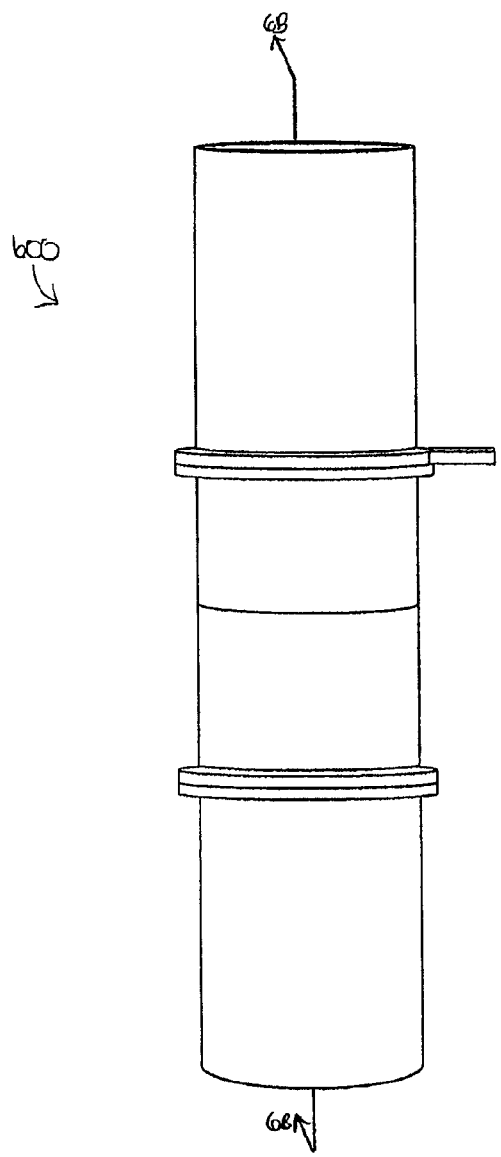
FIG. 6A is a perspective view of an alternate example of a filter apparatus.
Figure 6B:
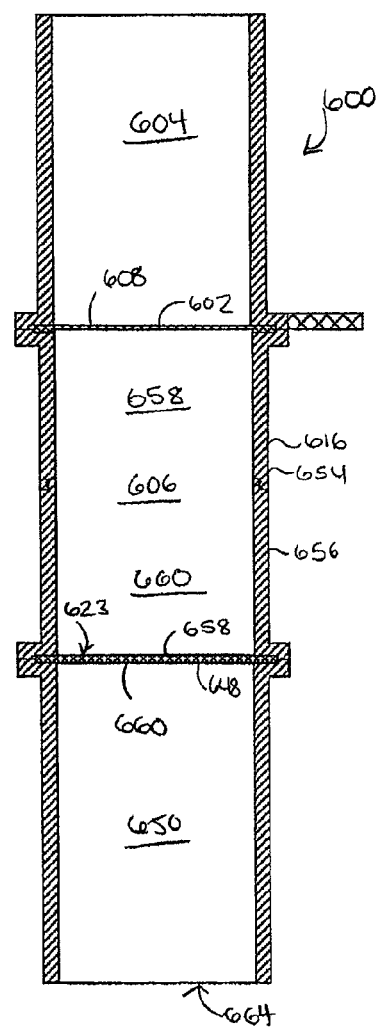
FIG. 6B is a cross section taken along line 6B-6B in FIG. 6A.
Figure 7:
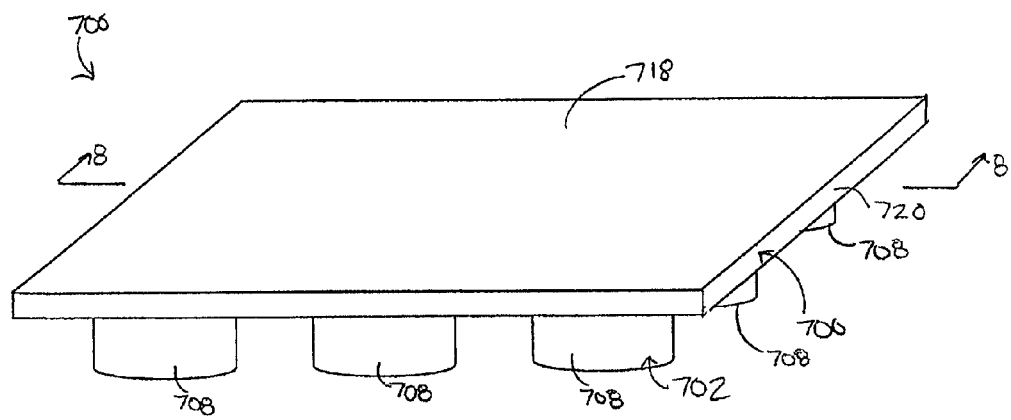
FIG. 7 is a perspective view of an example of a filter plate system.
Figure 8:
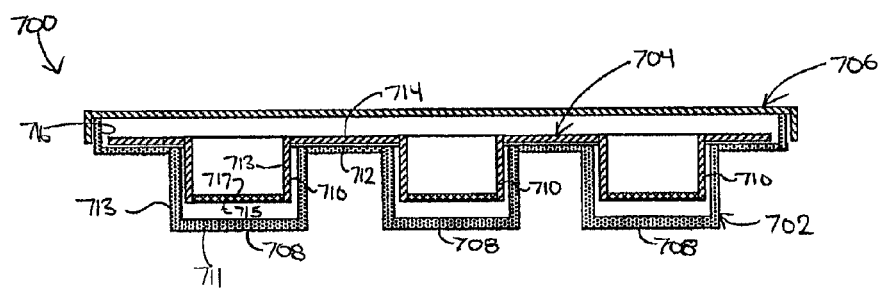
FIG. 8 is a cross section taken along line 8-8 in FIG. 7.
Figure 9:
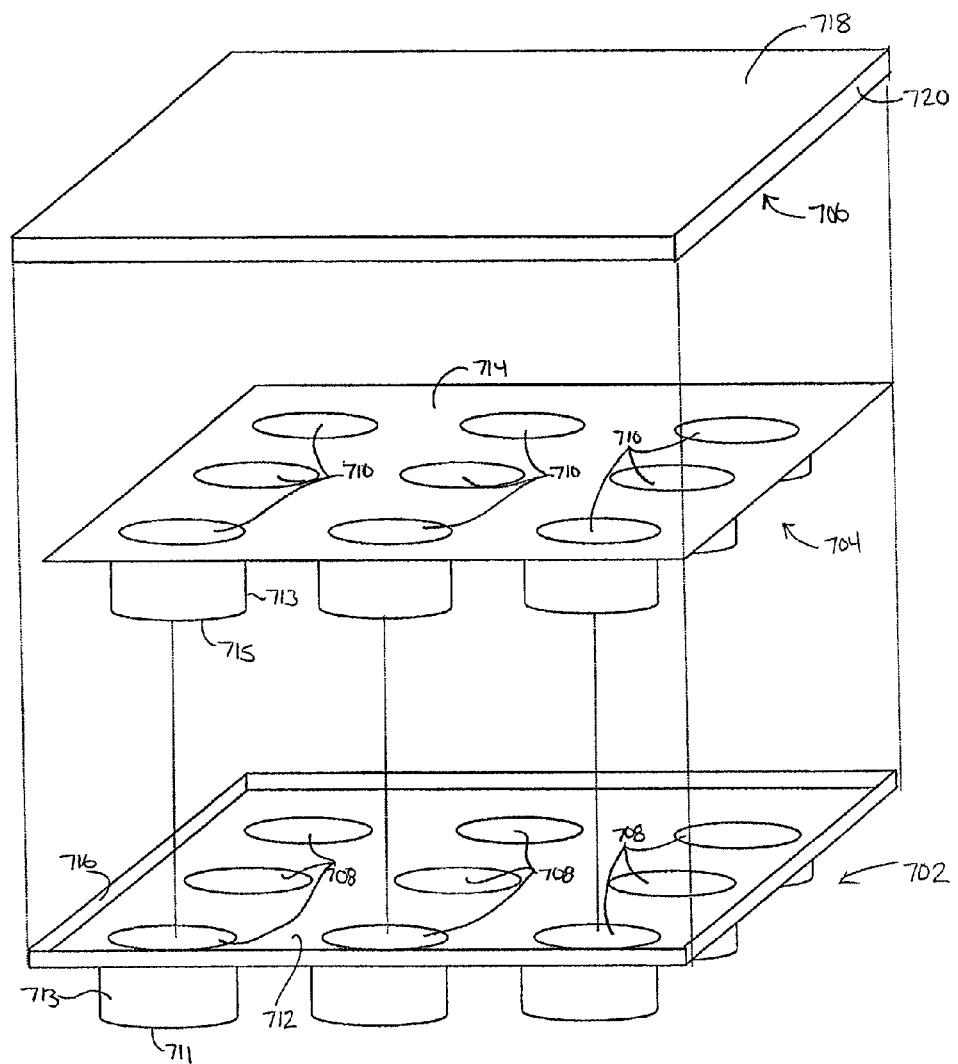
FIG. 9 is an exploded view of the filter plate system of FIG. 7.
Figure 10:
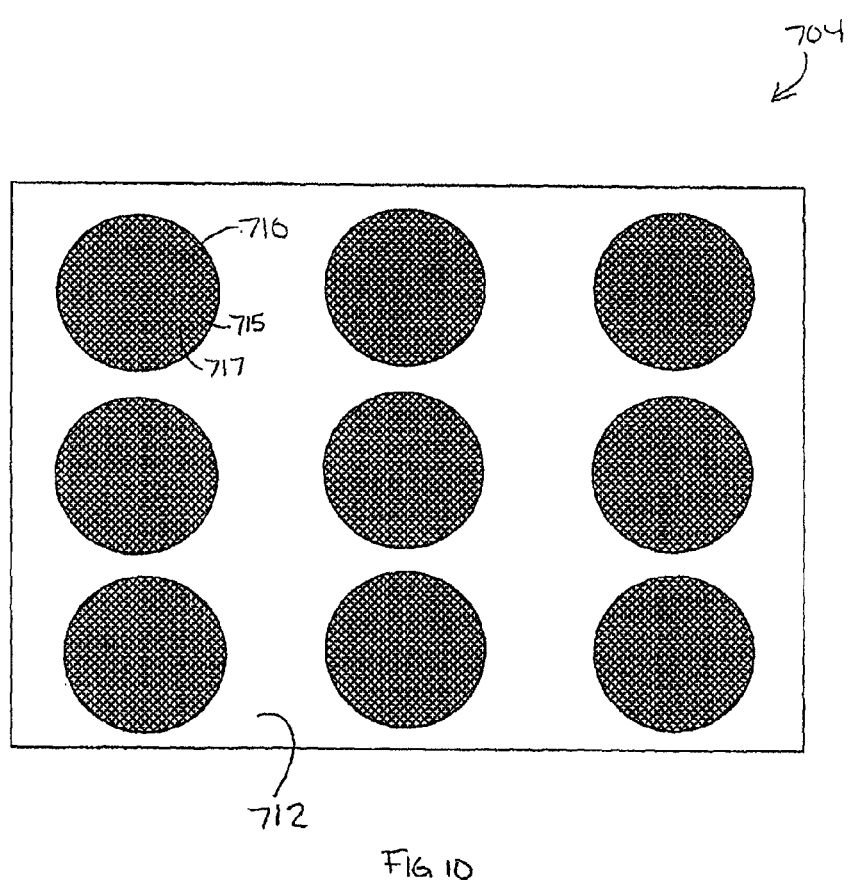
FIG. 10 is a top view of the strainer plate of the filter plate system of FIG. 7.

Alternately, rather than repeating the method using different filter apparatuses having different pore sizes, an alternate filter apparatus 600, shown in FIGS. 6A and 6B, may be used to fractionate a plurality of populations based on size. Filter apparatus is similar to filter apparatus 100, however filter apparatus 600 comprises an additional filter 648 and an additional reservoir 650. Further, the second sidewall 616 is separable into two portions 654, 656, to separate the second reservoir 606 into two portions 658 and 660. The two portions 654, 656 may be separable are re-attachable by any method, for example by providing mating screw threads on the first and second portions, as shown. The additional filter 648 is positionable across the inlet-outlet port 623 of the second reservoir 606, such that a first surface 658 of the additional filter is in communication with the second reservoir 606. The additional reservoir 650 is in communication with and adjacent a second opposed surface 662 of the additional filter 648, and an inlet-outlet port 664 of the additional reservoir 650 is spaced from the second surface 662. The additional filter 648 has a smaller pore size than the filter 602.

In use, filter apparatus 600 may be used to fractionate sub-populations based on size. For example, volume of fluid may be provided which has large cellular aggregates, small cellular aggregates, and single cells dispersed therein. Filter 602 may be selected to have a pore size smaller than the large cellular aggregates, but larger than the small cellular aggregates. Filter 648 may be selected to have a pore size smaller than the small cellular aggregates, and larger than the single cells.

The filter apparatus 600 may be positioned such that the additional reservoir 648 is in communication with a fluid vessel, such as an empty test tube, and such that the first 604 and second 606 reservoirs are above the additional reservoir 648. The volume of fluid may be provided to the first reservoir 604, such that the fluid, small cellular aggregates, and single cells pass through filter 602, and into second reservoir 606, while the large cellular aggregates are retained on the first surface 608 of the filter. The fluid and the single cells may then pass through the additional filter 648, into the additional reservoir 650, and into the fluid vessel, while the small cellular aggregates are retained on the additional filter 648. Any additional rinsing steps may also be performed.

In order to collect the small cellular aggregates and the large cellular aggregates, the second reservoir 606 may be separated into the two portions 654, 656. The first portion 654, which is coupled to the first reservoir 606, may then be inverted, and coupled to a second fluid vessel, such as an empty test tube, such that the first reservoir 604 is within the vessel, and the first portion 654 of the second reservoir 606 is above the vessel. A second volume of fluid may then be provided to the first portion 654 of the second reservoir 606, to wash the large cellular aggregates off of the filter 602 and into the second fluid vessel.

The second portion of the second reservoir 656, which is coupled to the additional reservoir 650, may then be inverted, and may be coupled to a third fluid vessel, such as an empty test tube, such that the second portion 656 of the second reservoir 606 is within the vessel, and the additional reservoir 650 is above the vessel. A third volume of fluid may then be provided to the additional reservoir 650, to wash the small cellular aggregates off of the additional filter 648 and into the third fluid vessel.

It will be appreciated that in some examples, further additional reservoirs and additional filters may be provided to the filter apparatus.

In further alternate examples, rather than providing a filter apparatus 600 having additional reservoirs, a plurality of separate filter apparatuses 2600 as shown in FIGS. 26A-26C may be provided, and may be stacked. The stacked filter apparatuses 2600 may be used in a similar manner to filter apparatus 600.

Filter Plate System

Referring to FIGS. 7 to 10, a filter plate system 700 is shown. The filter plate may be usable, for example, for in-vitro culture of cells or cellular aggregates, and may allow for relatively easy and efficient changes of culture media, while minimizing or reducing disturbance of the cells or aggregates. The cellular aggregates may include, for example, neurospheres, human or mouse embryoid bodies, or aggregates of pluripotent stem cells (including ES and iPS cells).

In the example shown, the filter plate system 700 comprises a reservoir plate 702, a strainer plate 704, and a lid 706. In alternate examples, a lid may not be provided.

In the example shown, the reservoir plate 702 comprises a plurality of reservoir wells 708, and the strainer plate 704 comprises a plurality of strainer wells 710. Specifically, in the example shown, the reservoir plate 702 comprises 9 reservoir wells 708, and the strainer plate 704 comprises 9 strainer wells 710. In alternate examples, the reservoir plate 702 and strainer plate 704 may each comprise only one well, or, for example, 6 wells, 12 wells, 24 wells, 48 wells, 96 wells, or 384 wells. Furthermore, in alternate examples, the reservoir plate 702 and the strainer plate 704 may not include the same number of wells. For example, the reservoir plate may comprise a plurality of wells, and the strainer plate may comprise only a single well. In such examples, a plurality of strainer plates may be provided, and the well of each may be receivable in a well of the reservoir plate, as will be described further hereinbelow. Alternately, the reservoir plate may comprise a single large reservoir well, and multiple strainer plate may comprise a plurality of strainer wells. In the example shown, the wells are arranged in a grid of rows and columns. In alternate examples, the wells may be arranged in another configuration.

In the example shown, the reservoir plate comprises an upper surface 712 extending between and around each well 708, and joining the wells 708 together. However, in examples wherein the reservoir plate 702 comprises only a single well 708, an upper surface 712 may not be provided.

Similarly, in the example shown, the strainer plate 704 comprises a common upper surface 714 extending between and around each well 710 and joining the wells 710 together. However, in examples wherein the strainer plate 704 comprises only a single well 710, an upper surface 714 may not be provided, or alternatively, the upper surface 714 may comprise a flange extending about the single well.

In the example shown, the reservoir plate further comprises an outer rim 716, which extends upwardly from the outer perimeter of the upper surface 712. The rim may be, for example, about 0.5 cm in height.

In the example shown, each reservoir well 708 comprises a reservoir well base wall 711, and a reservoir well sidewall 713, which is generally cylindrical. In alternate examples, a plurality of reservoir well sidewalls may be provided, and the reservoir wells may be another shape, for example cubic. Each reservoir well base wall 711 and sidewall 713 is substantially solid, such that liquid may be contained therein.

In the example shown, each strainer well 710 comprises a strainer well base wall 715, and a strainer well sidewall 713, which is generally cylindrical. In alternate examples, a plurality of strainer well sidewalls may be provided, and the strainer wells may be another shape, for example cubic. Each strainer well 710 comprises at least one mesh wall portion 717. In the example shown, the strainer well base wall 715 is the mesh wall portion 717, and the strainer sidewalls 713 are substantially solid. In alternate examples, the mesh wall portion 717 may comprise all or a portion of the strainer sidewalls 713, or only a portion of the strainer well base wall 715, or both of the strainer well sidewalls and base walls.

The mesh wall portion 717 serves as a filter. The mesh wall portion may comprise, for example, nylon, polypropylene, polyethylene, polyester, polyetheretherketone, polytetrafluoroethyline, polyfluoroethylenepropylene, polyvinyls, polysulfone, polyvinyl fluoride, polychlorotrifluoroethylene, ethylene tetrafluoroethylene, aluminum, bass, copper, nickel, bronze, steel, stainless steel or titanium. The pore size of the mesh wall portion may vary depending on the application, however, in some examples, the pore size is selected to allow single cells, as well as molecules and cellular debris, to pass therethrough under the force of gravity, without requiring any additional stimulus. For example, the pore size may be between 20 and 100 microns in diameter. This may allow liquid, molecules cellular debris, and single cells to pass therethrough, but cellular aggregates may not.

The strainer wells 710 are removably receivable in the reservoir wells 708. Accordingly, the reservoir wells 708 are slightly larger than the strainer wells 710. More specifically, the reservoir wells 708 are slightly larger in transverse cross section than the strainer wells 710, such that each strainer well is receivable in a reservoir well 708. Further, in the example shown, the reservoir wells 710 are slightly deeper than the strainer wells 708.

In the example shown, the strainer wells 710 are receivable in the reservoir wells 708 by seating the upper surface 714 of the strainer plate 704 on the upper surface 712 of the reservoir plate 702 and within the rim 716, such that each strainer well 710 is received in a reservoir well 708.

In alternate examples, as mentioned hereinabove, a plurality of strainer plates comprising single strainer wells, and a single reservoir plate comprising a plurality of reservoir wells, may be provided. The strainer well of each strainer plate may be individually receivable in one reservoir well of the reservoir plate. This is described hereinbelow in Example 11, and shown by photograph in FIG. 20. This may be advantageous because the cellular aggregates of each well may be washed and processed separately, if desired. In such examples, each strainer plate 704 may comprise a flange extending around the well, for seating on the upper surface 714 of the reservoir plate.

As mentioned hereinabove, a lid 706 may be provided. The lid 706 is mountable to the reservoir plate 702 to seal the strainer plate 704 within the reservoir plate. The lid 706 may form a sterile seal with the reservoir plate 702, which allows gas exchange, but not microbial or cellular exchange with the outside environment. In the example shown, the lid 706 comprises an upper surface 718, which is seatable on rim 716, and a skirt 720 extending downwardly from the upper surface 720, which is slidingly receivable around the rim 716. In alternate examples, the lid may be configured in another manner.

In some examples, each of the reservoir plate 702, strainer plate 704 (not including the mesh wall portion), and lid 706 are fabricated from polystyrene. In alternate examples, each of the reservoir plate 702, strainer plate 704 (not including the mesh wall portion), and lid 706 are fabricated from polycarbonate. In some examples, each of the reservoir plate 702, strainer plate 704 (not including the mesh wall portion), and lid 706 are transparent, such that the contents thereof may be viewed. For example, the contents may be viewed from below using an inverted microscope, or from above, using a regular microscope.

A method of using the filter plate system 700 will presently be described. However, it will be appreciated that the method may be used with alternate systems, and filter plate system 700 may be used according to alternate methods.

In use, the filter plate system 700 may be assembled such that each of the strainer wells 710 are received in a reservoir well 708. Fluid, for example culture media, may be added to the strainer wells 710 and/or the reservoir wells 708. Due to the mesh wall portion 717 of the strainer wells 710, the fluid will flow freely between the strainer wells 710 and the reservoir wells 708. A target population of cells and/or cellular aggregates may be added to the strainer wells 710. The cells or cellular aggregates may comprise, for example, mammalian cells, stem cells, human ES cells, or tumor cells. The mesh wall portion 717 of the strainer plate 704 may be selected to have a pore size less than the size of the cellular aggregates, but greater than the size of individual cells, such that the cellular aggregates may not flow from the strainer wells 710 into the reservoir wells 708, but the single cells may flow freely. For example, the pore size may be between 20 microns and 100 microns in diameter. The lid 706 may then be mounted to the reservoir plate 702, and the system may be left for a period of time, for example for a culture period of several hours or several days.

After a period of time, it may be desired to change the culture media, to provide fresh media to the cellular aggregates. In order to separate the cellular aggregates from the old media, the lid 706 may be removed from the reservoir plate 702, and the strainer plate 704 may be lifted off of the reservoir plate 702, such that the strainer wells 710 are removed from the reservoir wells 708. The cellular aggregates will remain in the strainer wells 710; however, the old fluid, including any single cells and cellular debris, will remain in the reservoir wells.

The strainer wells 710 may then optionally be washed, for example by rinsing with fluid.

The reservoir plate 702 may then be washed, and fresh media may be provided to the reservoir wells 710. Alternately, a new reservoir plate may be provided, containing fresh media. The fresh media may be the same formulation as the old media, or may be different, for example containing a different combination of growth factors or cytokines. The strainer plate 704 may then be placed back on the reservoir plate 702 containing the fresh media, and the strainer wells 710 may be re-inserted into the reservoir wells 708. The lid 706 may again be mounted to the reservoir plate, and a new culture period may begin.

In using this method to change culture media, the amount of disruption of the cellular aggregates may be minimal, particularly when the media is substantially viscous, for example when the media comprises methyl cellulose.

EXAMPLES

Example 1

Formation of Human ES Cell Aggregates by Forced Aggregation in Microwells

The following example used a microwell-textured plate (AggreWell™400 from Stemcell Technologies Inc., Vancouver, Canada, Catalogue #27845) for the forced aggregation of human embryonic stem (hES) cells in to embryoid bodies (EBs) of defined cell numbers.

Undifferentiated H1 hES cells were cultured to semi-confluency, using standard techniques. Typically, colonies reach semi-confluency 6 days after passaging of 2400 small clumps onto matrigel-coated 10-cm dishes and 7 mLs of mTeSR™1 media with daily media changes. An AggreWell™400 plate was removed from the packaging in a sterile tissue culture hood. Each of the 8 microwell-containing wells of the plate was rinsed with 1 mL of PBS, and the PBS was then removed by aspiration. 1 mL of medium was added to each well of the AggreWell™400 plate. Medium used in this example was AggreWell Medium™ (STEMCELL Technologies, Catalogue #27845). Y27632 Rock inhibitor (STEMCELL Technologies Catalogue #07171) was also added to the medium at a final concentration of 10 μg/mL to enhance cell survival during EB formation [Watanabe et al, Nat Biotechnol. 25(6): 681 (2007); US patent application no. 20080044901]. The AggreWell™400 plate was centrifuged at 2000×g for 2 minutes in a swinging bucket rotor fitted with a plate holder to remove any small bubbles from the microwells. AggreWell™400 plates were then set aside in tissue culture hood while preparing cells. 10-cm plates of H1 hES cells at semi-confluency were removed from the incubator and placed inside a sterile tissue culture hood. mTeSR®1 maintenance medium was aspirated from the H1 plates, and each plate was rinsed with 2 mL of PBS. PBS was then aspirated and discarded. Accutase® (STEMCELL Technologies, Catalogue #07920) was used to dissociate the adherent hES culture into single cells. 2 mL of Accutase® was added to each 10-cm plate of H1 cells. Plates were then incubated at 37° C. for approximately 10 mins, or until cells detached easily from the plate with gentle shaking. The H1 cell suspension was gently pipetted 2-3 times with a serological pipette to ensure any remaining clumps were fully dissociated and to dislodge any cells that were still attached to the surface of the dish. The suspension was transferred to a 50 mL conical tube. Each plate was rinsed 10 mL of PBS, and the rinsing solution was transferred to the same 50 mL tube containing the cell suspension. Cell suspensions were centrifuged at 350×g for 7 minutes at room temperature (15-25° C.). The supernatant was aspirated and discarded. Cell pellets were resuspended in a 1 mL volume of AggreWell™ Medium, supplemented with 10 μg/mL of Y27632 rock inhibitor. Viable cells were counted using standard techniques, by diluting a 10 μL sample of the cell suspension 1:10 in 90 μL of trypan blue and counting viable, unstained cells on a haemocytometer. A volume of cell suspension containing $2.4 \times 10^6$ viable cells was added to each well of the AggreWell™400 plate prepared previously. This amount of cells will distribute into the approximately 1,200 microwells to form EBs of approximately 2,000 cells each. AggreWell™ Medium with 10 μg/mL of Y27632 rock inhibitor was added as required, to a final volume of 2 mL per well. The AggreWell™400 plate was centrifuged at 100×g for 3 minutes to capture the cells in the microwells. Cultures were incubated at 37° C. with 5% CO2 and 95% humidity for 24 hours. EBs were then harvested in a sterile tissue culture hood, by gently pipetting up and down 2-3 times with a micropipettor outfitted with a 1 mL disposable tip to dislodge most of the EBs. The EB suspension was transferred to a 15 mL conical tube. The AggreWell™400 surface was washed a further 5 times with 1 mL each of DMEM/F-12, pipetting across the entire surface to dislodge all aggregates. All washes were collected in the same 15 mL tube as above. 250 μL of the suspension was transferred to 1 well of a flat-bottomed 96-well plate. EBs were counted from this 250 μL aliquot, and the total number of EBs in the suspension was calculated. Results are shown in Table 1. The suspension was centrifuged at 350×g for 7 minutes at room temperature (15-25° C.). The supernatant was aspirated and discarded, and the pellet was resuspended in 200 μL of DMEM/F12. Cells were counted using standard techniques, by diluting a 10 μL sample of the cell suspension in trypan blue and counting stained (dead) and unstained (viable) cells on a haemocytometer. This method does not dissociate the EBs, and only unaggregated single cells were counted. The results are shown in Table 1.

Figure 11:
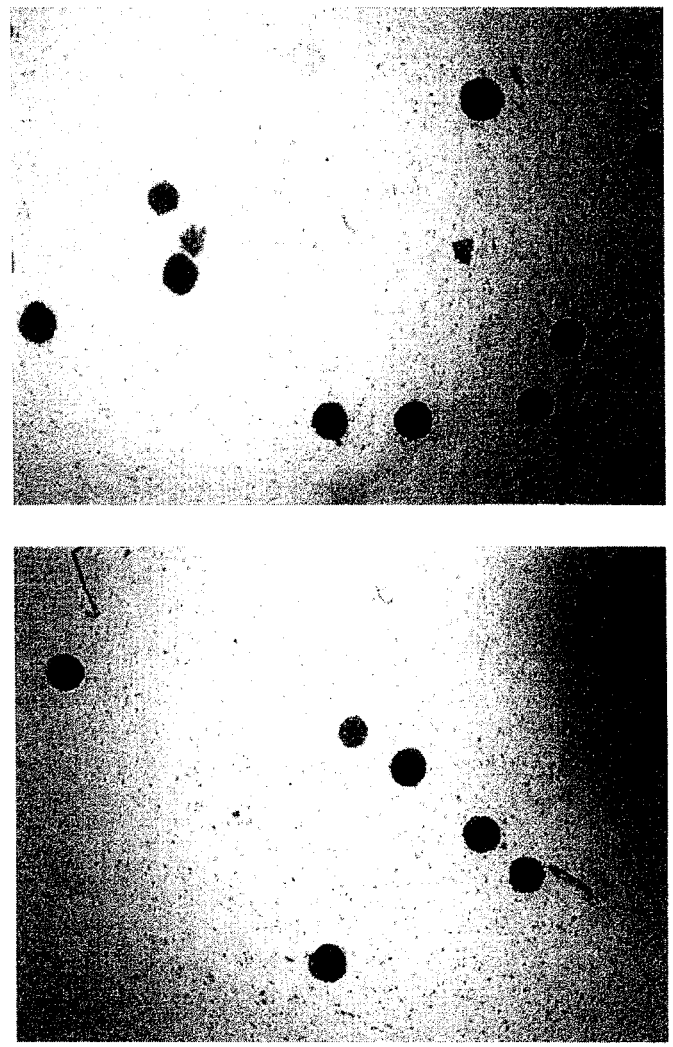
FIG. 11 shows EBs formed via forced aggregation in AggreWell plate, without filtration to remove single cells. 40× magnification.

As shown in Table 1 and FIG. 11, a significant number of both viable and dead cells were collected along with the aggregates (or EBs). These unaggregated single cells would contaminate subsequent EB culture to an undesirable level. Moreover, unaggregated single hES cells do not survive well, and the dying or dead cells release toxic compounds into the media, with detrimental effects to the EBs.

TABLE 1

Yield of single cells and EBs per well of AggreWell plate.

| Well No. | Aggregate Yield | Live Cell Yield | Dead Cell Yield |
|---|---|---|---|
| 1 | 1,310 | 165,000 | 1,170,000 |
| 2 | 1,434 | 320,000 | 1,470,000 |
| Average ± st dev | 1,372 ± 90 | 242,500 ± 110,000 | 1,320,000 ± 212,000 |

Example 2

Figure 12A:
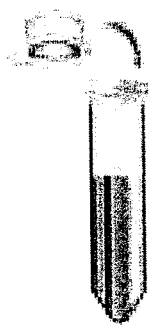
FIGS. 12A and 12B shows a method to harvest EBs, using a cell strainer flipped upside down.
Figure 12B:

Separation of EBs from Single Cells Using Commercially Available Cell Strainer in Non-Standard Way EBs were formed as described in Example 1, using AggreWell™400 from Stemcell Technologies Inc. Briefly, a single cell suspension containing 2.4×10⁶ H1 hES cells was added to each well of an AggreWell™400 plate, to generate approximately 1,200 EBs of 2,000 cells each. The EBs were then harvested as follows:

A cell strainer with 40 μm nylon mesh (Becton Dickson, Catalogue #352340) was removed from its packaging inside a sterile tissue culture hood and handled via its handle. The strainer was carefully placed upside down atop 50 ml test tube, as depicted in FIG. 12A. The cell strainer is not stably supported in this position, so a tight-fitting test tube rack was used to hold the 50 mL tube completely level and upright. Care was also taken throughout this procedure to avoid bumping the tube or the strainer, as it could easily fall off the tube. EBs were harvested from the AggreWell plate in a sterile tissue culture hood, by gently pipetting up and down 2-3 times with a micropipettor outfitted with a 1 mL disposable tip to dislodge most of the EBs. The EB-containing suspension was passed over the inverted cell strainer, allowing single cells and liquid to drip through by gravitational force. The AggreWell™400 surface was washed a further 5 times with 1 mL each of DMEM/F-12, pipetting across the entire surface to dislodge all aggregates. Washes were collected and passed over the same inverted cell strainer as above. The cell strainer was carefully handled via its handle, turned right side up, and placed over the rim of a fresh 50 ml collection tube, as depicted in FIG. 12B. The retained EBs were backflushed and collected into the 50 mL collection tube, by rinsing the cell strainer with 5 mL of growth factor-free mTeSR media. The entire content of the collection tube was then transferred to 1 well of an ultra-low adherence 6-well plate (Costar).

As shown in FIG. 13, the EBs formed by this method are largely uniform in size and shape. The bulk of unaggregated single cells have been successfully removed by the filtration method. However, the strainer was not supported atop the test tube, and tended to drift due to shaking of the tissue culture hood from constant running of the fan. It needed to be reset frequently to be directly above the test tube when in upside-down mode. If care was not taken to watch the amount of drift, and to reset the inverted strainer atop the tube frequently, it could fall off the tube. It could also easily be knocked off if the test tube rack was inadvertently bumped, resulting in loss of sterility and/or loss of aggregates.

Sterility was also difficult to maintain, as the cell strainer needed to be handled directly. The mesh side walls of the BD cell strainer allow transfer of microbials through. Therefore, care must be taken to touch the cell strainer only at the small handle, and not to touch the side walls.

Example 3

Separation of EBs from Single Cells Using Filter Apparatus Prototype-1

Figure 14:
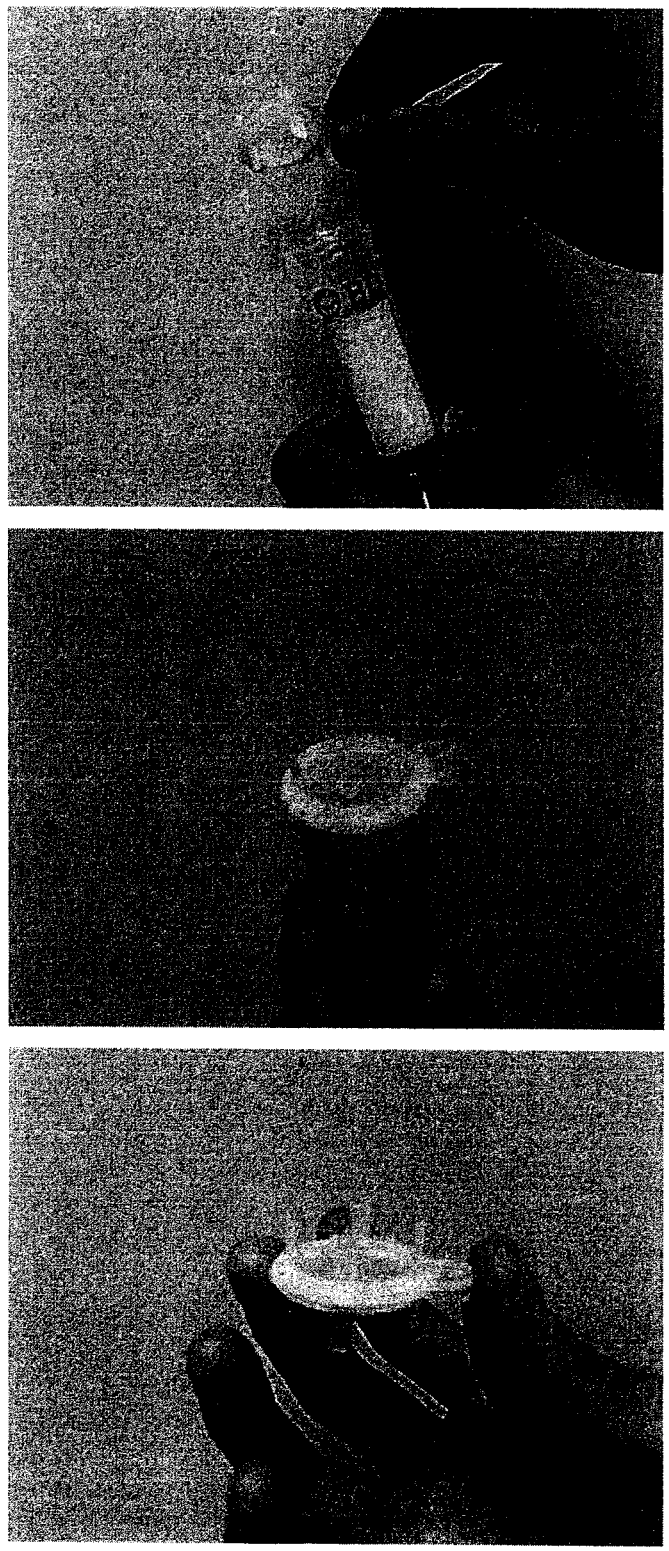
FIG. 14 is a series of photographs of a prototype-1 filter apparatus, without side walls.
Figure 16:
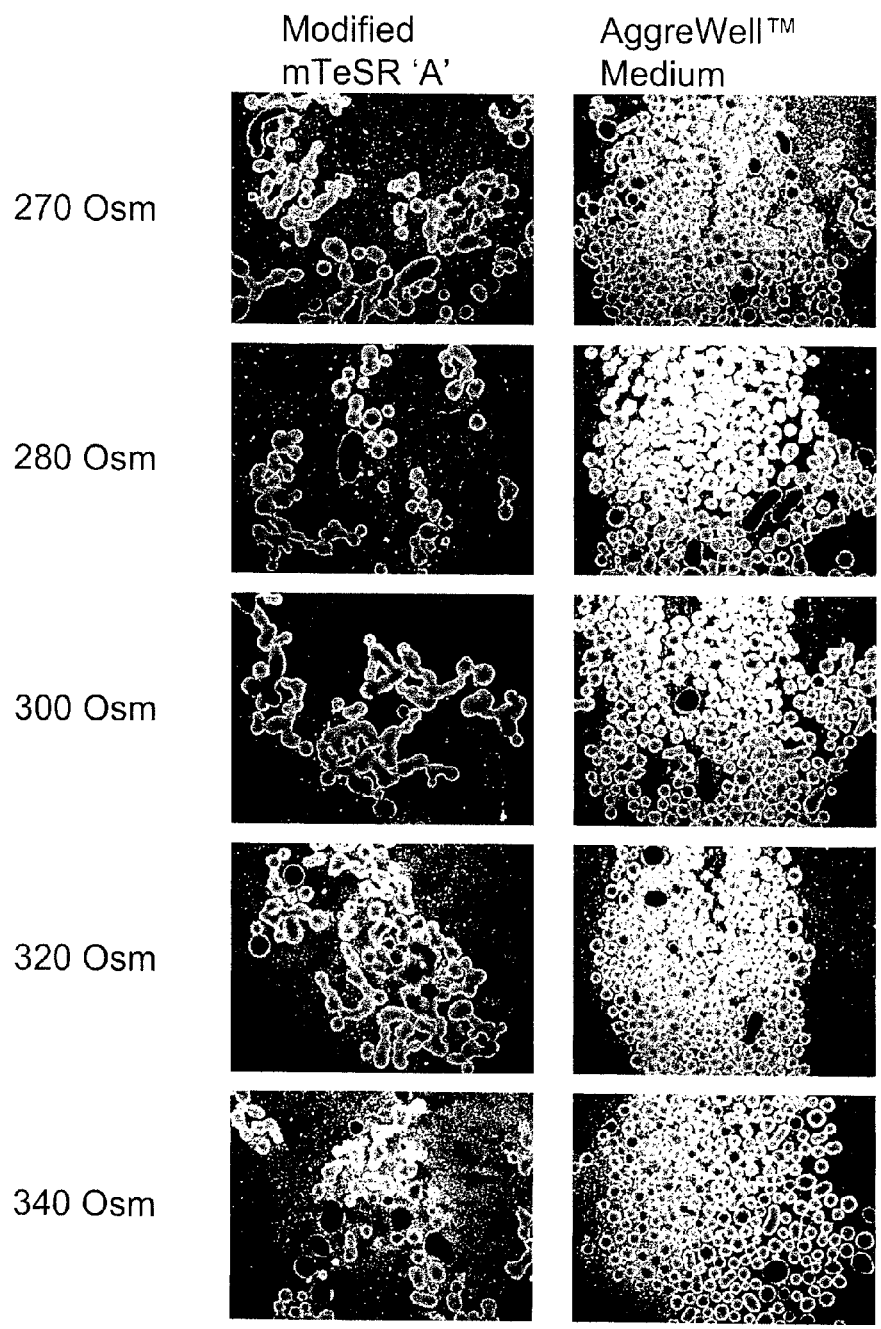
FIG. 16 shows EBs formed in AggreWell™400 and grown in either modified mTeSR media (left) or AggreWell™ Medium (right), produced at various osmolalities, for 4 days.

A filter apparatus as described hereinabove with respect to FIG. 1 was fashioned using the plastic casings from 2 commercially available cell strainers, and 50 μm nylon mesh. The cell strainers were disassembled, removing the mesh and side walls, leaving only the plastic casings. The plastic casings were placed with upper (flange) edges facing each other. A fresh piece of nylon mesh with 50 μm diameter openings (BioDesign Inc.) was placed between the two plastic casings, and the 3 parts were glued together. Excess nylon was trimmed from around the casings, resulting in the apparatus shown in FIG. 14. This device fit securely atop a 50 mL tube in either orientation.

Side walls were then fashioned onto the device using materials available in the lab such as tape and parafilm, to create a reservoir for application of cell suspension or washing solutions. The resulting device is shown in FIG. 15. This prototype-1 device was testing without sterilization, as detailed below.

EBs were formed as described in Example 1, using AggreWell™400 from Stemcell Technologies Inc. Briefly, a single cell suspension containing 2.4×10⁶ human ES cells was added to each well of an AggreWell plate, to generate approximately 1,200 EBs of 2,000 cells each. After 24 hours incubation at 37° C. with 5% CO2 and 95% humidity, the EBs were then harvested as follows:

The filter apparatus was placed atop a 50 ml test tube labeled "filtrate". EBs were harvested from the AggreWell plate by gently pipetting up and down 2-3 times with a micropipettor outfitted with a 1 mL disposable tip to dislodge most of the EBs. The EB suspension was passed through the filter apparatus, allowing single cells and liquid to drip through by gravitational force. The AggreWell™400 surface was washed a further 5 times with 1 mL each of DMEM/F-12, pipetting across the entire surface to dislodge all aggregates. Washes were collected and passed over the filter apparatus. Flowthrough was collected in the tube labelled "filtrate".

The filter apparatus was handled via its handle, removed from the tube labeled "filtrate", turned over, and transferred to a second 50 ml collection tube, labeled "filtrand". Particles (such as EBs) trapped on the filter were collected into the "filtrand" tube by flushing through with 5 mls of DMEM/F-12.

To count the number of EBs in each tube, a 250 μL aliquot of the suspension was transferred to 1 well of a flat-bottomed 96-well plate. EBs were counted from this 250 μL aliquot, and the total number of EBs in the suspension was calculated. Results are shown in Table 2.

To count the number of single cells in each tube, tubes were first centrifuged at 350×g for 7 minutes at room temperature (15-25° C.). The supernatant was aspirated and discarded, and the pellet was resuspended in 200 μL of DMEM/F12. Cells were counted using standard techniques, by diluting a 10 μL sample of the cell suspension in trypan blue and counting stained (dead) and unstained (viable) cells on a haemocytometer. This method does not dissociate the EBs, and only unaggregated single cells were counted. The results are shown in Table 2.

TABLE 2

Yields of single cells and EB aggregates in filter tube (filtrate) and aggregate collection tube (filtrand).

| Tube No. | Aggregate Yield | Live Cell Yield | Dead Cell Yield | Total No. Unaggregated Cells |
|---|---|---|---|---|
| Filtrate | 0 | 465,000 | 1,147,500 | 1,612,500 |
| Filtrand | 460 | 125,000 | 0 | 125,000 |

As shown in Table 2, the vast majority of unaggregated cells were collected in the "filtrate" tube, and thereby removed from the "filtrand" suspension. The "filtrand" contained all of the collected aggregates (or EBs). This method therefore effectively purified cellular aggregates from unaggregated live or dead cells. It has the advantage over the previous example in that the filter apparatus was stably supported atop both of the two collection tubes.

Example 4

Formulation of Modified mTeSR Media, in Liquid or Semi-Solid Form

The complete media formulation and method of preparation for modified TeSR (mTeSR) is published in Ludwig et al, Nature Methods 3(8): 637, 2006. Here we modified the formulation for mTeSR by reducing or removing the known pluripotency factors, to optimize EB growth in culture.

To manufacture the modified mTeSR media, a 5× supplement was produced with reduced concentrations or complete removal of one or more of the pluripotency factors: GABA, pipecolic acid, bFGF, TGFβ1, lithium chloride. Three versions of growth factor modifications were tested: modified mTeSR A, B, and C. Complete removal of all 5 pluripotency factors generated the medium referred to here as modified mTeSR "A". Modified mTeSR "A" is available from STEMCELL Technologies as Growth Factor-Free mTeSR®1 (Catalogue #05896), and comes with Basal and 5× components.

Liquid media of modified mTeSR was then produced by combining 400 mLs of osmolarity-matched DMEM/F12 with 100 mLs of the appropriate modified mTeSR (A-C) 5× supplement.

Alternatively, modified mTeSR (A-C) was made in semi-solid form, where the viscosity was increased by the addition of methylcellulose. To that end, methylcellulose was dissolved in distilled water ($dH_2O$) to generate at 2.6% w/v solution. 20 mL aliquots of 2.6% methylcellulose in water were stored at −20° C. 20 mL of the above 2.6% methylcellulose solution was mixed with 20 mL of a 2× concentrated solution of DMEM/F12 to generate a base solution of 1.3% methylcellulose in DMEM/F12.

To produce modified mTeSR in 1.0% methylcellulose, 40 mLs of 1.3% methylcellulose solution in DMEM/F12 was mixed with 10 mL of the appropriate modified mTeSR (A-C) 5× supplement. At 1.0% methylcellulose concentration the media was highly viscous, and could only be measured and transferred accurately using a syringe fitted with a blunt needle.

To produce modified mTeSR in 0.5% methylcelluose, 20 mLs of 1.3% methylcellulose solution in DMEM/F12 was mixed with 20 mLs of DMEM/F12 and 10 mL of the appropriate modified mTeSR (A-C) 5× supplement. At 0.5% methylcellulose, the media was more viscous than liquid media, but could be transferred using standard pipettes.

Example 5

4 Day Suspension Culture of EBs in Modified mTeSR Liquid Media

EBs were formed as described in Example 1 and separated from the unaggregated cells as described in Example 2. Briefly, a single cell suspension containing $2.4 \times 10^6$ human ES cells was added to a well of AggreWell™400, to generate approximately 1,200 EBs of 2,000 cells each. The resulting suspension was passed over an inverted cell strainer to remove unaggregated single cells and debris, and the collected aggregate contents of the strainer were backflushed with DMEM/F12 into a fresh tube to collect the aggregated EBs (described in Example 2).

EBs were left to settle to the bottom of tube, by incubating 5 mins at room temp. Supernatant was removed, leaving pelleted EBs at the bottom of the tube. EBs were resuspended in 1 mL of modified mTeSR media (described in example 4), and transferred to a single well of a 6-well ultra-low adherence dish (STEMCELL Technologies, Catalogue #27145). A further 4 mL of the same media was added to each well, bringing the total volume up to 5 mL per well. Plates containing EBs were incubated in a standard tissue culture incubator, at 37° C., 5% CO2 and 95% humidity for a period of 4 days.

EB morphology was observed under an inverted microscope and photographically recorded every 1-2 days. EBs were counted every 1-2 days. To count EBs, a celluloid transparency sheet with an X-Y grid was placed under the dish on the microscope. The stage was moved along the grid and EBs were counted across the entire well.

After 4 days, EBs were harvested from each well as described. EBs were dissociated to single cells using Accutase® (STEMCELL Technologies). 1 mL of Accutase® was added per tube (containing the EB contents of 1 well). The suspension was incubated at 37° C. for 10 minutes. After this time, the cell suspension was gently pipetted 2-3 times with a serological pipette to ensure any remaining EBs were fully dissociated. 10 mL of PBS was added to each tube, to inactivate the Accutase® by dilution. The tube was then centrifuged at 350×g for 7 mins at room temperature. Cells were counted using standard techniques by diluting a 10 µL aliquot of the cell single cell suspension in trypan blue and counting unstained viable cells on a haemocytometer.

The results of this culture experiment are shown in FIG. 17 and Table 3. Although the total number of EBs decreased from an input of approximately 1,200 EBs per well, a significant number of EBs survived the 4 day culture period. EBs were generally larger than the input of approximately 2,000 cells/EB, indicating either merging together of multiple EBs, or cell proliferation within the EB.

TABLE 3

Yields and Cellularities of EBs after 4 days liquid culture in modified mTeSR media.

| Media Type | Day 4 EB Yield | Day 4 No. Cells per EB |
|---|---|---|
| Modified mTeSR A | 57 ± 59 | 12,476 ± 9,989 |
| Modified mTeSR B | 230 ± 272 | 3,878 ± 2,371 |
| Modified mTeSR C | 331 ± 42 | 1,818 ± 1,812 |

Example 6

4 Day Suspension Culture of EBs in AggreWell™ Medium or Standard EB Culture Conditions EBs were formed as described in Example 1 and separated from the unaggregated cells as described in Example 2. Briefly, a single cell suspension containing $2.4 \times 10^6$ human ES cells was added to a well of AggreWell™400, to generate approximately 1,200 EBs of 2,000 cells each. The resulting suspension was passed over an inverted cell strainer to remove unaggregated single cells and debris, and the collected aggregate contents of the strainer were backflushed with DMEM/F12 into a fresh tube to collect the aggregated EBs (described in Example 2). The EBs were then cultured as follows:

A 100 µL aliquot of the EB-containing suspension was transferred to 1 well of a flat-bottomed 96-well plate. The plate was placed under an inverted microscope, and EBs were counted at 40× magnification. The total number of EBs in the EB suspension was then calculated. EBs were left to settle to the bottom of tube, by incubating 5 mins at room temp.

Supernatant was removed, leaving pelleted EBs at the bottom of the tube. EBs were resuspended in 1 mL of AggreWell™ Medium (STEMCELL Technologies Catalogue#05893). A volume of the well-mixed suspension calculated to contain 500 EBs was transferred to each well of a 6-well ultra-low adherence dish (STEMCELL Technologies, Catalogue #27145). More AggreWell™ Medium was added to each well, bringing the final volume up to 5 mL per well.

Plates containing EBs were incubated in a standard tissue culture incubator, at 37° C., 5% CO2 and 95% humidity for a period of 4 days.

EB morphology was observed under an inverted microscope and photographically recorded every 1-2 days. EBs were counted every 1-2 days. To count EBs, a celluloid transparency sheet with an X-Y grid was placed under the dish on the microscope. The stage was moved along the grid and EBs were counted across the entire well.

After 4 days, EBs were harvested from each well as described in step 8. EBs were dissociated to single cells using Accutase®. 1 mL of Accutase® was added per tube (containing the EB contents of 1 well). The suspension was incubated at 37° C. for 10 minutes. After this time, the cell suspension was gently pipetted 2-3 times with a serological pipette to ensure any remaining EBs were fully dissociated. 10 mL of PBS was added to each tube, to inactivate the Accutase® by dilution. The tube was then centrifuged at 350×g for 7 mins at room temperature. Cells were counted using standard techniques by diluting a 10 μL aliquot of the cell single cell suspension in trypan blue and counting unstained viable cells on a haemocytometer. Single cells were used for a variety of standard assays, including fluorescence activated cell sorting (FACS), colony forming cell (CFC) assay, and RNA extraction for real-time quantitative polymerase chain reaction (RT-Q-PCR).

The results of this culture experiment are shown in FIG. 24 and Table 3. Although the total number of EBs decreased from an input of approximately 1,200 EBs per well, a significant number of EBs survived the 4 day culture period. EBs were generally larger than the input of approximately 2,000 cells/EB, indicating either merging together of multiple EBs, or cell proliferation within the EB. In comparison, EBs cultured in standard EB medium (DMEM/F12 with 20% FBS) did not survive well, and EBs cultured in XVivo10 merged together into large conglomerates of cells.

TABLE 4

Yields and Cellularities of EBs after 4 days liquid culture in various media.

| Media Type | Day 4 EB Yield | Day 4 No. Cells per EB |
| --- | --- | --- |
| DMEM/F12 20% FBS | 19 ± 28 | 2,612 ± 2,371 |
| AggreWell ™ Medium | 234 ± 297 | 10,487 ± 20,774 |
| XVivo10 | 20 ± 4 | 47,366 ± 34,380 |

Example 7

Suspension Culture of EBs in 0.5% Methylcellulose-Based, Modified mTeSR Medium

EBs were formed as described in Example 1, using AggreWell™400 from Stemcell Technologies Inc. Briefly, a single cell suspension containing $2.4 \times 10^6$ human ES cells was added to a well of AggreWell™400, to generate approximately 1,200 EBs of 2,000 cells each. The EBs were then treated as follows:

EBs were harvested from microwells and separated using an inverted cell strainer. 5 mLs of DMEM/F12 was used to wash all EBs from the AggreWell plate, and collected together on the inverted cell strainer. The cell strainer was placed right-side up on a fresh tube, and EBs were collected by backflushing with 2 mL of modified mTeSR media per well of AggreWell used. EB yield was determined by placing a 100 μL sample of evenly distributed EB suspension into one well of a flat-bottomed 96-well plate, and counting the EBs in that sample. EB yield was calculated as 20× number of EBs counted in 100 μL. EBs were allowed to settle to bottom of tube, by incubating 5 mins at room temp. Media was removed, keeping pelleted EBs. EBs were resuspended in 200 μL of modified mTeSR medium "A" (see Example 4). A volume (less than 100 μL) of the well-mixed EB suspension containing 500 EBs was transferred to each well of a 6-well ultra-low adherence dish (Corning). 5 mLs of 0.5% methylcellulose based modified mTeSR "A" was added to each well, using a 6 cc syringe and a blunt-ended needle. After applying the 0.5% methylcellulose mixture, the needle end was used to mix the cell suspension on the plate and distribute the EBs evenly. Plates were placed into a standard tissue culture, at 37° C., 5% CO2 and 95% humidity. EB morphology was observed and EBs were counted in situ every 2-4 days. To count EBs, a celluloid transparency sheet with an X-Y grid was placed under the dish on the microscope, and the stage was moved around the grid to count the EBs.

Every 2-4 days a complete media change was carried out. 2-5 mLs of DMEM/F12 was added to each well, to dilute the methylcellulose and decrease viscosity of the media. After brief pipetting to mix, the entire contents were transferred to a 15 mL conical tube. The well was then washed with an additional 5 mLs of DMEM/F12, and the resulting suspension was transferred to the same tube. The tube was inverted to mix, and to decrease the total viscosity. EBs were allowed to settle to the bottom of the tube, by leaving the tube undisturbed at room temperature for 5 mins. If EBs were visible in the supernatant after 5 mins, then the tube was centrifuged at 600 rpm for 2 mins to pellet all EBs. Liquid media containing single cells was removed by pipette or aspiration, leaving the EBs at the bottom of the tube. EBs were resuspended in 100 μL of the same culture media as used above (in this case modified mTeSR "A") and transferred to a fresh well of a 6-well ultra low adherence plate. 5 mLs of 0.5% methylcellulose based modified mTeSR "A" was added to each well, using a 6 cc syringe and a blunt-ended needle. After applying the 0.5% methylcellulose mixture, the needle end was used to mix the cell suspension on the plate and distribute the EBs evenly.

After 14 days, EBs were harvested from each well as described above. On day 14, harvested EBs were dissociated to single cells using Accutase®. 1 mL of Accutase® was added per tube (containing the EB yield from 1 well). Tubes were then incubated at 37° C. for 20 minutes. Cell suspensions were pipetted 2-3 times with a serological pipette to ensure any remaining EBs were fully dissociated. Accutase® was washed off by adding 10 mL of PBS per tube, and tubes were centrifuged at 1200 rpm for 7 mins at room temperature. Cells were counted using standard techniques by diluting a 10 μL aliquot of the cell single cell suspension in trypan blue and counting unstained viable cells on a haemocytometer.

The results of this experiment are shown in FIG. 18.

Example 8

Suspension Culture of EBs in 1.0% Methylcellulose-Based, Modified mTeSR Medium

EBs were formed as described in Example 1, using AggreWell™400 from Stemcell Technologies Inc. Briefly, a single cell suspension containing $2.4 \times 10^6$ human ES cells was added to a well of AggreWell, to generate approximately 1,200 EBs of 2,000 cells each. The EBs were then treated as follows:

EBs were harvested from microwells and separated using an inverted cell strainer (described in Example 2). 5 mLs of DMEM/F12 was used to wash all EBs from the AggreWell plate, and collected together on the inverted cell strainer. The cell strainer was placed right-side up on a fresh tube, and EBs were collected by backflushing with 2 mL of modified mTeSR "A" medium (see Example 4) per well of AggreWell™400 used. EB yield was determined by placing a 100 µL sample of evenly distributed EB suspension into one well of a flat-bottomed 96-well plate, and counting the EBs in that sample. EB yield was calculated as 20× number of EBs counted in 100 µL. A volume of the EB suspension containing 1,500 EBs was transferred to a fresh tube. EBs were allowed to settle to bottom of tube, by incubating 5 mins at room temp. Media was removed, keeping pelleted EBs. EBs were resuspended in 300 µL of liquid modified mTeSR "A". This was transferred to a tube containing a 2.7 mL aliquot of modified mTeSR A in 1.0% methylcellulose. The tube was vortexed to distribute the EBs evenly. 1 mL of the EB-containing methylcellulose mixture, estimated to contain 500 EBs, was plated onto each well of a 6-well ultra-low adherence plate. Plates were placed into a standard tissue culture, at 37° C., 5% CO2 and 95% humidity.

EB morphology was observed and EBs were counted in situ every 2-4 days. To count EBs, a celluloid transparency sheet with an X-Y grid was placed under the dish on the microscope, and the stage was moved around the grid to count the EBs.

Every 2-4 days a complete media change was carried out. 2-5 mLs of DMEM/F12 was added to each well, to dilute the methylcellulose and decrease viscosity of the media. After brief pipetting to mix, the entire contents were transferred to a 15 mL conical tube. The well was then washed with an additional 5 mLs of DMEM/F12, and the resulting suspension was transferred to the same tube. The tube was inverted to mix, and to decrease the total viscosity. EBs were allowed to settle to the bottom of the tube, by leaving the tube undisturbed at room temperature for 5 mins. If EBs were visible in the supernatant after 5 mins, then the tube was centrifuged at 600 rpm for 2 mins to pellet all EBs. Liquid media containing single cells was removed by pipette or aspiration, leaving the EBs at the bottom of the tube. EBs were resuspended in 100 µL of the same culture media as used previously (in this case modified mTeSR "A") and transferred to a fresh well of a 6-well ultra low adherence plate. 5 mLs of 1.0% methylcellulose based growth factor-free mTeSR was added to each well, using a 6 cc syringe and a blunt-ended needle. After applying the 0.5% methylcellulose mixture, the needle end was used to mix the cell suspension on the plate and distribute the EBs evenly.

After 14 days, EBs were harvested from each well as described above. On day 14, harvested EBs were dissociated to single cells using Accutase®. 1 mL of Accutase® was added per tube (containing the EB yield from 1 well). Tubes were then incubated at 37° C. for 20 minutes. Cell suspensions were pipetted 2-3 times with a serological pipette to ensure any remaining EBs were fully dissociated. Accutase® was washed off by adding 10 mL of PBS per tube, and tubes were centrifuged at 1200 rpm for 7 mins at room temperature. Cells were counted using standard techniques by diluting a 10 µL aliquot of the cell single cell suspension in trypan blue and counting unstained viable cells on a haemocytometer. Single cells were used for a variety of standard assays, including fluorescence activated cell sorting (FACS), colony forming cell (CFC) assay, and RNA extraction for real-time quantitative polymerase chain reaction (RT-Q-PCR).

The results of this experiment are shown in FIG. 18.

Example 9

Culture of EBs in 0.5% Methylcellulose-Based Media on Prototype Strainer Plate to Facilitate Media Changes A filter plate system as described hereinabove with respect to FIGS. 7-10 was prepared by: forming a strainer well by aseptically removing a 40 µm cell strainer from its packaging, cutting off the handle, and placing the strainer well inside a well of a 6-well tissue culture plate, which served as a reservoir plate. This was repeated for all 6 wells on the plate.

EBs were generated using AggreWell™400, then harvested and separated as described in Example 2. 5 mLs of DMEM/F12 was used to wash all EBs from the AggreWell plate, and collected together on the filter apparatus. The filter apparatus was placed right-side up on a fresh tube, and EBs were collected by backflushing with 2 mL of growth-factor free mTeSR media per well of AggreWell used. EB yield was determined by placing a 100 µL sample of evenly distributed EB suspension into one well of a flat-bottomed 96-well plate, and counting the EBs in that sample. EB yield was calculated as 20× number of EBs counted in 100 µL. An aliquot of the EB suspension containing 500 EBs was transferred to a fresh tube. EBs were allowed to settle to bottom of tube, by incubating 5 mins at room temp. Media was removed, keeping pelleted EBs. EBs were resuspended in 3 mls of 0.5% modified mTeSR "A" medium (see Example 4), and vortexed well to mix.

The EB-containing 0.5% methylcellulose mixture was transferred to the strainer wells. The mixture was pipetted into the center of the wells, inside of the strainer well. A further 2 mL of 0.5% methylcellulose modified mTeSR "A" medium was added to each well, to increase the total volume to 5 mL. Sterile forceps were used to lift and replace the strainers in each well, to remove large air bubbles that can become trapped underneath the strainer wells. Plates were incubated in a standard tissue culture incubator, at 37° C., 5% CO2 and 95% humidity.

Every 2-4 days a complete media change was carried out. For this, sterilized (autoclaved) forceps were first placed into a sterile (autoclaved) beaker, with the handle end out. A washing plate was prepared, by filling wells of a fresh 6-well tissue culture plate with 5 mLs of DMEM/F12. Using the sterile forceps, the strainer well containing EBs was lifted out of reservoir plate, and transferred to the 1$^{st}$ well of the washing plate. Again using the sterile forceps, the strainer well was lifted in and out of the washing medium several times until it flowed freely. The strainer well was then transferred to the second well of the reservoir plate, and the washing was repeated. Finally, the strainer well containing EBs was moved to a fresh well (on the original plate or on a new plate). A fresh 5 mL aliquot of 0.5% methylcellulose based modified mTeSR "A" medium was pipetted onto the plate, by pipetting into the strainer using 6 cc needle and blunt-end needle. Using the sterile forceps, the strainer well was lifted and replaced, remove large air bubbles that can become trapped underneath the strainer.

Cultures were continued for 14 days, observing changes in the EBs over time.

The use of the filter plate system greatly facilitated the ease of media changes. It also reduced disruption to the EBs, since they were only removed from the incubator for a brief time, and were not pipetted. EBs could be observed atop the strainer during the culture period. Only single cells and not whole EBs were observed in the residual media after the strainer had been removed for media change, as shown in FIG. 23.

Example 10

Culture of EBs on Prototype Strainer Plate in Liquid Modified mTeSR Media

A filter plate system was prepared by: forming a strainer plate by aseptically removing a 40 μm cell strainer from its packaging, cutting off the handle, and placing the strainer plate inside a well of a 6-well tissue culture plate, which served as the reservoir plate. This was repeated for all 6 wells on the plate.

EBs were harvested from microwells and separated using a filter apparatus as described in Example 2. EBs were harvested from the strainer into 1 mL of liquid modified mTeSR "A" medium. An aliquot of the resulting EB suspension containing 500 EBs was transferred to each of 2 wells of the strainer plate. The mixture was pipetted into the center of the strainer wells. A further 5 mL of modified mTeSR "A" medium was added to each well, to increase the total volume to 5 mL. Plates were incubated in a standard tissue culture incubator, at 37° C., 5% CO2 and 95% humidity.

Every 2-4 days a complete media change was carried out. For this, sterilized (autoclaved) forceps were first placed into a sterile (autoclaved) beaker, with the handle end out. A washing plate was prepared, by filling wells of a fresh 6-well tissue culture plate with 5 mLs of DMEM/F12. Using the sterile forceps, the strainer plate containing EBs was lifted out of the reservoir plate, and transferred to the $1^{st}$ well of the washing plate. Again using the sterile forceps, the strainer plate was lifted in and out of the washing medium several times to wash. The strainer plate containing EBs was then moved to a fresh well (on the original plate or on a new plate), and a fresh 5 mL aliquot of modified mTeSR medium was pipetted onto the center of the strainer plate well.

Cultures were continued for 14 days, observing changes in the EBs over time, and counting the number of EBs per well (FIG. 25B). After 14 days, EBs were harvested from the plates. Using sterile forceps, the strainer well was lifted from the well and placed into a clean empty well. 7 mL of DMEM/F12 was added to the well, and pipetted to lift the EBs into suspension. The EB-containing suspension was then transferred to a fresh tube. The strainer well was washed again with a second 7 mL of DMEM/F12, and the wash was transferred to the same tube. EBs were allowed to settle to the bottom of the tube, supernatant was removed, and the EBs were resuspended in 1 mL of TrypLE (Invitrogen) to dissociate the EBs to single cells. Single cells were used for a variety of standard assays, including flow cytometry (FACS) assessment of pluripotency marker (SSEA3) and hematopoietic differentiation marker (CD34) expression, as shown in FIG. 25A.

The use of the filter plate system greatly facilitated the ease of media changes. It also reduced disruption to the EBs, since they were only removed from the incubator for a brief time, and were not pipetted. EBs could be observed atop the strainer during the culture period, and only single cells and not whole EBs were observed in the residual media after the strainer had been removed for media change (see FIG. 21).

Example 11

Culture of EBs on Prototype Strainer Plate in Liquid Modified mTeSR Media Supplemented with VEGF, SCF, and BMP-4

A prototype filter plate system was prepared by: forming a strainer plate byaseptically removing a 40 μm cell strainer from its packaging, cutting off the handle, and placing the strainer well inside a well of a 6-well tissue culture plate, which served as the reservoir plate. This was repeated for all 6 wells on the plate.

EBs were harvested from microwells and separated using an filter apparatus, as described hereinabove. EBs were harvested from the strainer into 1 mL of liquid modified mTeSR medium "A" (see Example 4), supplemented with cytokines designed to drive differentiation towards the hematopoietic lineage. Media was previously prepared by supplementing modified mTeSR liquid medium "A" with cytokines at the following final concentrations: 50 ng/ml vascular endothelian growth factor (VEGF), 40 ng/mL stem cell factor (SCF), and 40 ng/ml bone morphogenic protein-4 (BMP-4). An aliquot of the resulting EB suspension containing 500 EBs was transferred to the strainer well of the strainer plate. The mixture was pipetted into the center of the well. A further 5 mL of the same medium was added to each well, to increase the total volume to 5 mL. Plates were incubated in a standard tissue culture incubator, at 37° C., 5% CO2 and 95% humidity.

Every 2-4 days a complete media change was carried out. For this, sterilized (autoclaved) forceps were first placed into a sterile (autoclaved) beaker, with the handle end out. A washing plate was prepared, by filling wells of a fresh 6-well tissue culture plate with 5 mLs of DMEM/F12. Using the sterile forceps, the strainer plate containing EBs was lifted out of the strainer plate, and transferred to the $1^{st}$ well of the washing plate. Again using the sterile forceps, the strainer plate was lifted in and out of the washing medium several times to wash. The strainer plate containing EBs was then moved to a fresh well (on the original plate or on a new plate), and 5 mL of modified mTeSR "A" medium with cytokines VEGF, SCF and BMP4 as above was pipetted onto the center of the plate.

Cultures were continued for 14 days, observing changes in the EBs over time, and counting the number of EBs per well (FIG. 25B). After 14 days, EBs were harvested from the plates. Using sterile forceps, the strainer well was lifted from the reservoir well and placed into a clean empty well. 7 mL of DMEM/F12 was added to the well, and pipetted to lift the EBs into suspension. The EB-containing suspension was then transferred to a fresh tube. The strainer well was washed again with a second 7 mL of DMEM/F12, and the wash was transferred to the same tube. EBs were allowed to settle to the bottom of the tube, supernatant was removed, and the EBs were resuspended in 1 mL of TrypLE (Invitrogen) to dissociate the EBs to single cells. Single cells were used for a variety of standard assays, including flow cytometry (FACS) assessment of pluripotency marker (SSEA3) and hematopoietic differentiation marker (CD34) expression, as shown in FIG. 25A.

The use of the filter plate system greatly facilitated the ease of media changes. It also reduced disruption to the EBs, since they were only removed from the incubator for a brief time, and were not pipetted. EBs could be observed atop the mesh during the culture period. Only single cells and not whole EBs were observed in the residual media after the strainer plate had been removed for media change, as shown in FIG. 22.

Example 12

Neurosphere Cultures Generated Using Mouse Embryonic Day 14 Cortical Cells

Neural cells can be obtained from primary embryonic, post-natal or adult CNS tissue from any region of the neuroaxis including but not limited to the striatum, septum, cortex, ventral mesencephalon, septum, midbrain, cerebellum or spinal cord from murine, rodent and human. Neural cells can also be obtained from cultured cells such as those generated using the Neurosphere Assay or any method known to one skilled in the art of neural tissue culture. Neural cells can also be obtained from any stage of embryonic stem cell cultures according to any standard procedure for culturing ES cells.

For example, cortices are dissected from Embryonic Day 14 CD1 albino mouse embryos (Charles River) using standard microdissection techniques. Tissue is collected in phosphate-buffered saline with 2% glucose then mechanically dissociated using a fire-polished glass pipette into a single cell suspension, washed once and filtered through a 40 um nylon cell strainer (Falcon) and diluted in complete NeuroCult™ medium (NeuroCult® Basal Medium & NeuroCult™ Proliferation Supplements; StemCell Technologies Inc. with 20 ng/ml of EGF). Cells are cultured for 7 days to generate neurospheres. Day 7 neurospheres are collected from the culture in a tube and centrifuged at low speed at 400 rpm for 5 minutes to pellet neurospheres and not the single cells. Neurospheres which are more dense form a pellet and most of the single cells remain in the supernatant. The supernatant is removed and the neurospheres are mechanically dissociated into a single cell suspension for further application.

Example 13

Separation of Large and Small Neuropheres Using Prototype Filter Apparatus

Neurospheres were generated as described in Example 12. After 7 days, neurospheres were dissociated into single cells, and replated at $10^5$ cells per mL in complete NeuroCult® Proliferation Medium (STEMCELL Technologies Inc.) with 20 ng/mL EGF. These were then cultured for a further 7 days to allow neurospheres to reform.

The 7 day neurosphere cultures were then separated using a filter apparatus, as described hereinabove with respect to FIG. 1. The filter apparatus was fashioned from available materials as described previously (Example 3). Briefly, the plastic casings from 2 commercially available cell strainers were attached together at their flanges, with a 50 µm nylon mesh (BioDesign Inc.) inserted between them. Side walls were then fashioned onto the device using materials available in the lab such as tape and parafilm, to create a reservoir. The resulting device is shown in FIG. 15. This prototype device was testing without sterilization.

The filter apparatus was placed atop a 50 mL tube labeled "neurosphere filtrate", and the entire neurosphere culture was transferred into the reservoir at the top of the filter apparatus. 2 mL of PBS was used to wash out the neurosphere flask, and this wash solution was also placed into the strainer, with flowthrough collected in the same "filtrate" tube.

The filter apparatus was then removed from the "neurosphere filtrate" tube, inverted, and placed securely atop a second 50 mL tube, labeled "neurosphere filtrand". 5 mL of PBS was transferred to the top reservoir, to wash any particles trapped on the filter into the filtrand tube. The filtrate tube was then centrifuged at 1200 rpm for 5 mins, the supernatant was discarded, and the pellet was resuspended in 1 mL of PBS.

Aggregate yields in each tube were determined by transferring 10 uL of each suspension to 1 well of a 96-well flat bottomed plate, counting the aggregates in that 10 µL aliquot, and calculating the total number of aggregates in the entire suspension. Single cell yields were determined by diluting 10 ul of each suspension in 10 µL of trypan blue solution, and counting single cells on a hematocytometer. Yields of neurosphere and single cells in each tube are shown in Table 4. Although there were slightly more neurospheres captured in the filtrand tubes, there were also a significant number of neurospheres present in the filtrate tube. Thus, these neurospheres must have passed through the 50 µm filter. As shown in FIG. 19, the sizes of neurospheres captured in the 2 tubes were significantly different. Only small neurospheres were present in the filtrate tube, whereas the filtrand tube also contained much larger neurospheres. Single cells and small neurospheres were also present in the filtrand tube, probably due to insufficient washing of the filtering apparatus prior to inverting. The filter apparatus can therefore be effectively used to achieve size fractionation of cellular aggregates, based on the pore size of the filter being used. Particles and cellular aggregates passing into the filtrate tube are smaller than the pore size, and those larger than the pore size were collected on the filter for recovery into the filtrand tube (see FIG. 19).

TABLE 5

| Yields of neurospheres and single cells after separation in prototype filter apparatus. | | | |
| --- | --- | --- | --- |
| Experiment No. | Tube Type | Total No. of Neurospheres | Total No. of Single Cells |
| 1 | Neurosphere filtrate | 2,800 | 430,000 |
|   | Neurosphere filtrand | 7,500 | 1,325,000 |
| 2 | Neurosphere filtrate | 16,400 | 1,210,000 |
|   | Neurosphere filtrand | 17,000 | 525,000 |

Example 14

Testing Mesh Materials for Reversible Straining of Human EBs

Prototype filter apparatuses were made as described in Example 3, using the casing from a Cell Strainer (BD), but with mesh from a variety of sources. In this way various materials, pore widths, and suppliers of mesh could be tested for their performance in straining and retaining AggreWell-formed EBs away from the remaining non-incorporated single cells.

The following types of mesh were tested: (1) Stainless steel mesh, 33 micron pore size (wire-mesh.ws), (2) Nylon mesh, 50 micron pore size (Biodesign Inc.), (3) expanded PTFE (teflon), 90 micron pore size (Dexmet), (4) Nylon mesh, 30 micron pore size (Small Parts Inc.), (5) Nylon mesh, 50 micron pore size (Small Parts Inc.), (6) Nylon mesh, 37 micron pore size (Sefar). These were compared against: (7) 40 micron cell strainer (BD) used in the unconventional manner described in Example 2. Yields of single cells and of aggregates were measured from both the filtrate and the filtrand tubes after running AggreWell-generated EB samples through each filter.

The results of EB and single cell yields are shown in FIG. 31. Mesh #3 had the worst separation of EBs, with a significant number of EBs passing thru the 90 micron filter into the filtrate tube, and consequently significantly reduced EB yield collected in the filtrand. All of the materials tested were able to efficiently separate single cells into the filtrate tube. However, not all materials were equivalent in their ability to pass liquid through. The expanded Teflon material (mesh #3) was extremely difficult to pass through, as was the stainless steel material (mesh #1). These samples had to be pipetted multiple times, to force the sample through the mesh, and that resulted in bubbles being formed, as well as more destruction of the EBs. Nylon materials in the 30-50 micron range of pore sizes were all able to efficiently separate EBs from single cells. The samples flowed through easier if the mesh was pre-wetted, otherwise the sample sometimes stayed within the upper reservoir chamber until the whole contraption was gently tapped, or until sufficient volume was added to give adequate weight to push the liquid through. Overall, of all the materials tested, nylon was the most suitable material for filtration of cellular aggregates, and pore sizes of greater than 30 and less than 90 were most useful for separation of EBs containing 2,000 cells each.

Example 15

Manufacture of Prototype-2 Filter Apparatuses

Design drawings and 3-D STL files were prepared, for two sizes of filter apparatuses. The larger size was designed to fit securely atop a 50 mL test tube, and the smaller size to fit securely atop a 14-15 mL test tube. Several variations on handle size and barrel (reservoir) length were compared.

Other modifications were added to the initial design. First, an arrow was added to the outside of the narrower cylinder (reservoir) to give directionality. The device is to be used starting with the narrow end up (arrow pointed up), so that essentially all trapped aggregates or particles will be washed off the filter, and essentially none will remain at the filter edges. Second, a bump was added to the handle, to give further directionality. The bump pointed towards the narrow end, and could be easily felt by the user during use of the device.

3-D design files were sent to a contact plastics manufacturer, where stereolithography was used to generate prototype parts out of resin. Specifically, Watershed™ 18420 and Watershed™ 11122 resins (DSM Somos, Elgin, Ill., USA) were used. In total, 12 large (50-mL) and 12 small (15-mL) prototypes were individually made by the stereolithography process. Each filter apparatus was made in 2 parts, so that mesh could be inserted in the middle, and it was all sealed together with small droplets of 5-minute epoxy. In this way various types, sizes, and sources of mesh could be tested.

Photographs of prototype-2 filter apparatuses are shown in FIG. 30. Prototype-2 filter apparatuses were used in the experiments detailed in Examples 16-18.

Example 16

Dissociation of Soft Tissue into Single Cells

Two BALB/C mice were sacrificed and spleens were removed by dissection of the carcasses. One spleen was pushed through a 40 micron cell strainer (BD), using a 3 cc syringe plunger, and the strainer was rinsed with 5 mls of PBS 2% FBS. The second spleen was pushed through a prototype-2 filter apparatus, with 37 micron nylon mesh (Small Parts Inc.), using a 3 cc syringe plunger, and the strainer was similarly rinsed with 5 mls of PBS 2% FBS. As shown in FIG. 32, the yield of cells was similar from either straining technique. Thus the filter apparatus can also be used in a single direction, as to provide a single cell suspension from a soft tissue such as murine spleen.

Example 17

Size Fractionation of Neurospheres Using Prototype-2 Filter Apparatuses with Range of Mesh Sizes Prototype-2 filter apparatuses were made with filters of a variety of pore sizes. In this experiment, nylon mesh was used, with pore sizes of 850 (Small Parts Inc), 420 (Sefar), 350 (Small Parts Inc), 250 (Small Parts Inc), 105 (Sefar), 50 (Biodesign), and 37 (Small Parts Inc) microns. Each nylon mesh was sealed into a separate prototype-2 strainer (see Example 15), of the smaller size (to fit atop 15 ml tube), using small droplets of 5-minute epoxy. Filter apparatuses were not sterilized prior to use.

These prototypes were designed to be stackable. One side of the device is more narrow than the other, and the narrow end of one device will fit inside the wide end of the next device (see FIG. 26C). In this way, it should be possible to run a sample through multiple filters in sequence, and retain the intermediate sized particles in each inter-filter space. These prototype-2 filter apparatuses were manufactured in 2 parts, so that a variety of filters could be tested, and there was some leakage of liquid out of the glued edge, when pressure was applied to help force the sample through the stacked filters. This would not be the case with filtering apparatuses manufactured in a single part (eg. through injection moulding, see Example 19).

Size fractionation was done by sequential filtration of the sample, starting with the strainer containing the largest pore size and working down. Thus the first filter apparatus used had a pore size of 850 microns. Anything larger than 850 microns should be retained on that filter, and small particles should have passed through. The retained fraction was retrieved by the usual method of flipping the strainer over onto a fresh tube, and washing the (now bottom) surface with medium. In this case, the filtrate, containing particles less than the pore size, was then subjected to filtration by the next lower pore size filter apparatus, following the same method of aggregate recovery. In this manner, strainers used sequentially were: 850, 420, 350, 250, 105, 60, 37 microns. After harvesting each sample from its filter apparatus, an aliquot of the recovered material was placed into a tissue culture plate, and photographs were taken at 20× magnification (FIG. 33A). ImageJ software was then used to determine the sizes of the recovered particles. Frequencies of particle sizes from each filter size are shown in FIG. 33B. In this manner, the sequential use of filter apparatuses was successfully able to segregate these large particles based on size.

Example 18

Fractionation of Human Embryonic Stem Cell Clumps for Optimized Passaging

H9 human embryonic stem cell line was maintained on mTeSR®1 (STEMCELL Technologies) and Matrigel™ (Becton Dickson). Every 4-6 days the cultures were passaged according to the recommendations in the mTeSR®1 manual. Briefly, this passaging regime involves adding 1 mg/ml dispase to the cultures, incubating at 37° C. for 5-7 minutes until the edges of the colonies start to lift off of the plate. The dispase is then removed, and the cultures are washed twice with DMEM/F12. Clumps of cells are then scraped off the plate, either with a Cell Scraper (Corning) or with a 5 mL glass pipette. The clumps are resuspended in fresh mTeSR®1 culture medium for further passage. Ideally, hES or iPS cultures should be seeded with equally sized clumps, so that the emerging colonies will grow at the same rate and be ready for passaging at the same time. Moreover, clumps that are too small may not adhere to the matrigel-coated dish, and clumps that are too large will have an increased chance of unwanted, spontaneous differentiation during the subsequent culture period. For these reasons, it is recommended to generate a clump suspension wherein the clumps are as equally sized as possible, and of a size that will hang in suspension for a few moments after the tube is inverted, rather than sinking to the bottom of the tube. Once the clump suspension is deemed satisfactory, a proportion of the clump suspension (eg. 1/5th to 1/10th of the contents recovered from one well) is seeded onto a fresh, matrigel-coated well. Maintenance medium is changed daily, and cultures are passaged in this manner every 4-7 days.

Trituration does not adequately control clump size, as there will often be clumps that are too large or too small within the suspension. For this reason we sought to use the filtering apparatus to fractionate hES clumps of the optimal size for passaging. This would make PSC passaging more efficient, standardized, and increase the health of PSC cultures.

In this example, sterilized Prototype-2 filter apparatuses of various sizes were used to fractionate clumps, and those size fractionations were used to determine the optimal clump size to generate a successful culture. Prototype filter apparatuses were manufactured by the process described in Example 15. Mesh sizes were selected to include a range of sizes from 50 µm to 420 µm. In this experiment we chose nylon mesh of 420 (Sefar), 350 (Small Parts Inc), 250 (Small Parts Inc), 105 (Sefar), 100 (Sefar), and 50 (Biodesign Inc.) µm pore widths.

In this Example, a full 6-well plate of H9 hES cells (p64) was used. Clumps were harvested by dispase, pooling the resulting clumps from 3 wells per tube. After washing & resuspending the clumps in mTeSR®1, one of the two tubes of clump suspension was well triturated, to generate a population containing small and medium sized clumps. The second tube was not triturated further, to keep the clumps at medium to large size. The 2 tubes were then pooled, to generate a mixed population with small to large sized clumps. The suspension was passed through the 420 micron filter apparatus, and aggregates trapped on the filter (>420 microns) were washed off with 2 mls of mTeSR®1 and retained. The flowthru from the first filtration step (<420 microns) was then passed through the 350 micron filter, and aggregates trapped on that filter were washed off with 2 mls of mTeSR®1 and retained. The process was repeated for 250, 100, and 50 micron filter apparatuses. In this manner, the suspension was sequentially strained through 420, 350, 250, 100, and 50 micron filters, to generate clump suspensions of >420; 350-420; 250-350; 100-250; 50-100; and <50 microns in diameter. Fractions of ½, ¼, and ⅛ of each clump suspension was seeded onto a fresh matrigel-coated well. In addition, due to the large number of aggregates present in the <50 and 50-100 micron fractions (determined to be approximately 12,800 and 4,400 clump yields respectively), smaller fractions of the suspension were plated, at approximately 350 clumps per well (54 µl and 160 ul, respectively).

After 24 hrs, the plates were examined for hES clump attachment. Plates seeded with clumps from the 0-50 micron suspension contained a large number of non-attached cells and small aggregates. These dead cells were discarded with the first media change. Other wells did not contain as many non-adhered single cells.

After 5 days, the plates were examined for hES colony size. Plates seeded with hES clumps from the suspensions larger than 250 microns contained relatively few colony forming clumps (Table 6, calculated from the number of resultant colonies multiplied by the seeding dilution). Surprisingly, the colonies that did form from these larger size fractions were all of relatively the same size, suggesting that any extra-large clumps were either broken up in the pipetting steps of the procedure or were not able to attach & grow. The majority of the clumps were fractionated into the 50-100 and <50 micron fractions. As shown in Table 6 and FIG. 36, there was a significant difference both in the clump size after fractionation (FIG. 36A) and in the resulting day-5 colony size (FIG. 36B) from these two size fractions. The removal of small (<50 micron) clumps significantly reduced the number of non-attached single cells and immature colonies at the time of passaging, which increases the overall health of the culture. Further fractionation within the 50-100 micron size will help to determine the optimal clump size for passaging.

TABLE 6

Colonies formed 6 days after seeding of size-fractionated hES clumps

| hES Clump Fraction Size Range (microns) | Number of Colony-forming clumps per suspension | Average Colony Size |
| --- | --- | --- |
| >420 | 58 | Medium-large |
| 350-420 | 16 | Medium-large |
| 250-350 | 33 | Large |
| 100-250 | 1334 | Medium-large |
| 50-100 | 1525 | Medium-large |
| <50 | 4740 | Small |

Example 19

Manufacture and Testing of Injection Molded Filter Apparatuses

The original design files were modified based on testing results from prototype-2 parts. First, the cone-shaped bump on the handle was removed, and replaced with the STEM-CELL corporate logo. This gives similar directionality function, with improved aesthetics. Second, the polystyrene material was dyed orange, but remained largely transparent. The transparency improves ability to visualize the volume of liquid in the reservoir (eg. in case the filter gets clogged). The colouring will give identity to this specific part. Ultimately, different pore sizes will be manufactured, each with a different polystyrene colouring for easy recognition.

3-D design files were sent to a contract manufacturer for production of the part by injection moulding. In the first instance, a mud set mould was created, with a 1-cavity 14-ml strainer mould and a 1-cavity 50-ml strainer mould. Polypropylene material was used for the casing, and nylon mesh with 37 micron pore diameter was used for the filter. The part was moulded onto the nylon mesh, which was manually advanced by the operator. Examples of large (50 mL) and small (15 mL) filter apparatuses made by injection moulding are shown in FIG. 34.

Some of the injection molded filter apparatuses were sealed into individual pouches (Tyvek or plastic pouches) and irradiated by gamma irradiation for sterilization of the device. Sterilized 15-ml filter apparatuses were used to separate and retain EBs after formation in AggreWell™400, and the results were compared to control EB harvesting by upside-down Cell Strainer (BD) as described in Example 2. As shown in FIG. 35, the manufactured filter apparatuses were equally able to selectively harvest EBs, with equivalent EB yields as the control method.

Moreover, the filter apparatus had added ergonomic and performance benefits. The filter apparatus was securely held atop the test tube without fear of losing the EB sample due to the strainer falling off the tube. The larger handle size on the filter apparatus made handling the strainer and flipping it over for sample collection much easier. The solid side walls prevented accidental contamination of the sample by inadvertent touching of the cylinder walls. Also, the filter apparatuses used here were designed to fit atop 14-15 mL test tubes, whereas the control Cell Strainers had to be used with 50 mL tubes. The reduced internal surface area of a 15 mL tube reduces the chance of EBs being lost stuck to the sides of the tube, and reduces the necessary amount of washes to the collection tube. Overall, the filter apparatus gave equivalent filtering performance as the control method, but with much greater ease of use & comfort.

The invention claimed is:

1. A filter apparatus comprising:
    a) a first reservoir defined by an inner circumferential surface of a first sidewall;
    b) a first opening defined by the first sidewall, the first opening in communication with the first reservoir and defining a first inlet-outlet port to the first reservoir, the first opening open to the environment;
    c) a second reservoir defined by an inner circumferential surface of a second sidewall;
    d) a second opening defined by the second sidewall, the second opening in communication with the second reservoir and defining a second inlet-outlet port to the second reservoir, the second opening open to the environment;
    e) one filter centrally positioned between the first opening and the second opening, the one filter having a first surface adjacent and in communication with the first reservoir and spaced from the first opening, and a second surface opposed to the first surface, the second surface adjacent and in communication with the second reservoir and spaced from the second opening, the one filter having a pore size of between 5 microns and 100 microns;
    f) a first seating surface seatable on a rim of a fluid vessel to couple the filter apparatus to the fluid vessel, wherein when the first seating surface is seated on the rim of the fluid vessel, the first opening is positioned within the fluid vessel, and the second opening is positioned above the fluid vessel; and
    g) a second seating surface seatable on the rim of the fluid vessel to couple the filter apparatus to the fluid vessel, wherein when the second seating surface is seated on the rim of the fluid vessel, the second opening is positioned within the fluid vessel, and the first opening is positioned above the fluid vessel;
    wherein the first side wall and second sidewall are both generally cylindrical and have a constant diameter between the filter and the first opening and the filter and the second opening, respectively, and
    wherein the first seating surface and second seating surface are provided by at least a first flange extending radially outwardly from an outer circumferential surface of at least one of the first sidewall and the second sidewall.

2. The filter apparatus of claim 1, wherein:
    a) the first sidewall has a first inner face;
    b) the second sidewall has a second inner face; and
    c) the one filter is secured between the first and second inner faces.

3. The filter apparatus of claim 1 wherein
    a) the first seating surface is provided by the first flange; and
    b) the second seating surface is provided by a second flange.

4. The filter apparatus of claim 3, wherein the first flange is integral with the second sidewall, and the second flange is integral with the first sidewall.

5. The filter apparatus of claim 1, further comprising a handle coupled to one of the first sidewall and the second sidewall.

6. The filter apparatus of claim 1, wherein the first sidewall extends substantially perpendicularly to the first surface, and the second sidewall extends substantially perpendicularly to the second surface.

7. The filter apparatus of claim 1, wherein the one filter comprises a membrane fabricated from a material selected from the group consisting nylon, polypropylene, polyethylene, polyester, polyetheretherketone, polytetrafluoroethyline, polyfluoroethylenepropylene, polyvinyls, polysulfone, polyvinyl fluoride, polychlorotrifluoroethylene, ethylene tetrafluoroethylene, aluminum, brass, copper, nickel, bronze, steel, stainless steel and titanium.

8. The filter apparatus of claim 1, wherein the first reservoir is removably positioned adjacent with the first surface, and the second reservoir is removably positioned adjacent the second surface.

9. The filter apparatus of claim 1, wherein the one filter comprises a single membrane.

10. The filter apparatus of claim 1, wherein the first reservoir has a volume of between about 0.5 cm$^3$ and 1000 cm$^3$, and the second reservoir has a volume of between about 0.5 cm$^3$ and 1000 cm$^3$.

11. The filter apparatus of claim 1, wherein the filter is sandwiched between the first and second sidewalls to secure the filter in a fixed position.

12. A filter apparatus comprising:
    a) a filter having first and second opposed surfaces, the filter having a pore size of between 5 microns and 100 microns;
    b) a first reservoir positioned adjacent with the first surface and in communication with the first surface;
    c) a first inlet-outlet port in communication with the first reservoir and spaced from the first surface;
    d) a second reservoir positioned adjacent the second surface, and in communication with the second surface; and
    e) a second inlet-outlet port in communication with the second reservoir and spaced from the second surface;
    wherein the first reservoir is defined by a first sidewall that extends from the filter to the first inlet-outlet port and is substantially perpendicular to the first surface between the filter and the first inlet-outlet port, and the first inlet-outlet port is a first opening defined by an outermost end face of the first sidewall, and
    wherein the second reservoir is defined by a second sidewall that extends from the filter to the second inlet-outlet port and is substantially perpendicular to the second surface between the filter and the second inlet-outlet port, and the second inlet-outlet port is a second opening defined by an outermost end face of the second sidewall.

13. The filter apparatus of claim 12, wherein the one filter is centrally positioned between the first inlet-outlet port and the second inlet outlet port.

14. The filter apparatus of claim 12, wherein:
    a) the first sidewall has a first inner face; and
    b) the second sidewall has a second inner face; and
    c) the filter is secured between the first and second inner faces to sandwich the filter between the first and second sidewalls and secure the filter in a fixed position.

15. The filter apparatus of claim 12, wherein the first reservoir has a volume of between about 0.5 cm$^3$ and 1000 cm$^3$, and the second reservoir has a volume of between about 0.5 cm$^3$ and 1000 cm$^3$.

16. A filter apparatus comprising:
a) a filter having first and second opposed surfaces, the filter having a pore size of between 5 microns and 100 microns;
b) a first reservoir defined by a first sidewall, the first reservoir adjacent the first surface and in communication with the first surface,
c) a first inlet-outlet port in communication with the first reservoir and spaced from the first surface;
d) a second reservoir defined by a second sidewall and positioned adjacent the second surface, and in communication with the second surface; and
e) a second inlet-outlet port in communication with the second reservoir and spaced from the second surface;
wherein the filter is centrally positioned between the first inlet-outlet port and the second inlet-outlet port, and
wherein the first reservoir has a first diameter that is generally constant between the filter and the first inlet outlet port, and the second reservoir has a second diameter that is generally constant between the filter and the second inlet-outlet port, and the second diameter is less than the first diameter.

17. The filter apparatus of claim 16, wherein the first sidewall is substantially perpendicular to the first surface between the filter and the first inlet-outlet port, and the second sidewall is substantially perpendicular to the second surface between the filter and the second inlet-outlet port.

18. The filter apparatus of claim 1, wherein the first opening is defined by an outermost end face of the first sidewall, and the second opening is defined by an outermost end face of the second sidewall.

19. The filter apparatus of claim 1, wherein the first reservoir has a first diameter and the second reservoir has a second diameter, and the second diameter is less than the first diameter.

20. The filter apparatus of claim 12, wherein the first side wall and second sidewall are both generally cylindrical.

21. The filter apparatus of claim 12, wherein the first reservoir has a first diameter and the second reservoir has a second diameter, and the second diameter is less than the first diameter.

22. The filter apparatus of claim 16, wherein the first inlet-outlet port is a first opening defined by an outermost end face of the first sidewall and the second inlet-outlet port is a second opening defined by an outermost end face of the second sidewall.

23. The filter apparatus of claim 16, wherein the first side wall and second sidewall are both generally cylindrical.

24. The filter apparatus of claim 1, wherein the pore size is about 40 microns.

25. The filter apparatus of claim 12, wherein the pore size is about 40 microns.

26. The filter apparatus of claim 16, wherein the pore size is about 40 microns.

* * * * *